US005641654A

United States Patent [19]

Maki et al.

[11] Patent Number: 5,641,654

[45] Date of Patent: Jun. 24, 1997

[54] NON-A NON-B HEPATITIS SPECIFIC ANTIGEN AND ITS USE IN HEPATITIS

[75] Inventors: Noboru Maki; Kenjiro Yamaguchi, both of Iruma-gun; Ayumi Toyoshima, Kamifukuoka; Michinori Kohara, Tokorozawa, all of Japan

[73] Assignee: Tonen Corporation, Tokyo, Japan

[21] Appl. No.: 81,072

[22] Filed: Jun. 22, 1993

Related U.S. Application Data

[63] Continuation of Ser. No. 726,141, Jul. 8, 1991, abandoned.

[30] Foreign Application Priority Data

| | | | |
|---|---|---|---|
| Jul. 9, 1990 | [JP] | Japan | 2-180889 |
| Nov. 30, 1990 | [JP] | Japan | 2-339589 |
| Dec. 20, 1990 | [JP] | Japan | 2-413844 |

[51] Int. Cl.[6] .............................. C12P 21/02; C12N 1/21; C12N 15/71

[52] U.S. Cl. ................ 435/69.3; 435/252.3; 435/252.33; 435/252.5; 435/254.2; 435/320.1; 536/23.72

[58] Field of Search ............................... 435/69.1, 320.1, 435/172.3, 69.3, 252.3, 252.33, 252.5, 254.2; 536/23.1, 23.72, 24.3, 24.33

[56] References Cited

FOREIGN PATENT DOCUMENTS

| | | |
|---|---|---|
| 0318216 | 5/1989 | European Pat. Off. . |
| 0388232 | 9/1990 | European Pat. Off. . |
| 0464287A1 | 1/1992 | European Pat. Off. . |

OTHER PUBLICATIONS

Kubo et al. *Nucleic Acids Research,* vol. 17, No. 24, 1989, pp. 10367–10372.

Okamoto et al. *Japan J. Exp. Med.,* vol. 60, No. 3, 1990, pp. 167–177.

Kato et al. *Proceedings of the National Academy of Sciences of the USA,* vol. 87, No. 24, Dec. 1990, pp. 9524–9528.

Kato et al., *Proc. Japan Acad.* vol. 65, Ser. B; Nov. 1989, pp. 219–223.

Arima et al., *Gastroenterologia Japonica* vol. 24 No. 5, 1989, pp. 540–544.

Ogata et al. *Proceedings of the National Academy of Sciences of the USA* vol. 88, No. 15, Apr. 1991, pp. 3392–3396.

Takamizawa et al., *Journal of Virology,* vol. 65, No. 3, Mar. 1991.

Choo et al., *Proceedings of the National Academy of Sciences of the USA* vol. 88, Mar. 1991, pp. 2451–2455.

Arima et al., *Gastroenterologia Japonica,* vol. 24, No. 6, 1989, pp. 687–691.

*Primary Examiner*—David Guzo

*Attorney, Agent, or Firm*—David G. Conlin; David S. Resnick

[57] ABSTRACT

This invention relates to a DNA fragment comprising a base sequence encoding a non-A non-B hepatitis-specific antigen polypeptide, said base sequence being obtained using genetic engineering techniques from non-A non-B hepatitis virus RNA which is isolated directly from blood plasma from non-A non-B hepatitis patients, to an expression vector and a transformant for use in the expression of the DNA fragment, to a single strand DNA sequence for PCR primer, and to use of said polypeptide and said single strand DNA sequence in the detection of the non-A non-B hepatitis virus. The recombinant polypeptide and the single strand DNA sequence for PCR primer make it possible to detect the non-A non-B hepatitis virus with extremely high accuracy.

8 Claims, 30 Drawing Sheets

Fig. 1a

```
        10        20        30        40        50        60
CGCAGTCATTCCAAGTGGCCCATCTACACGCTCCCACTGGCAGCGGCAAGAGTACTAAAG
  GlnSerPheGlnValAlaHisLeuHisAlaProThrGlySerGlyLysSerThrLysVal

        70        80        90       100       110       120
TGCCGGCTGCATATGCCAGCCAAGGGTACAAGGTGCTCGTCCTCAACCCGTCCGTTGCCG
  ProAlaAlaTyrAlaSerGlnGlyTyrLysValLeuValLeuAsnProSerValAlaAla

       130       140       150       160       170       180
CCACCTTAGGTTTTGGAGCGTATATGTCTAAGGCACATGGCACCGACCCCAACATCAGAA
  ThrLeuGlyPheGlyAlaTyrMetSerLysAlaHisGlyThrAspProAsnIleArgThr

       190       200       210       220       230       240
CTGGGGTAAGGACTATCACCACAGGCGCCCCCATCACGTACTCCACCTACGGCAAGTTCC
  GlyValArgThrIleThrThrGlyAlaProIleThrTyrSerThrTyrGlyLysPheLeu

       250       260       270       280       290       300
TTGCCGACGGTGGTTGTTCTGGGGGCGCTTATGACATCATAATGTGTGATGAGTGCCACT
  AlaAspGlyGlyCysSerGlyGlyAlaTyrAspIleIleMetCysAspGluCysHisSer

       310       320       330       340       350       360
CAACTGACGCGACTTCCATCTTGGGCATCGGCACGGTCCTGGACCAAGCGGAGACGGCTG
  ThrAspAlaThrSerIleLeuGlyIleGlyThrValLeuAspGlnAlaGluThrAlaGly
```

Fig. 1b

```
        370        380        390        400        410        420
GAGCACGGCTCGTCGTGCTCGCCACCGCTACGCCTCCGGGATCGGTCACCGTGCCACACC
  AlaArgLeuValValLeuAlaThrAlaThrProProGlySerValThrValProHisPro

        430        440        450        460        470        480
CGAATATTGAGGAGGTGGCCCTGTCTAACACTGGAGAGATCCCCTTCTATGGCAAAGGCA
  AsnIleGluGluValAlaLeuSerAsnThrGlyGluIleProPheTyrGlyLysGlyIle

        490        500        510        520        530        540
TCCCCATTGAAGTCATCAAGGGGGGAAGGCATCTCATTTTCTGCCATTCCAAGAAGAAGT
  ProIleGluValIleLysGlyGlyArgHisLeuIlePheCysHisSerLysLysLysCys

        550        560        570        580        590        600
GCGACGAGCTCGCCGCGAAGTTGTCAGGCCTCGGGATTAATGCTGTGGCATACTACCGGG
  AspGluLeuAlaAlaLysLeuSerGlyLeuGlyIleAsnAlaValAlaTyrTyrArgGly

        610        620        630        640        650        660
GTCTTGATGTGTCCGTCATACCGACCAGCGGAGACGTCGTTGTCGTGGCAACAGACGCTC
  LeuAspValSerValIleProThrSerGlyAspValValValValAlaThrAspAlaLeu

        670        680        690        700        710        720
TAATGACGGGCTATACCGGCGATTTTGACTCAGTGATCGACTGTAACACATGCGTCACCC
  MetThrGlyTyrThrGlyAspPheAspSerValIleAspCysAsnThrCysValThrGln

        730        740        750        760
AGACAGTCGACTTCAGCTTGGACCCCACCTTCACCATTGAGAC
  ThrValAspPheSerLeuAspProThrPheThrIleGlu
```

Fig. 2

```
        10        20        30        40        50        60
CACGCCCGGTTTGCCCGTGTGTCAAGACCACCTGGAGTTCTGGGAAGCGGTCTTCACAGG
 ThrProGlyLeuProValCysGlnAspHisLeuGluPheTrpGluAlaValPheThrGly

        70        80        90       100       110       120
TCTCACGCACATTGATGCCCACTTCCTCTCCCAGACAAAGCAAGGAGGAGACAACTTCGC
 LeuThrHisIleAspAlaHisPheLeuSerGlnThrLysGlnGlyGlyAspAsnPheAla

       130       140       150       160       170       180
GTATCTAACGGCCTACCAGGCCACAGTGTGCGCTAGGGCAAAGGCCCCTCCTCCCTCGTG
 TyrLeuThrAlaTyrGlnAlaThrValCysAlaArgAlaLysAlaProProProSerTrp

       190       200       210       220       230       240
GGATGTGATGTGGAAATGTCTAGCTAGGCTGAAGCCTACACTAATTGGTCCTACCCCCCT
 AspValMetTrpLysCysLeuAlaArgLeuLysProThrLeuIleGlyProThrProLeu

       250       260       270       280       290       300
CCTGTACCGCTTGGGTGCCGTGACCAACGAGGTTACCCTGACGCACCCCGTGACGAAATA
 LeuTyrArgLeuGlyAlaValThrAsnGluValThrLeuThrHisProValThrLysTyr

       310       320       330       340       350       360
CATCGCCACGTGCATGCAAGCTGACCTCGAGATCATGACGAGCACATGGGTCCTAGCAGG
 IleAlaThrCysMetGlnAlaAspLeuGluIleMetThrSerThrTrpValLeuAlaGly

       370       380       390       400       410       420
GGGGGTGCTAGCCGCCGTGGCAGCTTACTGCCTGGCAACCGGCTGTGTTTCCATCATCGG
 GlyValLeuAlaAlaValAlaAlaTyrCysLeuAlaThrGlyCysValSerIleIleGly

       430       440       450       460       470       480
CCGCCTACACCTGAATGATCAAGTGGTTGTGACTCCTGACAAAGAAATCTTATATGAGGC
 ArgLeuHisLeuAsnAspGlnValValValThrProAspLysGluIleLeuTyrGluAla

       490       500       510       520       530       540
CTTTGATGAGATGGAAGAATGCGCCTCCAAAGCCGCCCTCATTGAGGAAGGGCAGCGGAT
 PheAspGluMetGluGluCysAlaSerLysAlaAlaLeuIleGluGluGlyGlnArgMet

       550       560       570       580       590       600
GGCGGAGATGCTCAAGTCTAAGATACAAGGCCTCCTACAACAGGCCACAAGACAGGCCCA
 AlaGluMetLeuLysSerLysIleGlnGlyLeuLeuGlnGlnAlaThrArgGlnAlaGln

       610
AGACATACAGCCAGC
 AspIleGlnPro
```

Fig. 3a

```
               10        20        30        40        50        60
GTGAGCGAGCCTCAGGAATGTTTGACAGTGTAGTGCTCTGTGAGTGCTATGACGCAGGGG
 GluArgAlaSerGlyMetPheAspSerValValLeuCysGluCysTyrAspAlaGlyAla

               70        80        90       100       110       120
CTGCATGGTACGAGCTTACACCAGCGGAGACCACCGTCAGGCTCAGAGCGTATTTCAACA
 AlaTrpTyrGluLeuThrProAlaGluThrThrValArgLeuArgAlaTyrPheAsnThr

              130       140       150       160       170       180
CACCTGGCTTGCCTGTGTGTCAAGACCATCTTGAGTTCTGGGAGGCAGTTTTCACCGGCC
 ProGlyLeuProValCysGlnAspHisLeuGluPheTrpGluAlaValPheThrGlyLeu

              190       200       210       220       230       240
TCACACACATAGATGCCCACTTCCTTTCCCAGACAAAGCAAGCAGGGGACAATTTCGCAT
 ThrHisIleAspAlaHisPheLeuSerGlnThrLysGlnAlaGlyAspAsnPheAlaTyr

              250       260       270       280       290       300
ACTTGACAGCCTACCAGGCTACAGTGTGCGCCAGAGCCAAAGCCCCTCCCCCGTCCTGGG
 LeuThrAlaTyrGlnAlaThrValCysAlaArgAlaLysAlaProProProSerTrpAsp

              310       320       330       340       350       360
ACGTCATGTGGAAGTGCCTGACTCGGCTCAAGCCCACGCTTGTGGCCCCTACACCCCTTC
 ValMetTrpLysCysLeuThrArgLeuLysProThrLeuValAlaProThrProLeuLeu
```

Fig. 3b

```
       370         380         390         400         410         420
TGTACCGTTTAGGCTCTGTTACTAACGAGGTCACCCTCACACATCCTGTGACGAAATACA
  TyrArgLeuGlySerValThrAsnGluValThrLeuThrHisProValThrLysTyrIle

       430         440         450         460         470         480
TCGCCACTTGCATGCAAGCTGACCTTGAGGTCATGACCAGCACGTGGGTCCTAGCTGGGG
  AlaThrCysMetGlnAlaAspLeuGluValMetThrSerThrTrpValLeuAlaGlyGly

       490         500         510         520         530         540
GGGTCTTGGCAGCCGTCGCCGCGTATTGCCTGGCGACTGGGTGTGTCTCCATCATCGGCC
  ValLeuAlaAlaValAlaAlaTyrCysLeuAlaThrGlyCysValSerIleIleGlyArg

       550         560         570         580         590         600
GCTTGCACATCAATCAGCGAGCCGTCGTTGCACCAGACAAGGAGGTCCTTTATGAGGCTT
  LeuHisIleAsnGlnArgAlaValValAlaProAspLysGluValLeuTyrGluAlaPhe

       610         620         630         640         650         660
TTGATGAGATGGAGGAGTGTGCCTCTAAAGCGGCTCTCATTGAAGAGGGGCAGCGGATAG
  AspGluMetGluGluCysAlaSerLysAlaAlaLeuIleGluGluGlyGlnArgIleAla

       670         680         690         700         710         720
CCGAGATGCTGAAGTCCAAGATCCAAGGCTTATTGCAGCAAGCCTCTAAACAGGCCCAGG
  GluMetLeuLysSerLysIleGlnGlyLeuLeuGlnGlnAlaSerLysGlnAlaGlnAsp

       730         740         750         760         770
ACATACAACCCGCTGTGCAGCCTCATGGCCCAAGGTGGAGCAATTCTGGGC
  IleGlnProAlaValGlnProHisGlyProArgTrpSerAsnSerGly
```

Fig. 4

```
        10        20        30        40        50        60
CTGGTATGAACTTACGCCTGCTGAGACTACGGTGAGACTCCGGGCCTATTTCAACACGCC
TrpTyrGluLeuThrProAlaGluThrThrValArgLeuArgAlaTyrPheAsnThrPro

        70        80        90       100       110       120
CGGCCTGCCTGTGTGTCAAGACCACCTGGAATTCTGGGAGGCGGTCTTCACAGGTCTCAC
GlyLeuProValCysGlnAspHisLeuGluPheTrpGluAlaValPheThrGlyLeuThr

       130       140       150       160       170       180
ACACATCGATGCCCACTTCCTCTCCCAGACGAAGCAAGGAGGAGATAACTTTGCATATTT
HisIleAspAlaHisPheLeuSerGlnThrLysGlnGlyGlyAspAsnPheAlaTyrLeu

       190       200       210       220       230       240
AACAGCCTACCAGGCCACAGTCTGCGCTAGGGCAAAGGCTCCCCCTCCTTCGTGGGACGT
ThrAlaTyrGlnAlaThrValCysAlaArgAlaLysAlaProProProSerTrpAspVal

       250       260       270       280       290       300
GATGTGGAAGTGTTTGATTAGGCTCAAACCTACACTGACTGGTCCTACCCCCCTCCTGTA
MetTrpLysCysLeuIleArgLeuLysProThrLeuThrGlyProThrProLeuLeuTyr

       310       320       330       340       350       360
CCGCTTGGGTGCCGTGACCAACGAGGTTACCCTGACTCACCCCATGACGAAATATATCGC
ArgLeuGlyAlaValThrAsnGluValThrLeuThrHisProMetThrLysTyrIleAla

       370       380       390       400       410       420
CACTTGTATGCAAGCTGATCTTGAGATCATGACAAGCACATGGGTCTTGGCGGGGGGGT
ThrCysMetGlnAlaAspLeuGluIleMetThrSerThrTrpValLeuAlaGlyGlyVal

       430       440       450       460       470       480
GCTAGCCGCTGTGGCAGCTTACTGCCTAGCGACCGGCTGCATTTCCATCATTGGCCGCCT
LeuAlaAlaValAlaAlaTyrCysLeuAlaThrGlyCysIleSerIleIleGlyArgLeu

       490       500       510       520       530       540
TCACCTGAATGATCGGGTGGTCGTGACCCCTGATAAGGAAATTTTATATGAGGCCTTTGA
HisLeuAsnAspArgValValValThrProAspLysGluIleLeuTyrGluAlaPheAsp

       550       560       570       580       590       600
TGAGATGGAAGAGTGCGCCTCCAAAGCCGCCCTCATTGAGGAAGGGCAGCGGATGGCGGA
GluMetGluGluCysAlaSerLysAlaAlaLeuIleGluGluGlyGlnArgMetAlaGlu

       610       620       630
GATGCTGAAGTCTAAAATACAAGGCCTCTT
MetLeuLysSerLysIleGlnGlyLeu
```

Fig. 5a

```
        10        20        30        40        50        60
GGGATCAACCCTAACATCAGGACCGGAGTACGGACCGTGACCACCGGGGACTCCATCACC
GlyIleAsnProAsnIleArgThrGlyValArgThrValThrThrGlyAspSerIleThr

        70        80        90       100       110       120
TACTCCACTTATGGCAAGTTTATCGCAGATGGAGGTTGCGCACGTGGTGCCTATGACGTC
TyrSerThrTyrGlyLysPheIleAlaAspGlyGlyCysAlaArgGlyAlaTyrAspVal

       130       140       150       160       170       180
ATCATATGCGACGAATGCCATTCAGTGGACGCTACTACCATCCTTGGCATTGGAACAGTC
IleIleCysAspGluCysHisSerValAspAlaThrThrIleLeuGlyIleGlyThrVal

       190       200       210       220       230       240
CTTGACCAGGCTGAGACCGCAGGTGCCAGGCTAGTGGTTTTAGCCACAGCCACGCCACCC
LeuAspGlnAlaGluThrAlaGlyAlaArgLeuValValLeuAlaThrAlaThrProPro

       250       260       270       280       290       300
GGTACGGTAACAACTCCCCACGCTAACATAGAGGAGGTGGCCCTTGGTCACGAAGGCGAG
GlyThrValThrThrProHisAlaAsnIleGluGluValAlaLeuGlyHisGluGlyGlu

       310       320       330       340       350       360
ATTCCTTTTTATGGCAAGGCTATTCCCCTAGCTTTCATCAAGGGGGGCAGACACCTAATT
IleProPheTyrGlyLysAlaIleProLeuAlaPheIleLysGlyGlyArgHisLeuIle
```

Fig. 5b

```
       370       380       390       400       410       420
TTTTGCCATTCAAAGAAGAAGTGCGACGAGCTCGCAGCAGCCCTTCGGGGCATGGGTATC
PheCysHisSerLysLysLysCysAspGluLeuAlaAlaAlaLeuArgGlyMetGlyIle

       430       440       450       460       470       480
AATGCCGTTGCCTACTACAGGGGTCTCGACGTCTCCGTTATACCAACTCAAGGAGACGTG
AsnAlaValAlaTyrTyrArgGlyLeuAspValSerValIleProThrGlnGlyAspVal

       490       500       510       520       530       540
GTGGTTGTCGCCACCGATGCCCTAATGACTGGATACACCGGTGACTTTGACTCTGTCATC
ValValValAlaThrAspAlaLeuMetThrGlyTyrThrGlyAspPheAspSerValIle

       550       560       570       580       590       600
GACTGCAACGTTGCAGTCACTCAGATTGTTGACTTTAGCCTAGACCCAACTTTTACCATC
AspCysAsnValAlaValThrGlnIleValAspPheSerLeuAspProThrPheThrIle

       610       620       630       640       650       660
ACCACTCAAACCGTCCCTCAGGAGGCTGTCTCCCGTAGTCAACGTAGAGGGAGAACTGGG
ThrThrGlnThrValProGlnGluAlaValSerArgSerGlnArgArgGlyArgThrGly

       670       680       690       700       710       720
AGGGGGCGACTGGGCACTTACAGGTATGTCTCGTCAGGCGAGAGGCCGTCTGGGATGTTC
ArgGlyArgLeuGlyThrTyrArgTyrValSerSerGlyGluArgProSerGlyMetPhe

       730       740       750       760       770       780
GACAGCGTAGTACTCTGCGAGTGCTATGATGCCGGGGCAGCCTGGTACGAGCTTACACCT
AspSerValValLeuCysGluCysTyrAspAlaGlyAlaAlaTrpTyrGluLeuThrPro
```

Fig. 5c

```
       790       800       810       820       830       840
GCTGAGACCACAGTGAGACTCCGGGCTTATTTCAACACGCCCGGTTTGCCCGTGTGTCAA
AlaGluThrThrValArgLeuArgAlaTyrPheAsnThrProGlyLeuProValCysGln

       850       860       870       880       890       900
GACCACCTGGAGTTCTGGGAAGCGGTCTTCACAGGTCTCACGCACATTGATGCCCACTTC
AspHisLeuGluPheTrpGluAlaValPheThrGlyLeuThrHisIleAspAlaHisPhe

       910       920       930       940       950       960
CTCTCCCAGACAAAGCAAGGAGGAGACAACTTCGCGTATCTAACGGCCTACCAGGCCACA
LeuSerGlnThrLysGlnGlyGlyAspAsnPheAlaTyrLeuThrAlaTyrGlnAlaThr

       970       980       990      1000      1010      1020
GTGTGCGCTAGGGCAAAGGCCCCTCCTCCCTCGTGGGATGTGATGTGGAAATGTCTAGCT
ValCysAlaArgAlaLysAlaProProProSerTrpAspValMetTrpLysCysLeuAla

      1030      1040      1050      1060      1070      1080
AGGCTGAAGCCTACACTAATTGGTCCTACCCCCCTCCTGTACCGCTTGGGTGCCGTGACC
ArgLeuLysProThrLeuIleGlyProThrProLeuLeuTyrArgLeuGlyAlaValThr

      1090      1100      1110      1120      1130      1140
AACGAGGTTACCCTGACGCACCCCGTGACGAAATACATCGCCACGTGCATGCAAGTGAAC
AsnGluValThrLeuThrHisProValThrLysTyrIleAlaThrCysMetGlnValAsn

      1150      1160      1170      1180      1190      1200
CTCGAGATCATGACGAGCACATGGGTCCTAGCAGGGGGGGTGCTAGCCGCCGTGGCAGCT
LeuGluIleMetThrSerThrTrpValLeuAlaGlyGlyValLeuAlaAlaValAlaAla

      1210      1220      1230      1240      1250      1260
TACTGCCTGGCAACCGGCTGTGTTTCCATCATCGGCCGCCTACACCTGAATGATCAAGTG
TyrCysLeuAlaThrGlyCysValSerIleIleGlyArgLeuHisLeuAsnAspGlnVal

      1270      1280      1290      1300      1310      1320
GTTGTGACTCCTGACAAAGAAATCTTATATGAGGCCTTTGATGAGATGGAAGAATGCGCC
ValValThrProAspLysGluIleLeuTyrGluAlaPheAspGluMetGluGluCysAla

      1330      1340      1350      1360      1370      1380
TCCAAAGCCGCCCTCATTGAGGAAGGGCAGCGGATGGCGGAGATGCTCAAGTCTAAGATA
SerLysAlaAlaLeuIleGluGluGlyGlnArgMetAlaGluMetLeuLysSerLysIle

      1390      1400      1410      1420
CAAGGCCTCCTACAACAGGCCACAAGACAGGCCCAAGACATACAGC
GlnGlyLeuLeuGlnGlnAlaThrArgGlnAlaGlnAspIleGln
```

Fig. 6a

```
        10        20        30        40        50        60
CGCAGACATTCCAAGTGGCCCATCTGCACGCTCCCACTGGTAGCGGCAAGAGCACTAAGG
  GlnThrPheGlnValAlaHisLeuHisAlaProThrGlySerGlyLysSerThrLysVal

        70        80        90       100       110       120
TGCCGGCTGCATATGCGGCCCAAGGGTACAAGGTACTCGTCCTGAACCCGTCCGTTGCCG
  ProAlaAlaTyrAlaAlaGlnGlyTyrLysValLeuValLeuAsnProSerValAlaAla

       130       140       150       160       170       180
CCACTTTAGCCTTTGGGGCGTACATGTCTAAGGCACATGGTGTCGACCCTAACATCAGAA
  ThrLeuAlaPheGlyAlaTyrMetSerLysAlaHisGlyValAspProAsnIleArgThr

       190       200       210       220       230       240
CTGGGGTGAGGACCATCACCACGGGCGCTCCCATCACGTACTCCACCTATGGTAAGTTCC
  GlyValArgThrIleThrThrGlyAlaProIleThrTyrSerThrTyrGlyLysPheLeu

       250       260       270       280       290       300
TTGCCGACGGTGGTTGCTCTGGGGGCGCCTATGACATCATAATATGTGATGAGTGCCACT
  AlaAspGlyGlyCysSerGlyGlyAlaTyrAspIleIleIleCysAspGluCysHisSer

       310       320       330       340       350       360
CAACTGACTCGACATCCATCTTGGGCATCGGCACAGTCCTGGACCAAGCGGAGACGGCTG
  ThrAspSerThrSerIleLeuGlyIleGlyThrValLeuAspGlnAlaGluThrAlaGly
```

Fig. 6b

```
        370       380       390       400       410       420
GAGCGCGGCTCGTCGTGCTCGCTACCGCTACGCCTCCGGGATCGGTCACCGTGCCACATC
 AlaArgLeuValValLeuAlaThrAlaThrProProGlySerValThrValProHisPro

        430       440       450       460       470       480
CCAATATCGAGGAGGTGGCCCTGTCCACCACTGGAGAGATTCCCTTCTACGGCAAAGCTA
 AsnIleGluGluValAlaLeuSerThrThrGlyGluIleProPheTyrGlyLysAlaIle

        490       500       510       520       530       540
TCCCCATCGAGACAATCAAGGGGGGGAGGCATCTCATCTTCTGCCGTTCCAAGAAGAAGT
 ProIleGluThrIleLysGlyGlyArgHisLeuIlePheCysArgSerLysLysLysCys

        550       560       570       580       590       600
GTGACGAGCTCGCTGGAAAGCTGTCAGCCCTCGGAATCAACGCTGTAGCGTACTACCGGG
 AspGluLeuAlaGlyLysLeuSerAlaLeuGlyIleAsnAlaValAlaTyrTyrArgGly

        610       620       630       640       650       660
GTCTTGATGTATCCGTCATACCGACCAGCGGAGACGTCGTTGTCGTGGCAACAGACGCTC
 LeuAspValSerValIleProThrSerGlyAspValValValValAlaThrAspAlaLeu

        670       680       690       700       710       720
TAATGACGGGCTACACCGGTGACTTTGATTCAGTGATCGACTGCAATACATGTGTCACCC
 MetThrGlyTyrThrGlyAspPheAspSerValIleAspCysAsnThrCysValThrGln

        730       740       750       760       770       780
AGACAGTCGACTTCAGCTTGGACCCTACCTTCACCATTGAGACGACGACCGTGCCTCAAG
 ThrValAspPheSerLeuAspProThrPheThrIleGluThrThrThrValProGlnAsp

        790       800       810       820       830       840
ACGCGGTGTCACGCTCGCAGCGGCGAGGCAGAACTGGTAGGGGTAGAGGGGGCATATACA
 AlaValSerArgSerGlnArgArgGlyArgThrGlyArgGlyArgGlyGlyIleTyrArg

        850
GGTTTGTGACTCCAG
 PheValThrPro
```

Fig. 7

```
        10        20        30        40        50        60
GACGAGCTCGCCGCAAAGCTGTCAGGCCTCGGAGTCAATGCTGTGGCATACTACCGGGGT
AspGluLeuAlaAlaLysLeuSerGlyLeuGlyValAsnAlaValAlaTyrTyrArgGly

        70        80        90       100       110       120
CTCGATGTGTCTGTCATACCGACGAGCGGGGACGTCGTTGTTGTGGCAACAGACGCTCTA
LeuAspValSerValIleProThrSerGlyAspValValValValAlaThrAspAlaLeu

       130       140       150       160       170       180
ATGACGGGCTATACCGGCGACTTTGACTCGGTGATCGACTGCAATACATGTGTCACCCAA
MetThrGlyTyrThrGlyAspPheAspSerValIleAspCysAsnThrCysValThrGln

       190       200       210       220       230       240
ACAGTCGATTTCAGCTTGGACCCTACTTTCACCATTGAGACGACGACCGTGCCCCAAGAC
ThrValAspPheSerLeuAspProThrPheThrIleGluThrThrThrValProGlnAsp

       250       260       270       280       290       300
GCGGTGTCGCGCTCGCAGCGGCGAGGCAGGACTGGTAGGGGCAGGGTGGGCATATACAGG
AlaValSerArgSerGlnArgArgGlyArgThrGlyArgGlyArgValGlyIleTyrArg

       310
TTTGTGACTCCCGAG
PheValThrProGlu
```

Fig. 8a

```
        10        20        30        40        50        60
GTGATGAGCTCGCCGCAAAGCTCTCAAGCCTCGGACTCAACGCTGTAGCATATTACCGGG
   AspGluLeuAlaAlaLysLeuSerSerLeuGlyLeuAsnAlaValAlaTyrTyrArgGly

        70        80        90       100       110       120
GTCTTGATGTGTCCGTCATACCGACTAGTGGAGACGTCGTTGTCGTGGCAACAGACGCTC
   LeuAspValSerValIleProThrSerGlyAspValValValValAlaThrAspAlaLeu

       130       140       150       160       170       180
TAATGACGGGCTATACCGGCGACTTTGACTCAGTGATCGACTGTAACACATGTGTCACCC
   MetThrGlyTyrThrGlyAspPheAspSerValIleAspCysAsnThrCysValThrGln

       190       200       210       220       230       240
AGACAGTTGATTTCAGCTTGGATCCAACCTTCACCATTGAGACGACGACCGTGCCTCAAG
   ThrValAspPheSerLeuAspProThrPheThrIleGluThrThrThrValProGlnAsp

       250       260       270       280       290       300
ACGCGGTGTCGCGCTCGCAGCGGCGAGGTAGGACTGGCAGGGGCAGGGGCGGCATCTATA
   AlaValSerArgSerGlnArgArgGlyArgThrGlyArgGlyArgGlyGlyIleTyrArg

       310       320       330       340       350       360
GGTTTGTGACTCCAGGAGAACGGCCCTCGGGCATGTTCGATTCCTCGGTCCTGTGTGAGT
   PheValThrProGlyGluArgProSerGlyMetPheAspSerSerValLeuCysGluCys

       370       380       390       400       410       420
GTTATGACGCGGGCTGTGCTTGGTATGAGCTCACGCCCGCCGAGACCACGGTTAGGTTGC
   TyrAspAlaGlyCysAlaTrpTyrGluLeuThrProAlaGluThrThrValArgLeuArg

       430       440       450       460       470       480
GGGCTTACCTAAATACACCAGGGTTGCCCGTCTGCCAGGACCATCTGGAGTTCTGGGAGG
   AlaTyrLeuAsnThrProGlyLeuProValCysGlnAspHisLeuGluPheTrpGluGly

       490       500       510       520       530       540
GCGTCTTCACAGGCCTCACCCACATAGATGCCCATTTCTTGTCTCAGACTAAGCAGGCAG
   ValPheThrGlyLeuThrHisIleAspAlaHisPheLeuSerGlnThrLysGlnAlaGly
```

Fig. 8b

```
      550       560       570       580       590       600
GAGACAACTTTCCCTACCTGGTGGCATACCAAGCTACAGTGTGCGCCAGGGCTCAGGCTC
 AspAsnPheProTyrLeuValAlaTyrGlnAlaThrValCysAlaArgAlaGlnAlaPro

      610       620       630       640       650       660
CACCTCCATCGTGGGACCAAATGTGGAAGTGTCTCATACGGCTGAAACCTACGCTGCACG
 ProProSerTrpAspGlnMetTrpLysCysLeuIleArgLeuLysProThrLeuHisGly

      670       680       690       700       710       720
GGCCAACACCCCTGCTGTATAGGCTAGGAGCCGTCCAAAATGAGGTCACCCTCACACACC
 ProThrProLeuLeuTyrArgLeuGlyAlaValGlnAsnGluValThrLeuThrHisPro

      730       740       750       760       770       780
CCATAACCAAATTCATCATGGCATGCATGTCGGCTGATCTGGAGGTCGTCACCAGCACCT
 IleThrLysPheIleMetAlaCysMetSerAlaAspLeuGluValValThrSerThrTrp

      790       800       810       820       830       840
GGGTGCTGGTGGGCGGAGTCCTTGCAGCTCTGGCCGCATATCGCCTGACAACAGGCAGCG
 ValLeuValGlyGlyValLeuAlaAlaLeuAlaAlaTyrArgLeuThrThrGlySerVal

      850       860       870       880       890       900
TGGTCATCGTGGGTAGGATCATCTTGTCTGGGAGGCCGGCTGTCATTCCCGACAGGGAAG
 ValIleValGlyArgIleIleLeuSerGlyArgProAlaValIleProAspArgGluVal

      910
TCCTTTACCGG
 LeuTyrArg
```

Fig. 9

```
        10        20        30        40        50        60
CGACAACCGTGCCCCAAGACGCGGTGTCGCGCTCACAACGGCGGGTAGGACAGGTAGGG
 ThrThrValProGlnAspAlaValSerArgSerGlnArgArgGlyArgThrGlyArgGly

        70        80        90       100       110       120
GCAGGAGAGGCATCTACAGATTTGTGACTCCGGGAGAACGGCCCTCGGGCATGTTCGATT
 ArgArgGlyIleTyrArgPheValThrProGlyGluArgProSerGlyMetPheAspSer

       130       140       150       160       170       180
CTTCGGTCCTGTGTGAGTGCTATGACGCGGGCTGCGCTTGGATCGAGCTCACGCCCGCCG
 SerValLeuCysGluCysTyrAspAlaGlyCysAlaTrpIleGluLeuThrProAlaGlu

       190       200       210       220       230       240
AGACCTCAGTTAGGTTGCGGGCTTACCTAAATACACCAGGGTTGCCCGTCTGCCAGGACC
 ThrSerValArgLeuArgAlaTyrLeuAsnThrProGlyLeuProValCysGlnAspHis

       250       260       270       280       290       300
ACCTGGAATTCTGGGAGAGCGTCTTCACAGGCCTCACCCATATAGATGCCCACTTCTTGT
 LeuGluPheTrpGluSerValPheThrGlyLeuThrHisIleAspAlaHisPheLeuSer

       310       320       330       340       350       360
CCCAGACCAAGCAGGCAGGAGACAACTTCCCCTACCTGGTAGCATACCAAGCTACAGTGT
 GlnThrLysGlnAlaGlyAspAsnPheProTyrLeuValAlaTyrGlnAlaThrValCys

       370       380       390       400       410       420
GCGCCAGGGCCCAGGCTCCACCACCATCGTGGGATCAAATGTGGAAGTGTCTCATACGCC
 AlaArgAlaGlnAlaProProProSerTrpAspGlnMetTrpLysCysLeuIleArgLeu

       430       440       450       460       470       480
TGAAACCTACGCTACACGGGCCAACACCCCTGTTGTATAGGCTGGGAGCCGTCCAAAATG
 LysProThrLeuHisGlyProThrProLeuLeuTyrArgLeuGlyAlaValGlnAsnGlu

AGGTCACCC
 ValThr
```

Fig. 10a

```
1         10        20        30        40        50        60
GTGGTCTCCTGGGTGCCATCGTGGTCAGCCTAACGGGCCGCGACAAGAACCAGGTCGAGG
  GlyLeuLeuGlyAlaIleValValSerLeuThrGlyArgAspLysAsnGlnValGluG

          70        80        90        100       110
GGGAGGTTCAGGTGGTCTCCACCGCAACGCAATCTTTCCTGGCGACCTGCGTCAATGGCGT
lyGluValGlnValValSerThrAlaThrGlnSerPheLeuAlaThrCysValAsnGlyVa

        130       140       150       160       170
GTGTTGGACCGTCTACCATGGCGCCGGCTCGAAAACCCTGGCCGGCCCGAAGGGTCCAGTC
lCysTrpThrValTyrHisGlyAlaGlySerLysThrLeuAlaGlyProLysGlyProVal

       190       200       210       220       230
ACCCAAATGTACACTAATGTGGACCAGGACCTCGTCGGCTGGCCGGCGCCCTCCGGGGCGC
ThrGlnMetTyrThrAsnValAspGlnAspLeuValGlyTrpProAlaProSerGlyAlaA

      250       260       270       280       290
GGTCCTTGACACCATGCACCTGCGGCAGCTCGGACCTTTACTTGGTCACGAGGCATGCTGA
rgSerLeuThrProCysThrCysGlySerSerAspLeuTyrLeuValThrArgHisAlaAs

     310       320       330       340       350       360
TGTCATTCCGGTGCGCCGGCGGGGCGATAGCAGGGGGAGCCTGCTTTCCCCCAGGCCCCTC
pValIleProValArgArgArgGlyAspSerArgGlySerLeuLeuSerProArgProLeu

    370       380       390       400       410       420
TCCTACTTGAAGGGCTCCTCAGGTGGTCCACTGCTTTGCCCCTCGGGGCACATTGTGGGCA
SerTyrLeuLysGlySerSerGlyGlyProLeuLeuCysProSerGlyHisIleValGlyI

   430       440       450       460       470       480
TCTTCCGGGCTGCCGTGTGCACCCGGGGGGTTGCGAAGGCGGTGGACTTTGTACCTGTCGA
lePheArgAlaAlaValCysThrArgGlyValAlaLysAlaValAspPheValProValGl

  490       500       510       520       530       540
GTCTATGGAAACTACTATGCGGTCTCCGGTCTTCACGGATAATTCATCCCCCCCGGCCGTA
uSerMetGluThrThrMetArgSerProValPheThrAspAsnSerSerProProAlaVal

 550       560       570       580       590       600
CCGCAGACATTCCAAGTGGCCCATCTGCATGCCCCCACTGGCAGCGGCAAGAGCACTAAGG
ProGlnThrPheGlnValAlaHisLeuHisAlaProThrGlySerGlyLysSerThrLysV

610       620       630       640       650       660
TGCCGGCTGCATACGCAGCCCAGGGATACAAGGTACTCGTCCTGAACCCGTCCGTTGCCGC
alProAlaAlaTyrAlaAlaGlnGlyTyrLysValLeuValLeuAsnProSerValAlaAl

          680       690       700       710       720
CACCTTAGGTTTTGGAGCATATATGTCCAAGGCACATGGTGTCGACCCTAACATCAGGACT
aThrLeuGlyPheGlyAlaTyrMetSerLysAlaHisGlyValAspProAsnIleArgThr

         740       750       760       770       780
GGGGTAAGGACCATCACTACGGGCGCCCCCATTACATACTCCACCTATGGCAAGTTTCTTG
GlyValArgThrIleThrThrGlyAlaProIleThrTyrSerThrTyrGlyLysPheLeuA
```

Fig. 10b

```
     800          810          820          830          840
CCGACGGTGGTTGCTCCGGGGGCGCCTATGACATCATAATATGTGATGAGTGCCACTCAAC
laAspGlyGlyCysSerGlyGlyAlaTyrAspIleIleIleCysAspGluCysHisSerTh

    860          870          880          890          900
TGACTCGACTTCCATTTTGGGCATTGGCACGGTCCTGGACCAAGCGGAGACGGCTGGAGCG
rAspSerThrSerIleLeuGlyIleGlyThrValLeuAspGlnAlaGluThrAlaGlyAla

   920          930          940          950          960          970
CGGCTCGTCGTGCTCGCCACCGCTACGCCTCCAGGATCGGTCACTGTGCCTCATCCCAACA
ArgLeuValValLeuAlaThrAlaThrProProGlySerValThrValProHisProAsnI

  980          990          1000         1010         1020         1030
TCGAGGAGGTGGCCTTGTCCAGCACTGGAGAGATTCCCTTCTATGGCAAAGCCATCCCCAT
leGluGluValAlaLeuSerSerThrGlyGluIleProPheTyrGlyLysAlaIleProIl

1040         1050         1060         1070
TGAGACCATCAAGGGGGGAAGGCATCTCATTTTCTGCCAC
eGluThrIleLysGlyGlyArgHisLeuIlePheCysHis
```

*Fig. 11*

```
1        10          20          30          40          50          60
GTCGACCCCAATATTAGAACTGGGGTAAGGACCATCACCACGGGCGCTCCCATTACGTAT
ValAspProAsnIleArgThrGlyValArgThrIleThrThrGlyAlaProIleThrTyr

         70          80          90          100         110
TCTACCTATGGCAAATTCCTTGCCGACGGTGGTTGCTCTGGGGGCGCCTATGACATCATAA
SerThrTyrGlyLysPheLeuAlaAspGlyGlyCysSerGlyGlyAlaTyrAspIleIleI

       130         140         150         160         170
TCTGTGATGAGTGCCACTCAACTGACTCGACTTCCATCTTGGGTATCGGCACAGCCCTGGA
leCysAspGluCysHisSerThrAspSerThrSerIleLeuGlyIleGlyThrAlaLeuAs

      190         200         210         220         230
CCAAGCGGAGACGGCTGGAGCACGGCTTGTCGTGCTCGCCACCGCTACGCCTCCAGGGTCG
pGlnAlaGluThrAlaGlyAlaArgLeuValValLeuAlaThrAlaThrProProGlySer

     250         260         270         280
GTCACCGTGCCGCATCCCAACATCGAGGAGGTAGCCTTGCC
ValThrValProHisProAsnIleGluGluValAlaLeu
```

Fig. 12

```
1         10        20        30        40        50        60
GGACAACTCATCTCCCCCGGCGGTACCGCAGACATTCCAGGTGGCCCATCTACACGCTCC
 AspAsnSerSerProProAlaValProGlnThrPheGlnValAlaHisLeuHisAlaPr

        70        80        90        100       110
CACTGGCAGCGGCAAGAGCACTAAGGTGCCGGCTGCATATGCAGCCCAAGGGTACAAAGTA
oThrGlySerGlyLysSerThrLysValProAlaAlaTyrAlaAlaGlnGlyTyrLysVal

      130       140       150       160       170
CTCGTCCTGAACCCGTCCGTTGCCGCCACCTTAAGTTTCGGGGCGTATATGTCCAAGGCAC
LeuValLeuAsnProSerValAlaAlaThrLeuSerPheGlyAlaTyrMetSerLysAlaH

     190       200       210       220       230
ATGGTGTTGACCCTAATATCAGAACTGGGACAAGGACCATCACCACGGGCGCTCCCATCAC
isGlyValAspProAsnIleArgThrGlyThrArgThrIleThrThrGlyAlaProIleTh

    250       260       270       280       290
GTACTCCACCTATGGCAAGTTCCTTGCAGACGGTGGTTGCTCCGGAGGCGCCTATGACATC
rTyrSerThrTyrGlyLysPheLeuAlaAspGlyGlyCysSerGlyGlyAlaTyrAspIle

   310       320       330       340       350       360
ATAATATGCGATGAGTGCCACTCAACAGACTCGACTTCCATCTTAGGCATTGGTACGGTCC
IleIleCysAspGluCysHisSerThrAspSerThrSerIleLeuGlyIleGlyThrValL

  370       380       390       400       410       420
TGGACCAAGCGGAGACGGCTGGAGCGCGACTCGTCGTGCTCGCCACCGCTACGCCTCCAGG
euAspGlnAlaGluThrAlaGlyAlaArgLeuValValLeuAlaThrAlaThrProProGl

 430       440       450       460       470       480
ATCGGTCACTGTGCCACATCCCAACATCGAGGAGGTGGCCCTGTCCAACACTGGAGAGATT
ySerValThrValProHisProAsnIleGluGluValAlaLeuSerAsnThrGlyGluIle

490       500       510       520       530       540
CCCTTCTATGGCAAAGCCATCCCCATTGAGGCCATCAAGGGGGGGAGGCATCTCATTTTCT
ProPheTyrGlyLysAlaIleProIleGluAlaIleLysGlyGlyArgHisLeuIlePheC

550       560       570       580       590       600
GCCATTCTAAGAAGAAGTGTGATGAGCTCGCCACGAAGCTGTCGGCCCTCGGACTCAATGC
ysHisSerLysLysLysCysAspGluLeuAlaThrLysLeuSerAlaLeuGlyLeuAsnAl

610       620       630       640
TGTAGCGTACTACCGGGGTCTTGATGTGTCCG
aValAlaTyrTyrArgGlyLeuAspValSer
```

*Fig. 13*

```
1         10             20             30             40             50             60
CAGGCGAGAGGCCGACAGGGATGTTTGACAGCGTAGTGCTCTGTGAGTGCTATGATGCCG
  GlyGluArgProThrGlyMetPheAspSerValValLeuCysGluCysTyrAspAlaG

          70             80             90            100            110
GGGCCGCCTGGTACGAGCTTACGCCTGCTGAGACTACGGTGAGACTCCGGGCTTATTTCAA
lyAlaAlaTrpTyrGluLeuThrProAlaGluThrThrValArgLeuArgAlaTyrPheAs

       130            140            150            160            170
CACGCCCGGTTTGCCTGTATGTCAAGACCACCTAGAGTTCTGGGAAGCGGTCTTCACAGGT
nThrProGlyLeuProValCysGlnAspHisLeuGluPheTrpGluAlaValPheThrGly

      190            200            210            220            230
CTCACACACATTGATGCCCACTTCCTCTCCCAGACGAAGCAAGGAGGAGACAACTTTGCGT
LeuThrHisIleAspAlaHisPheLeuSerGlnThrLysGlnGlyGlyAspAsnPheAlaT

     250            260            270            280            290
ATCTAACGGCCTACCAGGCCACAGTATGCGCCAGGGCAAAGGCCCCCCCTCCTTCGTGGGA
yrLeuThrAlaTyrGlnAlaThrValCysAlaArgAlaLysAlaProProProSerTrpAs

    310            320            330            340            350            360
CGTGATGTGGAAGTGTCTAATCAGGCTCAAACCTACATTGACTGGTCCTACCCCCCTCCTG
pValMetTrpLysCysLeuIleArgLeuLysProThrLeuThrGlyProThrProLeuLeu

   370            380            390            400            410            420
TACCGCTTGGGTGCCGTGACTAACGAGGTTACCCTGACGCACCCCGTGACGAAATATATCG
TyrArgLeuGlyAlaValThrAsnGluValThrLeuThrHisProValThrLysTyrIleA

  430
CCACGT
laThr
```

Fig. 14

```
1         10        20        30        40        50        60
ATGGGCACGAATCCTAAACCTCAAAGAAAAACCAAAAGAAACACTAACCGTCGCCCACAA
MetGlyThrAsnProLysProGlnArgLysThrLysArgAsnThrAsnArgArgProGln

          70        80        90        100       110
GACGTTAAGTTTCCGGGCGGCGGCCAGATCGTTGGCGGAGTATACTTGTTGCCGCGCAGGG
AspValLysPheProGlyGlyGlyGlnIleValGlyGlyValTyrLeuLeuProArgArgG

      130       140       150       160       170
GCCCCAGATTGGGTGTGCGCGCGACAAGGAAGACTTCGAAGCGGTCCCAGCCACGTGGGGG
lyProArgLeuGlyValArgAlaThrArgLysThrSerLysArgSerGlnProArgGlyGl

    190       200       210       220       230
GCGCCGGCCCATCCCTAAAGATCGGCGCTCCACTGGCAAGTCCTGGGGGAAACCAGGATAC
yArgArgProIleProLysAspArgArgSerThrGlyLysSerTrpGlyLysProGlyTyr

   250       260       270       280       290
CCCTGGCCCCTATATGGGAATGAGGGACTCGGCTGGGCAGGGTGGCTTCTGTCCCCCCGAG
ProTrpProLeuTyrGlyAsnGluGlyLeuGlyTrpAlaGlyTrpLeuLeuSerProArgG

  310       320       330       340       350       360
GTTCCCGTCCCTCTTGGGGCCCCACTGACCCCCGGCATAGGTCGCGCAATGTGGGTAAGGT
lySerArgProSerTrpGlyProThrAspProArgHisArgSerArgAsnValGlyLysVa

CATC
lIle
```

Fig. 15a

```
1         10        20        30        40        50        60
CGCGCAACTTGGGTAAGGTCATCGATACCCTCACATGCGGCTTCGCCGACCTCATGGGGT
  ArgAsnLeuGlyLysValIleAspThrLeuThrCysGlyPheAlaAspLeuMetGlyT

         70        80        90        100       110
ACATTCCGCTTGTCGGCGCCCCCCTAGGGGGTGCTGCCAGGGCCCTGGCACATGGTGTCCG
yrIleProLeuValGlyAlaProLeuGlyGlyAlaAlaArgAlaLeuAlaHisGlyValAr

       130       140       150       160       170
GGTTCTGGAGGACGGCGTGAACTATGCAACAGGGAATTTGCCCGGTTGCTCTTTCTCTATC
gValLeuGluAspGlyValAsnTyrAlaThrGlyAsnLeuProGlyCysSerPheSerIle

      190       200       210       220       230
TTCCTCTTGGCTTTGCTGTCCTGTTTGACCATCCCAGCTTCCGCTTATGAGGTGCGCAACG
PheLeuLeuAlaLeuLeuSerCysLeuThrIleProAlaSerAlaTyrGluValArgAsnV

     250       260       270       280       290
TATCCGGGATATACCATGTCACGAACGACTGCTCCAACTCAAGTATTGTGTATGAGGCAGC
alSerGlyIleTyrHisValThrAsnAspCysSerAsnSerSerIleValTyrGluAlaAl

    310       320       330       340       350       360
GGACATGATCATGCATACCCCCGGGTGCGTGCCCTGCGTTCGGGAGAACAACTCCTCCCGT
aAspMetIleMetHisThrProGlyCysValProCysValArgGluAsnAsnSerSerArg

   370       380       390       400       410       420
TGCTGGGCAGCGCTCACTCCCACGTTAGCGGCCAGGAACACCAGCGTCCCCACTACGACAA
CysTrpAlaAlaLeuThrProThrLeuAlaAlaArgAsnThrSerValProThrThrThrI

  430       440       450       460       470       480
TACGACGGCATGTCGATTTGCTCGTTGGGGCGGCTGCTTTCTGCTCCGCTATGTACGTGGG
leArgArgHisValAspLeuLeuValGlyAlaAlaAlaPheCysSerAlaMetTyrValGl
```

Fig. 15b

```
490       500       510       520       530       540
GGATCTCTGTGGATCTGTCTTCCTCGTTTCCCAGCTGTTCACTTTCTCACCTCGTCGGCAT
yAspLeuCysGlySerValPheLeuValSerGlnLeuPheThrPheSerProArgArgHis

550       560       570       580       590       600
GAGACAGTACAGGACTGCAACTGCTCAATCTATCCCGGCCACTTGACAGGTCATCGCATGG
GluThrValGlnAspCysAsnCysSerIleTyrProGlyHisLeuThrGlyHisArgMetA

610       620       630       640       650       660
CTTGGGATATGATGATGAACTGGTCACCTACAACAGCCCTAGTGGTGTCGCATCTACTCCG
laTrpAspMetMetMetAsnTrpSerProThrThrAlaLeuValValSerHisLeuLeuAr

          680       690       700       710       720
GATCCCACAAGCTGTCATGGACATGGTGGCGGGGGCTCACTGGGGAGTCCTAGCGGGCCTC
gIleProGlnAlaValMetAspMetValAlaGlyAlaHisTrpGlyValLeuAlaGlyLeu

         740       750       760       770       780
GCCTACTATTCCATGGTGGGGAACTGGGCTAAGGTTTTGATTGTGATGCTACTCTTCGCCG
AlaTyrTyrSerMetValGlyAsnTrpAlaLysValLeuIleValMetLeuLeuPheAlaG

        800       810       820       830       840
GCGTTGACGGGACCACCTATGTGACAGGGGGGACGACAGGCCGCACCACCAGCTCGTTCGC
lyValAspGlyThrThrTyrValThrGlyGlyThrThrGlyArgThrThrSerSerPheAl

       860       870       880       890       900
ATCCCTCTTTACACTTGGGTCGCATCAGAAGGTCCAGCTTATAAATACCAATGGCAGCTGG
aSerLeuPheThrLeuGlySerHisGlnLysValGlnLeuIleAsnThrAsnGlySerTrp

      920       930
CACATCAACAGGACCGCC
HisIleAsnArgThrAla
```

Fig. 16

```
1         10          20          30          40          50          60
CGCCGGTATGAGACGGCGCAAGACTGCAATTGCTCACTCTATCCCGGTCACGTATCTGGT
ArgArgTyrGluThrAlaGlnAspCysAsnCysSerLeuTyrProGlyHisValSerGly

          70          80          90         100         110
CACCGCATGGCTTGGGATATGATGATGAACTGGTCACCTACAACGGCCCTAGTGGTATCGC
HisArgMetAlaTrpAspMetMetMetAsnTrpSerProThrThrAlaLeuValValSerG

        130         140         150         160         170
AGCTACTCCGGATCCCACAAGCCGTCGTGGACATGGTGGCGGGGGCCCACTGGGGAGTCCT
lnLeuLeuArgIleProGlnAlaValValAspMetValAlaGlyAlaHisTrpGlyValLe

       190         200         210         220         230
AGCGGGCCTTGCCTACTATTCCATGGTGGCGAACTGGGCTAAGGTCTTGGTTGTGATGCTA
uAlaGlyLeuAlaTyrTyrSerMetValAlaAsnTrpAlaLysValLeuValValMetLeu

      250         260         270         280         290
CTCTTTGCCGGCGTTGACGACGGGAAGACCACCGTGACGGGGGGGAGCGCAGCCTTCCAGT
LeuPheAlaGlyValAspAspGlyLysThrThrValThrGlyGlySerAlaAlaPheGlnS

     310         320         330         340         350         360
CCAGGAAGTTAGTGTCCTTCTTCTCACCAGGGCCGAAACAAAATATCCAGCTTGATAACAC
erArgLysLeuValSerPhePheSerProGlyProLysGlnAsnIleGlnLeuAspAsnTh

    370         380         390         400         410         420
CAACGGCAGCTGGCACATCAACAGGACTGCCCTGAATTGCAATGACTCCCTCCAAACTGGG
rAsnGlySerTrpHisIleAsnArgThrAlaLeuAsnCysAsnAspSerLeuGlnThrGly

   430         440         450         460         470         480
TTCATCGCTGCGCTGTTCTACGCGCACAAGTTCAATTCGTCCGGATGCCTAGAGCGCATGG
PheIleAlaAlaLeuPheTyrAlaHisLysPheAsnSerSerGlyCysLeuGluArgMetA

   490         500         510         520         530         540
CCAGCTGCCGCCCCATTGACAAGTTCGCGCAGGGGTGGGGTCCCATCACTCACGATACGCC
laSerCysArgProIleAspLysPheAlaGlnGlyTrpGlyProIleThrHisAspThrPr

550
TAAGATCCCGG
oLysIlePro
```

*Fig. 17*

```
1        10        20        30        40        50        60
GACACCGTATGGCATGGGACATGATGATGAACTGGTCGCCCACGGCTACCATGATTCTGG
  HisArgMetAlaTrpAspMetMetMetAsnTrpSerProThrAlaThrMetIleLeuA

         70        80        90       100       110
CGTATGTGATGCGCATCCCCGAGGTCGTCATGGACATCATTGGCGGGGCTCACTGGGGCGT
laTyrValMetArgIleProGluValValMetAspIleIleGlyGlyAlaHisTrpGlyVa

       130       140       150       160       170
CATGTTCGGCTTGGGCTATTTTTCTATGCAGGGGGCTTGGGCAAAAGTCGTTGTCATCCTT
lMetPheGlyLeuGlyTyrPheSerMetGlnGlyAlaTrpAlaLysValValValIleLeu

      190       200       210       220       230
CTGCTGGCCGCTGGGGTGGATGCGACTACCCTCAGCGTTGGGGGCTCTGCCGCGCACACCA
LeuLeuAlaAlaGlyValAspAlaThrThrLeuSerValGlyGlySerAlaAlaHisThrT

     250       260       270
CCGGCGGCCTTGTCGGCTTGTTCAAGCCTGGCG
hrGlyGlyLeuValGlyLeuPheLysProGly
```

Fig. 18

```
1        10        20        30        40        50        60
CGCTTGTCGGCGCCCCCCTAGGGGGTGCTGCCAGGGCCCTGGCACATGGTGTCCGGGTTC
  LeuValGlyAlaProLeuGlyGlyAlaAlaArgAlaLeuAlaHisGlyValArgValL

         70        80        90       100       110
TGGAGGACGGCGTGAACTATGCAACAGGGAATTTGCCCGGTTGCTCTTTCTCTATCTTCCT
euGluAspGlyValAsnTyrAlaThrGlyAsnLeuProGlyCysSerPheSerIlePheLe

       130       140       150       160       170
CTTGGCTTTGCTGTCCTGTTTGACCATCCCAGCTTCCGCTTATGAGGTGCGCAACGTATCC
uLeuAlaLeuLeuSerCysLeuThrIleProAlaSerAlaTyrGluValArgAsnValSer

      190       200       210       220       230
GGGATATACCATGTCACGAACGACTGCTCCAACTCAAGTATTGTGTATGAGGCAGCGGACA
GlyIleTyrHisValThrAsnAspCysSerAsnSerSerIleValTyrGluAlaAlaAspM

     250       260       270       280       290
TGATCATGCATACCCCCGGGTGCGTGCCCTGCGTTCGGGAGAACAACTCCTCCCGTTGCTG
etIleMetHisThrProGlyCysValProCysValArgGluAsnAsnSerSerArgCysTr

    310       320       330       340       350       360
GGCAGCGCTCACTCCCACGTTAGCGGCCAGGAACACCAGCGTCCCCACTACGACAATACGA
pAlaAlaLeuThrProThrLeuAlaAlaArgAsnThrSerValProThrThrThrIleArg

   370       380       390       400       410       420
CGGCATGTCGATTTGCTCGTTGGGGCGGCTGCTTTCTGCTCCGCTATGTACGTGGGGGATC
ArgHisValAspLeuLeuValGlyAlaAlaAlaPheCysSerAlaMetTyrValGlyAspL

  430       440       450       460       470       480
TCTGTGGATCTGTCTTCCTCGTTTCCCAGCTGTTCACTTTCTCACCTCGTCGGCATGAGAC
euCysGlySerValPheLeuValSerGlnLeuPheThrPheSerProArgArgHisGluTh

 490       500       510       520       530       540
AGTACAGGACTGCAACTGCTCAATCTATCCCGGCCACTTGACAGGTCATCGCATGGCTTGG
rValGlnAspCysAsnCysSerIleTyrProGlyHisLeuThrGlyHisArgMetAlaTrp

550       560       570       580       590       600
GATATGATGATGAACTGGTCACCTACAACAGCCCTAGTGGTGTCGCATCTACTCCGGATCC
AspMetMetMetAsnTrpSerProThrThrAlaLeuValValSerHisLeuLeuArgIleP

610       620       630       640       650       660
CACAAGCTGTCATGGACATGGTGGCGGGGGCCCACTGGGGAGTCCTAGCGGGCCTTGCCTA
roGlnAlaValMetAspMetValAlaGlyAlaHisTrpGlyValLeuAlaGlyLeuAlaTy

         680       690       700       710       720
CTATTCCATGGTGGGGAACTGGGCTAAGGTTTTGATTGTGATGCTACTCTTCGCCGGCGTT
rTyrSerMetValGlyAsnTrpAlaLysValLeuIleValMetLeuLeuPheAlaGlyVal

       740
GACGGGACCAC
AspGlyThr
```

NON-A NON-B HEPATITIS SPECIFIC ANTIGEN AND ITS USE IN HEPATITIS

This is a continuation of application Ser. No. 07/726,141 filed on Jul. 8, 1991 now abandoned.

The present invention relates to a novel DNA fragment encoding non-A non-B hepatitis-specific antigenic polypeptide which is found at the time of infection or onset of the non-A non-B hepatitis.

It also relates to an expression vector containing said DNA fragment, to a host cell transformed with said expression vector and to an expressed polypeptide obtained by culturing said host cell.

It further relates to a single stranded DNA sequence for PCR primer synthesized on the basis of a partial base sequence of said DNA fragment.

It also relates to the use of said expressed polypeptide and said single stranded DNA sequence in detection of the non-A non-B hepatitis virus.

BACKGROUND OF THE INVENTION

Non-A non-B hepatitis is an infectious disease which is caused by a masked virus other than hepatitis A and B viruses, but it is not easy to identify the virus because amounts of the virus-specific antigens are very small in a patient's body as well as amounts of anti-virus antibodies. Accordingly, diagnosis of non-A non-B hepatitis has been made serologically by the well-known method of "diagnosis by exclusion" wherein the increase in levels of alanine aminotransferase and aspartate aminotransferase is determined in a serum from a patient to make a diagnosis as to whether or not the hepatitis belongs to any of hepatitis A, hepatitis B, hepatitis D and other hepatitis symptoms caused by the known hepatopathy viruses such as CMV, EBV, etc, and if the result of diagnosis are not applicable to them, then this case is identified as non-A non-B hepatitis. It, however, is difficult to diagnose clinically as being non-A non-B hepatitis by such a method because there is no correlation between ALT value and non-A non-B hepatitis. Also, the lack of trustworthy means for the diagnosis is a serious problem, whereby a secondary infection with the non-A non-B hepatitis virus which may be caused by transfusing blood, especially, from a non-A non-B hepatitis virus-carrying healthy carrier into a person can hardly be prevented. Therefore, it has been assumed that the non-A non-B hepatitis occupies more than 90% of hepatitis cases caused by blood transfusion, corresponding to about one million of total patients a year.

In order to improve such situation and to raise a diagnostic accuracy of non-A non-B hepatitis, the Alter's panel in which standard sera are used has been developed by Alter at al at the NIH. Diagnostic materials which can pass the Alter's panel have been obtained by Arima et al [JIKKEN IGAKU (Japan), 1 (2), 196–201 (1989)] and by M. Houghton et al (WO 89/04669, PCT/JP90/500880) of Chiron Corp. almost simultaneously. Arima et al have screened sera from hepatitis patients using λgt11 (protein expression vector) which was derived from vital RNA from a non-A non-B hepatitis patient's serum. Also, Chiron Corp. have inoculated the patient's blood plasma into a chimpanzee to develop a chronic hepatitis, the blood plasma being obtained from the diseased animal which possesses the anti-virus antibodies with high titer, and then have screened in the same way as Arima et al. Chiron Corp.'s group has also succeeded in cloning almost the whole portion of the gene of a hepatitis C virus (HCV, designated by Chiron Corp.) and developed a kit for diagnosis which comprises an antigenic protein obtained by expressing a part of the HCV gene, In spite of such an effort, however, what is a causative agent of this disease, as well as numbers of the agent, has not yet been elucidated fully.

As described above, the two materials which can pass the Alter's panel have certainly led to a new technique of diagnosis replaced by said "diagnosis by exclusion", but screening patient's sera separately with the materials gives no results to be satisfied because both the materials from Arima et al and Chiron Corp. react with patient's sera in low positive ratios of about 60 to 80% and about 50 to 70%, respectively. In other words, in some cases, these materials would not react with sera from the patients who have been diagnosed clinically as non-A non-B hepatitis. A virus commonly have a function to cause mutation in their host cells for their surval, and thus the viral genes isolated from American patients by Chiron Corp. had been possibly mutated into various forms acclimated to chimpanzee as an infection intermediate.

Accordingly, a great demand has been directed to a large scale preparation of the reactive antigens which are capable of probing the non-A non-B hepatitis patients or carriers, and it is therefore necessary to construct effective cDNA clones through the isolation and purification of variously mutated viral RNA from many non-A non-B hepatitis patients.

In addition, in the case of sera which have failed in a trustworthy diagnosis using an antibody detection system, or sera which are collected immediately after infection and in which antibody titers do not yet raise, a gene amplification method (PCR method) may be useful for the confirmation of the disease because it can detect a trace amount of vital genes. Also, it is possible to clone the genes efficiently by the PCR method. However, since the PCR method is carried out using primers which are synthesized from a known gene sequence, it is not always possible to detect a gene of the non-A non-B hepatitis virus in a patient's fluid using primers which can be constructed on the basis of the HCV gene sequences determined by Chiron Corp., if a difference in mutation between said HCV gene of Chiron Corp. and said patient-carried viral gene is significant.

In consequence, to detect efficiently infection with the non-A non-B hepatitis virus, it is necessary to prepare at least one primer capable of detecting the viral gene with a high specificity. Such a purpose may be accomplished by isolating a great number of cDNA clones, synthesizing primers from relatively conserved regions among their gene sequences, and subjecting the resulting primers to screening through the PCR method.

SUMMARY OF THE INVENTION

This invention provides a novel DNA fragment which encodes a non-A non-B hepatitis-specific antigenic polypeptide derived from a non-structural or structural protein of the non-A non-B hepatitis virus, the polypeptide being formed at the time of the infection or onset of the non-A non-B hepatitis.

This invention also provides an expression vector containing the DNA fragment, a host cell transformed with the expression vector, an expressed polypeptide obtained by culturing the host cell, and a process for its production.

This invention further provides a primer for use in the detection of non-A non-B type hepatitis virus genes.

This invention further yet provides use of the expressed polypeptide or single stranded DNA primer in detection of the non-A non-B hepatitis virus, and a method for the detection of non-A non-B hepatitis virus genes and anti-non-A non-B hepatitis virus antibodies.

BRIEF DESCRIPTION OF THE DRAWINGS

FIG. 1 (Parts A–B) shows a nucleotide sequence of non-A non-B hepatitis-specific cDNA which is contained in a clone C11-7 and an amino acid sequence deduced from the sequence. These sequences are equivalent to SEQ ID NO. 1.

FIG. 2 shows a nucleotide sequence of non-A non-B hepatitis specific-cDNA which is contained in a clone C10-11 and an amino acid sequence deduced from the sequence. These sequences are equvalent to SEQ ID NO. 2.

FIG. 3 (Parts A–B) shows a nucleotide sequence of non-A non-B hepatitis specific-cDNA which is contained in a clone C10-13 and an amino acid sequence deduced from the sequence. These sequences are equivalent to SEQ ID NO. 3.

FIG 4. shows a nucleotide sequence of non-A non-B hepatitis specific-cDNA which is contained in a clone C10-14 and an amino acid sequence deduced from the sequence. These sequences are equivalent to SEQ ID NO. 4.

FIGS. 5 (Parts A–C) shows a nucleotide sequence of non-A non-B hepatitis-specific cDNA which is contained in a clone C10-15 and an amino acid sequence deduced from the sequence. These sequences are equivalent to SEQ ID NO. 5.

FIG. 6 (Parts A–B) shows a nucleotide sequence of non-A non-B hepatitis specific-cDNA which is contained in a clone C10-16 and an amino acid sequence deduced from the sequence. These sequences are equivalent to SEQ ID NO. 6.

FIG. 7 shows a nucleotide sequence of non-A non-B hepatitis specific-cDNA which is contained in a clone C10-17 and an amino acid sequence deduced from the sequence. These sequences are equivalent to SEQ ID NO. 7.

FIGS. 8 (Parts A–B) shows a nucleotide sequence of non-A non-B hepatitis-specific cDNA which is contained in a clone C10-18 and an amino acid sequence deduced from the sequence. These sequences ale equivalent to SEQ ID NO. 8.

FIG. 9 shows a nucleotide sequence of non-A non-B hepatitis-specific cDNA which is contained in a clone C10-19 and an amino acid sequence deduced from the sequence. These sequences are equivalent to SEQ ID NO. 9.

FIGS. 10 (Parts A–B) shows a nucleotide sequence of non-A non-B hepatitis-specific cDNA which is contained in a clone C10-21 and an amino acid sequence deduced from the sequence. These sequences are equivalent to SEQ ID NO. 10.

FIG. 11 shows a nucleotide sequence of non-A non-B hepatitis-specific cDNA which is contained in a clone C10-22 and an amino acid sequence deduced from the sequence. These sequences are equivalent to SEQ ID NO. 11.

FIG. 12 shows a nucleotide sequence of non-A non-B hepatitis-specific cDNA which is contained in a clone C10-23 and an amino acid sequence deduced from the sequence. These sequences are equivalent to SEQ ID NO. 12.

FIG. 13 shows a nucleotide sequence of non-A non-B hepatitis-specific cDNA which is contained in a clone C10-35 and an amino acid sequence deduced from the sequence. These sequences are equivalent to SEQ ID NO. 13.

FIG. 14 shows a nucleotide sequence of non-A non-B hepatitis-specific cDNA which is contained in a clone C11-C21 and an amino acid sequence deduced from the sequence. These sequences are equivalent to SEQ ID NO. 14.

FIG. 15 (Parts A–B) shows a nucleotide sequence of non-A non-B hepatitis-specific cDNA which is contained in a clone C10-E12 and an amino acid sequence deduced from the sequence. These sequences are equivalent to SEQ ID NO. 15

FIG. 16 shows a nucleotide sequence of non-A non-B hepatitis-specific cDNA which is contained in a clone C10-E13 and an amino acid sequence deduced from the sequence. These sequences are equivalent to SEQ ID NO. 16.

FIG. 17 shows a nucleotide sequence of non-A non-B hepatitis-specific cDNA which is contained in a clone C10-E24 and an amino acid sequence deduced from the sequence. These sequences are equivalent to SEQ ID NO. 17.

FIG. 18 shows a nucleotide sequence of non-A non-B hepatitis-specific cDNA which is contained in a clone C10-E15 and an amino acid sequence deduced from the sequence. These sequences are equivalent to SEQ ID NO. 18.

DETAILED DESCRIPTION OF THE INVENTION

Figure 19:
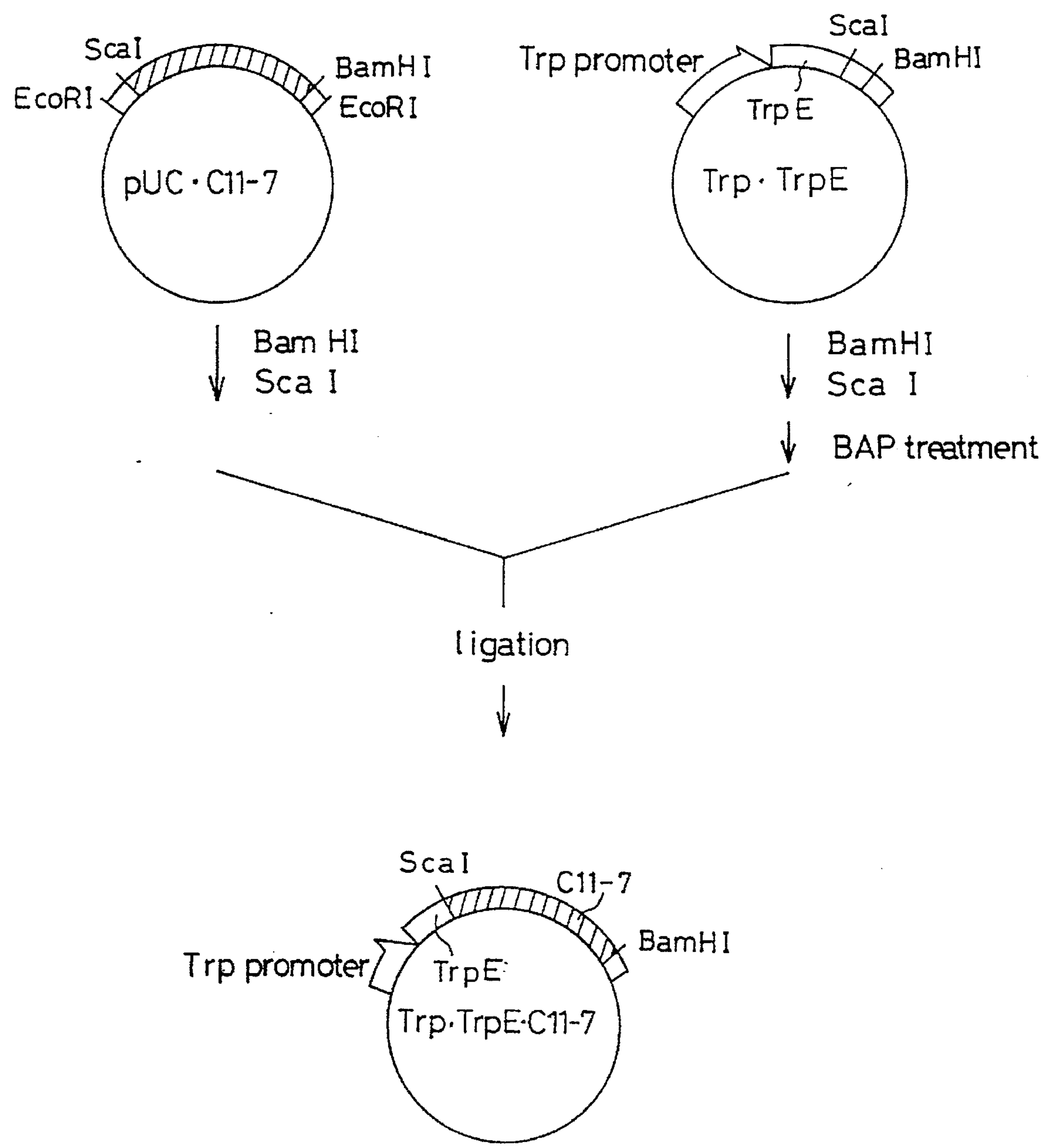
FIG. 19 shows a flow chart for the construction of an expression plasmid Trp·TrpE·C11-7.

Many aspects and advantages of the present invention will be made apparent to those skilled in the art by the following detailed description about preferred embodiments of the invention.

The present invention provides a specified DNA fragment comprising a base sequence which encodes a non-A non-B hepatitis-specific antigenic polypeptide derived from a non-structural or structural protein of the non-A non-B type hepatitis virus.

The preparation of the DNA fragment of the present invention is characterized in that variously mutated genes of pathogenic viruses were directly collected from a fresh blood plasma pool of a number of non-A non-B hepatitis patients. More particularly, the preparation comprises the steps in which the total RNA including non-A non-B hepatitis virus RNA is isolated from the blood plasma pool, cDNAs are synthesized based on the isolated RNA by the well-known random primer method, and then the cDNA obtained is incorporated into λ phage to prepare a cDNA library. The cDNA library is subsequently immunoscreened using sera from a non-A non-B hepatitis patient to obtain DNA fragments of interest. Thereafter, using the resulting DNA Thereafter, using the resulting DNA fragments as probe, cDNA libraries obtained from the blood plasma from several chronic non-A non-B hepatitis patients were subjected to hybridization assay in order to isolate cDNA which has a homology different from the known counterparts and which is specific for the non-A non-B hepatitis patient.

Such a process makes it possible to provide the viral antigens which are markedly useful for the diagnosis of non-A non-B hepatitis patients carrying the variously mutated viruses and for the improvement of detection accuracy of the hepatitis viruses contained in blood for transfusion which was collected from many latent carriers carrying non-A non-B type hepatitis viruses.

The following describes the present invention in detail with regard to the preparation of cDNA library, isolation and sequencing of DNA fragments, expression and isolation of polypeptides, and their application to diagnosis of non-A non-B hepatitis using enzyme-linked immunosorbent assay (ELISA) or PCR method.

Preparation of cDNA Library

Firstly, cell debris is removed from each of freshly collected blood plasma samples of several non-A non-B hepatitis patients by centrifugation and the resulting supernatant is again subjected to centrifugation at a higher rotation speed to obtain a pellet. The pellet is subjected to an equilibrium density gradient centrifugation using cesium trifluoroacetate to isolate total RNA as a precipitate, and the total RNA is purified by phenol/chloroform extraction and ethanol precipitation.

By the method of Gubler and Hoffman using random primers, cDNA is synthesized from the above RNA fraction. The cDNA is methylated by treating it with a DNA methylase (for example, EcoRI methylase), ligated with a DNA linker (for example, EcoRI linker) or DNA adapter (for example, EcoRI adapter), and then cloned into a cloning vector such as λ phage (for example, λgt10 or λgt11) to prepare a cDNA library.

Isolation and Sequencing of DNA Fragments

Next, *Escherichia coli* is infected with the λ phage cDNA library and cultured on an agar plate to form plaques. These plaques are transferred on a nitrocellulose filter, and subjected to blocking followed by immunoscreening using a non-A non-B hepatitis serum in order to detect positive clones. Alternatively, to improve efficiency of the screening, each positive clone obtained is cloned into a cloning vector such as plasmid and a $^{32}$P-labeled DNA probe is prepared by random primer technique, and then positive plaques are detected from the aforementioned cDNA library using the probe. 15, C10-16, C10-17, C10-18, C10-19, C10-21, C10-22, C10-23, C10-35, C11-C21, C10-E12, C10-E13, C10-E24 and C10-E15.

A cDNA sample is obtained from each λ phage DNA of 18 clones in a traditional manner and digested with appropriate restriction enzymes such as EcoRI and BamHI. Each cDNA fragment obtained is purified by agarose gel electrophoresis, incorporated into a sequencing vector (M13 phage), and then subjected to the dideoxy chain termination method [Sanger et al; *Proc. Natl. Acad. Sci.*, USA, 74, 5463 (1977)] in order to determine a base sequence of each cDNA fragment.

Nucleotide sequences of these clones and deduced amino acid sequences are shown in FIGS. 1 to 18 and in a Sequence Listing which will be described later as SEQ ID NOs. 1 to 18. That is, the SEQ ID NOs. 1 to 18 respectively represent the nucleotide and deduced amino acid sequences determined from clones C11-7, C10-11, C10-13, C10-14,C10-15, C10-16, C10-17, C10-18, C10-19, C10-21, C10-22, C10-23, C10-35, C11-C21, C10-E12, C10-E13, C10-E24 and C10-E15. Also, the base pair (BP) number of their DNA fragments is 763 BF, 615 BP, 771 BP, 630 BP, 1426 BP, 855 BP, 315 BP, 911 BP, 489 BP, 1076 BP, 284 BP, 641 BP, 432 BP, 369 BP, 932 BP, 559 BP, 276 BP and 742BP, respectively.

All the 18 clones contained continuous open reading frames but not termination codons.

Analysis of genomic RNA has revealed that hepatitis C virus (HCV) is a class of virus similar to the genus Flavivirus such Analysis of genomic RNA has revealed that hepatitis C virus (HCV) is a class of virus similar to the genus Flavivirus such as Japanese encephalitis virus [*Protein, Nucleic Acid and Enzyme* (Japan), 35 (12), 2117–2127 (1990)]. From the comparison of homology between the reported gene and polypeptide of Flavivirus and those of the present invention, it was found that clones C11-C21, C10-E12, C10-E13, C10-E24 and C10-E15 encode a structural protein of the non-A non-B type hepatitis virus. More particuarly, clone C11-C12 is a gene which encodes the core of non-A non-B hepatitis virus, and clones C10-E12, C10-E13, C10-E24 and C10-E15 are genes encoding a region between the latter half of the virus core and the env, or a region downstream from the env. Other clones were found to be genes encoding non-structural proteins of the virus.

The nucleotide sequences of the above 18 clones and the amino acid sequences translated along the open reading frames showed homologies with those of hepatitis C virus (HCV) reported by Houghton et al (EP-A-318,216, 1988). Thus, clones C11-7, C10-16, C10-17, C10-18, C10-19, C10-21, C10-22 and C10-23 showed relatively high homologies with HCV: 80 to 82% homology at nucleic acid level and 91 to 94% at amino acid level. In addition, these clones showed more higher homologies with the sequence J1 reported by Miyamura et al. (*Nuc. Aci. Res.*, 17, 10367–10372, 1989): 85 to 95% homology at nucleic acid level and 87 to 100% at amino acid level. These clones were classified as group 1 because of high homology in their overlapped portion. On the contrary, clones C10-11, C10-13, C10-14, C10-15 and C10-35 showed low homologies when compared to the nucleotide and amino acid sequences of HCV and J1, i.e., 69 to 70% homology at nucleic acid level and 75 to 80% at amino acid level. They were therefore classified as group 2.

In addition, when the 369 BP nucleotide and deduced 123-amino acid sequences, indicated as SEQ ID NO. 14, for the C11-C21 clone encoding a structural protein of the virus were compared with the portions overlapped with HCV reported by Houghton et al (WO 90/11089), a nucleic acid homology of 81.8% and an amino acid homology of 87% were found. Also, when compared with HCV clones, HC-J1 and HC-J4, obtained from a Japanese patient (Okamoto et al.; *Japan J. Exp. Med.*, 60, 3, p. 167–177, 1990), homologies of 82.1% and 82.7% at nucleic acid level and 87.8% and 89.4% at amino acid level were shown. Since the same regions among the reported three clones (HCV by Houghton et al. and HC-J1 and HC-J4 by Okamoto et al.) have high homologies of 92.1 to 97.6% at nucleic acid level and 95.5 to 96.7% at amino acid level, it has been found that the clone C11-C21 obtained by the present inventors has a certain distance from the reported clones in terms of homology and therefore is a different group of viral gene therefrom. The remaining 4 clones, C10-E12, C10-E13 and C10-E15, showed homologies of 83 to 93% at nucleic acid level and 82 to 95% at amino acid level when compared with the HCV, HC-J1 and HC-J4, while C10-E24 showed around 63% of homology at nucleic acid level and around 60% of homology at amino acid level.

However, no homology was found either at nucleic acid level or amino acid level, when the DNA fragments of the present invention were compared with any DNA fragment encoding non-A non-B hepatitis antigens which have been disclosed in Japanese Patent Application Laying-Open (KOKAI) Nos. 89/2576 and 89/124387.

Consequently, the clones C10-11, C10-13, C10-14, C10-15, C10-35, C11-C21, and C10-E24 have low homologies with the reported clones both at nucleic acid and amino acid levels. Other clones are also distiguishable from the reported clones.

Therefore, the present invention provides a DNA fragment comprising a base sequence which encodes a non-A non-B hepatitis-specific antigenic polypeptide, said polypeptide consisting of the whole or a part of the amino acid sequence which is encoded in the open reading frame and represented by any one of the SEQ ID NOs. 1 to 18.

Of course, the base sequences according to the present invention may include any other base sequence which comprises other codons corresponding to each amino acid.

Among the aforementioned clones, C11-7, C10-11, C10-13, C10-14, C10-15, C10-16, C10-17, C10-18 and C10-19 were transformed into *E. coli* HB101 strain and deposited on Jul. 6, 1990 with Fermentation Research Institute, Agency of Industrial Science and Technology, 1-3 Higashi 1-chome, Tsukuba-shi, Ibaraki-ken, 305, Japan, respectively as *E. coil* HB101/C11-7 (Accession Number: FERM P-11589), *E. coli* HB101/ C10-11 (FERM P-11581), *E. coli* HB101/C10-13 (FERM P-11582), *E. coli* HB101/C10-14 (FERM P-11583), *E. coli* HB101/C10-15 (FERM P-11584), *E. coli* HB101/ C10-16 (FERM P-11585), *E. coli* HB101/C10-17 (FERM P-11586), *E. coli* HB101/C10-18 (FERM P-11587) and *E. coli* HB101/C10-19 (FERM P-11588). These depositions were subsequently converted on Jun. 13, 1991 to an international deposition under the Budapest Treaty at the same international depository authority, under the following new Accession Numbers:

| *E. coli* HB101 | Accession No. (FERM BP-) |
|---|---|
| Clone C11-7 | 3442 |
| Clone C10-11 | 3434 |
| Clone C10-13 | 3435 |
| Clone C10-14 | 3436 |
| Clone C10-15 | 3437 |
| Clone C10-16 | 3438 |
| Clone C10-17 | 3439 |
| Clone C10-18 | 3440 |
| Clone C10-19 | 3441 |

Also, clones C11-C21, C10-E12, C10-E13, C10-E24 and C10-E15 were transformed into *E. coli* JM109 strain and deposited on Dec. 11, 1990 with Fermentation Research Institute, Agency of Industrial Science and Technology, the same address, respectively under Accession Numbers FERM P-11892, FERM P-11894, FERM P-11895, FERM P-11896 and FERM P-11897. These depositions were also subsequently converted on Jun. 17, 1991 for clone C11-C12 and on Jun. 13, 1991 for other clones to an international deposition under the Budapest Treaty in the same way. The following new Accession Numbers were given:

| *E. coli* JM109 | Accession No. (FERM BP-) |
|---|---|
| Clone C11-C21 | 3450 |
| Clone C10-E12 | 3444 |
| Clone C10-E13 | 3445 |
| Clone C10-E24 | 3446 |
| Clone C10-E15 | 3447 |

As described in the foregoing, the DNA fragments according to the present invention are different from any other prior DNA fragment. Though non-A non-B hepatitis virus is generally divided into two classes, namely groups 1 and 2, on the basis of the comparison of homology between the clones encoding a non-structural reagion of the hepatitis virus, there is a possibility of existing an intermediate group or even a third group because the virus is very susceptible to mutation in its host cells. It is accordingly difficult to correctly diagnose all the non-A non-B hepatitis patients using an antigen protein prepared from only one kind of DNA fragment. In order to overcome such a problem and to improve an efficiency of the diagnosis, it is necessary to establish such a useful process for the preparation of DNA that a number of effective clones can easily be obtained, and to use several types of clones in combination in diagnosis

Expression of non-A non-B Hepatitis Specific Antigenic Polypeptide

The present invention also provides an expression vector which is constructed by introducing the above-mentioned DNA fragment into a cloning site downstream of a promoter gene in a vector.

Any conventional vector such as plasmid, phage or the like can be used. An expression vector may be constructed by the well-known techniques in the art. The following describes processes for constructing the expression vectors of the invention.

Construction of Expression Plasmid Trp·TrpE·C11-7

A flow chart for the construction of the expression plasmid Trp·TrpE·C11-7 is shown in FIG. 19.

Firstly, a plasmid pUC·C11-7 DNA obtained by incorporating the clone C11-7 into pUC119 is digested with restriction enzymes BamHI and ScaI, and the resulting BamHI-ScaI fragment is isolated by agarose gel electrophoresis and then purified by a glass powder technique. Separately from this, an expression vector Trp·TrpE DNA is digested with BamHI and ScaI, treated with a bacterial alkaline phosphatase (BAP), and then extracted with phenol. The aqueous layer obtained is subsequently subjected to ethanol precipitation to obtain a treated vector DNA. By connecting the vector DNA with the aforementioned C11-7 DNA fragment in the presence of T4 DNA ligase, the expression plasmid Trp·TrpE·C11-7 is obtained in which the DNA encoding the non-A non-B hepatitis-specific antigen is located downstream of a promoter so that transcription of the DNA can be controlled by the promoter.

Construction of Expression Plasmid Trp·TrpE·C11-C21

Figure 20:
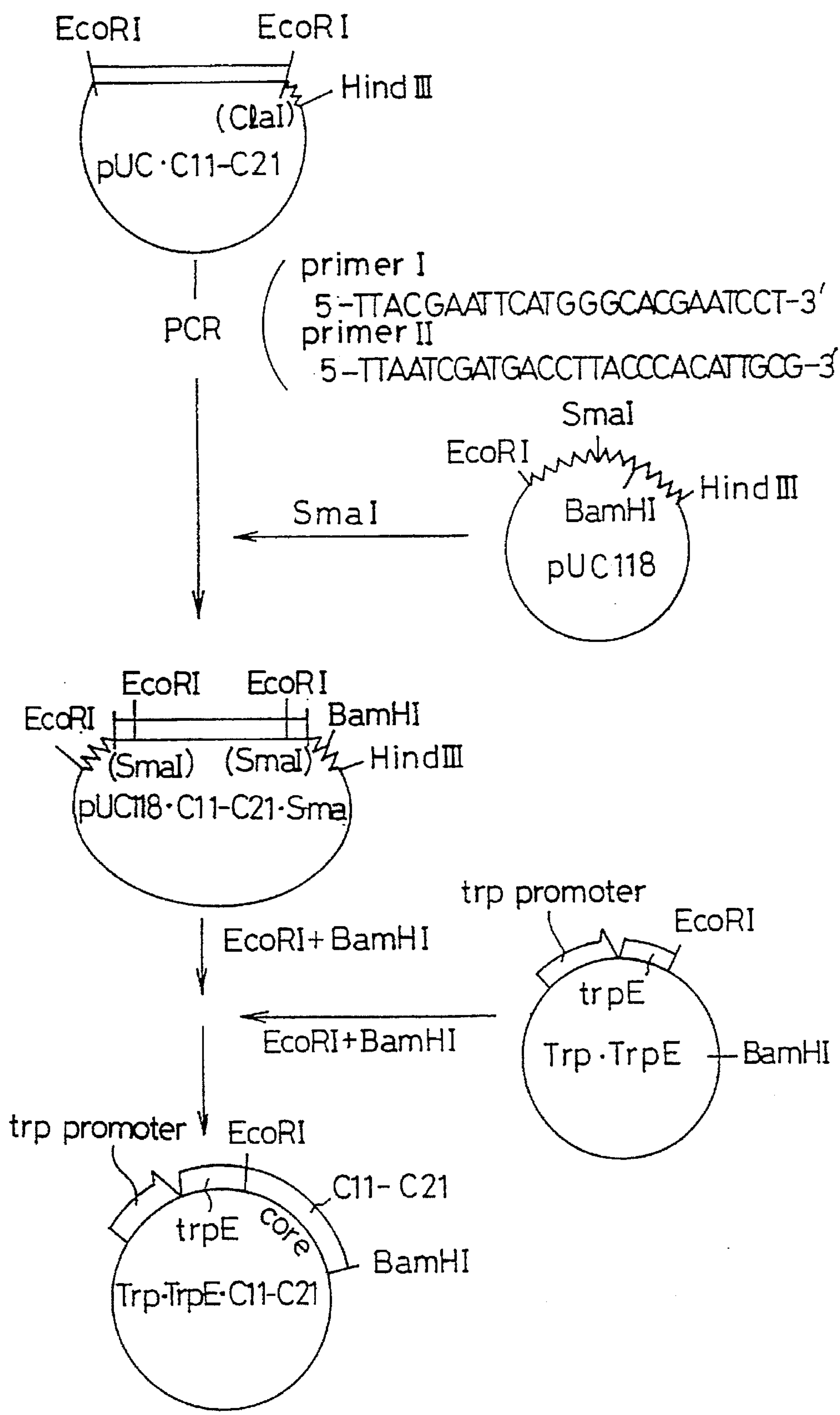
FIG. 20 shows a flow chart for the construction of an expression plasmid Trp·TrpE·C11-C21.

A flow chart for the construction of the expression plasmid Trp·TrpE·C11-C21 is shown in FIG. 20.

Firstly, a DNA fragment containing a stop codon in its 3' terminal is prepared from a plasmid pUC·C11-C21 DNA which is obtained by incorporating the C11-C21 clone into pUC119, by a gene amplification method (PCR) using two primers (5'-TTACGAATTCATGGGCACGAATCCT-3' (SEQ ID NO:23) and 5'-TTAATCGATGACCTTACCCACATTGCG-3' (SEQ ID NO:24)). By ligating the thus-prepared DNA fragment with pUC118 which is predigested with SmaI, a plasmid pUC118·C11-C21·Sma is obtained. This plasmid is then digested with EcoRI and BamHI, and the resulting DNA fragment is isolated by agarose gel electrophoresis and then purified by glass powder technique. Separately from this, an expression vector Trp·TrpE DNA (Japanese Patent Application No. 90/180889) is digested with BamHI and EcoRI, treated with a bacterial alkaline phosphatase (BAP), and then extracted with phenol. The aqueous layer obtained is subsequently subjected to ethanol precipitation to obtain a treated vector DNA. By ligating the vector DNA with the aforementioned C11-C21 DNA fragment by the action of T4 DNA ligase in a ligation buffer solution, the expression plasmid Trp·TrpE·C11-C21 is obtained in which the DNA-encoded polypeptide from a structural protein of the non-A non-B hepatitis virus is located downstream of a promoter so that transcription of the DNA can be controlled by the promoter.

Other clones can also be made into corresponding expression plasmids by treating each clone with appropriate restriction enzymes and introducing the treated fragment into an expression vector.

When a procaryote is used as the host cell, a promoter eligible for use in the present invention may be selected from promoters originated from *E. coli*, phage and the like, such as tryptophan synthase operon (trp), lactose operon (lac), λ phage $P_L$, λ phage $P_R$ and the like. When an eucaryote such as yeast is used as the host cell, promoters for 3-phosphoglycerate kinase and other glycolysis-related enzymes (Holland et al; *Biochemistry,* 17: 4900, 1978) may be useful. Though not always required, a transcription termination element may preferably be located in the expression vector.

The vector may further contain a marker sequence, such as an ampicillin or tetracycline resistance gene, which makes it possible to effect a phenotype selection in transformed cells.

The present invention also provides a transformant which is obtained by introducing the expression vector of the invention into a host cell. Microorganisms used commonly in this field, such as *E. coli, B. subtilis*, a yeast strain and the like, may be used as a host cell.

Transformation may be effected by any usually used means for the incorporation of an expression vector into host cells. When a bacterium (for example, *E. coli*) is used as host cell, a direct incorporation technique with the use of calcium chloride (Mandel, M. and Higa, A; *J. Mol. Bio.,* 53, 159–162, 1970) may be employed.

In addition, the polypeptide of the present invention may be produced by inoculating and culturing a suitable host cell carrying the expression vector in an appropriate medium such as ampicillin-containing 2YT medium and then propagating expression cells by subculturing them in an ampicillin-containing phosphate medium.

Production and Purification of Recombinant non-A non-B Hepatitis-Specific Antigenic Polypeptide The present invention also provides a process for producing a non-A non-B hepatitis-specific antigenic polypeptide, which comprises the following steps of:

- constructing a replicable expression vector having inserted therein a DNA fragment of the present invention;
- obtaining a transformant by introducing said expression vector into a host cell;
- producing said recombinant polypeptide by culturing said transformant under such conditions that said DNA fragment is expressed; and
- recovering said recombinant polypeptide.

The crude polypeptide product from host cells may be purified by disintegration of the host cells, for example by ultrasonic disintegration, subjecting the disintegrated cells to centrifugation to obtain an insoluble fraction containing a fused polypeptide between TrpE as signal peptide and a polypeptide encoded by cDNA synthesized from a non-A non-B hepatitis virus RNA, extracting the fused polypeptide in a soluble form with a urea-containing buffer, and then purifying obtained by such a expression process, said polypeptide consisting of the whole or part of the amino acid sequence represented by any one of the SEQ ID NOs. 1 to 18.

The term "recombinant non-A non-B hepatitis-specific antigenic polypeptide" as used herein is intended to include a polypeptide itself which is obtained by expressing in a vector a DNA fragment encoding a non-A non-B hepatitis-specific antigenic polypeptide, and a fused polypeptide obtained by fusing said polypeptide with other peptide such as a signal peptide.

Application to Diagnosis of non-A non-B Hepatitis

Figure 21:
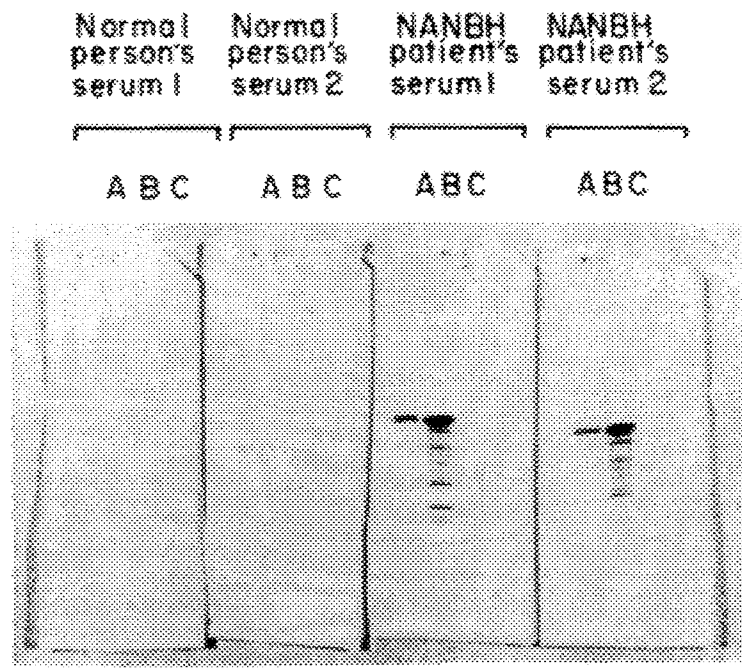
FIG. 21 is a photograph showing the results of western blotting analysis of an expressed product, TrpE·C11-7, with serum from a normal person or non-A non-B hepatitis patient, wherein the antigens used are a purified antigen in A, an extract of expressed cells in B, and an extract of non-expressed cells in C.
Figure 22:
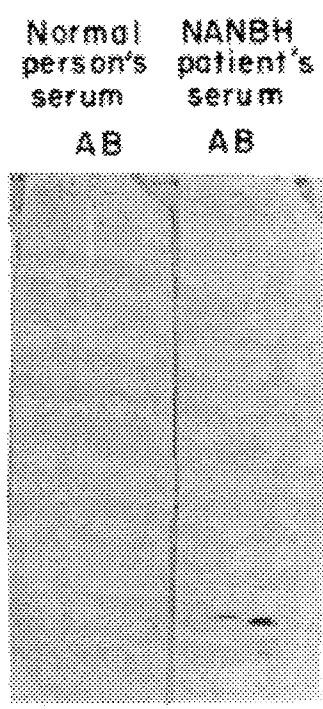
FIG. 22 is a photograph showing the results of western blotting of an expressed product, TrpE·C11-C21, with sera (A, B) from two normal persons or non-A non-B hepatitis patients.

The expressed polypeptide of the present invention was subjected to SDS-polyacrylamide gel electrophoresis and then allowed to perform antigen-antibody reaction with each of two serum samples from normal persons or non-A non-B hepatitis patients by means of western blotting. As a result, this polypeptide reacted strongly with only the patient's sera as shown in FIGS. 21 and 22. It was therefore confirmed that the expressed polypeptide functions as a non-A non-B hepatitis-specific antigen.

Accordingly, the present invention also provides a method for immunological detection to detect an antibody directed against the non-A non-B hepatitis virus antigen ,which comprises the following steps of:

Accordingly, the present invention also provides a method for immunological detection to detect an antibody directed against the non-A non-B hepatitis virus antigen, which comprises the following steps of:

- incubating a sample possibly containing an anti-non-A non-B hepatitis virus antibody together with at least one recombinant non-A non-B hepatitis-specific antigen polypeptide of the present invention under such conditions that the antigen is capable of reacting immunologically with the antibody; and
- detecting an antigen-antibody complex.

Figure 23:
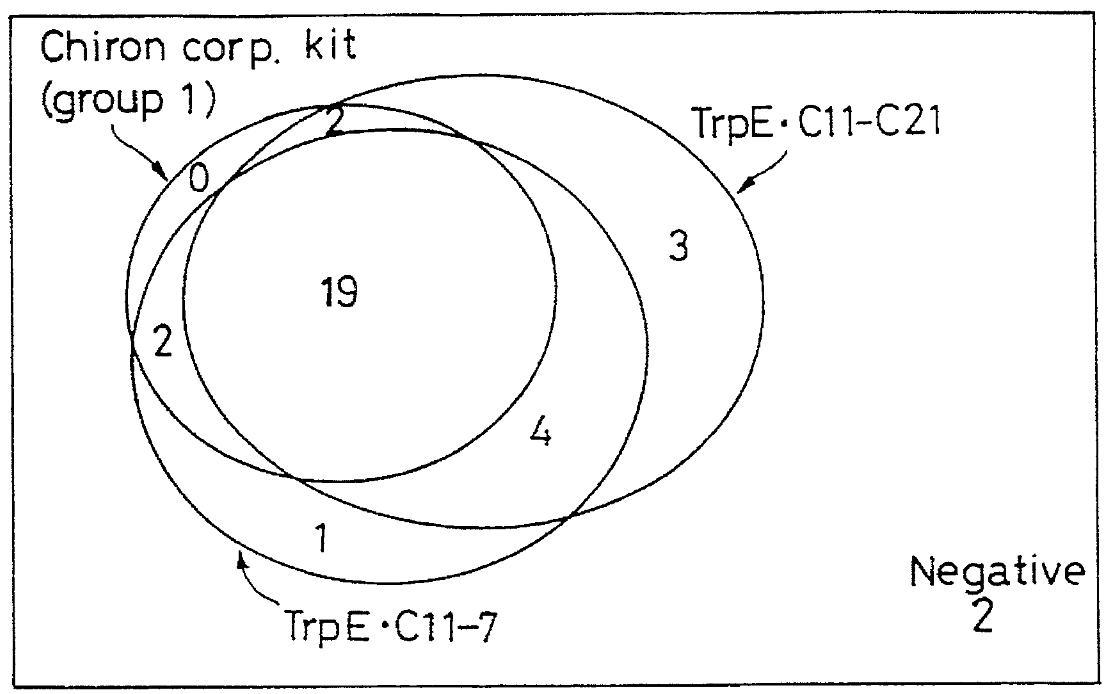
FIG. 23 is a graphical representation of the positive numbers determined by ELISA in Table 4.

Diagnostic effects (positiveness) of the expressed polypeptide TrpE·C11-C21 obtained by expressing the expression plasmid Trp·TrpE·C11-C21, another expressed polypeptide TrpE·C11-7 obtained by expressing the corresponding expression plasmid Trp·TrpE·C11-7, and an assay kit of Chiron Corp. (ORTHO HCV Ab ELISA kit) were examined by the conventional enzyme immunoassay through the reaction of the above expressed antigens with a serum sample from a patient who has been diagnosed clinically as being non-A non-B hepatitis. As the results, positiveness of the kit of Chiron Corp. was found to be 69.7% (23/33 cases) while the TrpE·C11-7 which belongs to group 1 showed a positiveness of 78.8% (26/33 cases). In the case of the expressed polypeptide TrpE·C11-C21, it showed a positiveness of 84.8% (28/33 cases) which is higher than the case of the Chiron's kit. When the expressed polypeptide TrpE·C11-7 as a member of group 1 and the TrpE·C11-C21 as a member of group 2 were used in combination, the positiveness increased to 93.9% (30/31 cases; see Table 1 and FIG. 23).

Therefore, according to an embodiment of the present invention, there is provided a combination of the group 1 and group 2-relating expressed polypeptides as a hepatitis-specific antigen polypeptide for use in the immunological detection.

The present invention further provides a method for gene amplification which comprises amplifying a non-A non-B hepatitis virus gene using sense and/or antisense sequence synthesized on the basis of the DNA sequences of the present invention.

As the synthetic base sequence for PCR primer, the following single strand DNA sequences may be employed:

5'-GGATACACCGGTGACTTTGA-3' (sense, SEQ ID NO. 19);

5'-TGCATGCACGTGGCGATGTA-3' (antisense, SEQ ID NO. 20);

5'-GATGCCCACTTCCTCTCCCA-3' (sense, SEQ ID NO. 21); and

5'-GTCAGGGTAACCTCGTTGGT-3' (antisense, SEQ ID NO. 22), said sequences being sense or antisense of the partial base sequence represented by the SEQ ID NO. 5 for the former two primers and by the SEQ ID NOs. 2, 4, 5 or 13 for the latter two primers. These specified primers are also within a scope of the invention.

The single stranded DNA sequences may be synthesized by the usual methods such as phosphorous acid method, phosphotriester method, solid phase method and the like, though the use of a DNA synthesizer is most convenient.

When used as a PCR primer, the above single stranded DNA sequences show higher specificity for the group 2 virus genes than for the group 1 virus genes (see Tables 2 and 3).

Therefore, the present invention also provides a method for detecting the genes from the non-A non-B type hepatitis virus in a fluid sample such as serum, which comprises the following steps of:

isolating RNA from the sample, synthesizing cDNA by treating the obtained RNA with a reverse transcriptase, subjecting the obtained cDNA to polymerase chain reaction using at least one the above-mentioned primer;

detecting an amplified non-A non-B type hepatitis virus gene.

The present invention further provides use of the expressed polypeptides or single stranded DNA sequences for PCR primer of the present invention in the detection of the non-A non-B hepatitis virus.

The following examples will be given to describe the present invention in more detail, but it is not intended to limit the invention thereby.

EXAMPLE 1

Preparation of cDNA Library from Blood Plasma of non-A non-B Hepatitis Patient A cDNA library was prepared using λgt10 and λgt11 phages after preparing an RNA fraction in the following manner from fresh blood plasma pools obtained from several Japanese patients of chronic stage non-A non-B hepatitis.

Five liter of blood plasma was diluted with the equal volume of 50 mM Tris-HCl (pH 8.0) containing 1 mM EDTA, cell debris in the diluted sample was removed by centrifugation at 3,500 g for 20 minutes and then the resulting supernatant was again subjected to centrifugation at 45,000 rpm (about 100,000 g) for 4 hours at a temperature of 4° C. to obtain pellet. The pellet was dissolved, according to the conventional procedure, in 6M guanidium thiocyanate as a protein denaturating agent, layered over a solution of cesium trifluoroacetate, and then subjected to centrifugation using Beckman SW50 rotor at 33,000 rpm for 18 hours at a temperature of 20° C. The resulting pellet was dissolved in 10 mM Tris-HCl (pH 7.5) containing 1 mM EDTA and extracted twice with a solvent system of 1:1 phenol:chloroform, afterwhich the organic layer was mixed with 1/10 volume of 5M NaCl and 2.5 volumes of ethanol. After allowing to stand the mixture for 2 hours at −20° C., it was centrifuged at 15,000 g for 20 minutes and the pellet was then dissolved in diethylpyrocarbonate-treated water to use as an RNA sample.

In accordance with the method of Gubler and Hoffman, cDNA was synthesized from the thus obtained RNA sample by means of random primer technique using a commercially available kit (from Amersham or BRL). The cDNA was subsequently treated with EcoRI methylase, ligated with an EcoRI linker or an EcoRI adapter and then cloned into the EcoRI site of λgt10 and λgt 11 phages. The cDNA library thus prepared contained $10^6$ to $10^7$ PFU of recombinant phages in average.

EXAMPLE 2

Isolation of non-A non-B Hepatitis-Specific cDNA

An attempt was made to isolate cDNA specific for non-A non-B hepatitis from the cDNA library prepared in Example 1, by immunoscreening and hybridization assay.

Firstly, immunoscreening of λgt11 library was carried out using two serum samples from non-A non-B hepatitis patients which are negative for HBc and HBs antibodies and which contain antibodies specific for the hepatitis-causing virus. Immunoscreening was performed in the usual way by examining specific reaction of a β-galactosidase-fused recombinant peptide with a serum sample of non-A non-B hepatitis (to be referred to as "NANBH" herein after) patient.

Cells of *E. coli* Y1090 strain were mixed with λgt11 cDNA library at a predetermined ratio, plated on an agar medium at an appropriate density, and then incubated at 43° C. for 3 hours to form plaques. Next, the agar plate was covered with a Hybond-C nitrocellulose filter which has been soaked with 10 mM IPTG and the filter-covered plate was incubated again at 37° C. for 3 hours to induce expression. Subsequently, the nitrocellulose filter was subjected to blocking using 3% gelatin solution, reacted with a serum sample of NANBH patient overnight at 4° C., and then, after washing, reacted with a peroxidase-labeled anti-human IgG (goat antibody). A positive signal was found when the resulting filter was reacted with a mixture of diaminobenzidine and $H_2O_2$. This clone, C11-7, did not react with HBc and HBs antibodies.

Next, in order to improve efficiency of the screening, the clone C11-7 was re-cloned into pUC119 and made into a probe by random primer method. Using the probe, λgt10 cDNA library was screened by means of hybridization assay. Screening was carried out according to the conventional method by plating $5\times10^4$ PFU of recombinant phages with *E. coli* C-600 hfl(−) on an L-plate (150 mm dish). When plaques appeared after overnight incubation of the plate at 37° C., the plate was stored at 4° C. for 1 hour and thereafter the plate was covered with a Hybond-N filter for a period of 30 seconds. The resulting filter was superposed for 1 minute on a filter prewetted with a denaturating solution (0.5M NaOH and 1.5M NaCl), soaked for 5 minutes in a neutralizing solution (0.5M Tris-HCl pH 7.0 and 1.5M NaCl), washed with 2×SSC, and then dried. The filter was subjected to UV-crosslinking by exposing it to UV rays (304 nm) for 2 minutes. Thereafter, as described below, the resulting filter was subjected to screening by hybridization assay using a $^{32}$P-labeled DNA probe which has been prepared by random primer method from the C11-7 clone obtained by immunoscreening with a serum from NANBH patient.

The filter was incubated overnight at 65° C. in 1×SSC, washed twice with 1×SSC at 65° C. (10 minutes for each) and then subjected to autoradiography at −70° C. for the detection of positive plaques. Each positive plaque was transferred into SM buffer and used as a phage stock. Clones obtained were used as marker probe to carry out a series of screening. As the results, 13 clones in total were isolated and designated as C10-11, C10-13, C10-14, C10-15, C10-16, C10-17, C10-18, C10-19, C10-21, C10-22, C10-23 and C10-35.

EXAMPLE 3

Selective Isolation of Group 2 non-A non-B Hepatitis-Specific cDNA

A blood plasma sample which can react only with C10-14 clone was obtained by subjecting fresh blood plasma of a Japanese patient in a chronic phase of the non-A non-B hepatitis to an ELISA-based screening system, using expressed products of the group 1 cDNA clone C11-7 and the group 2 cDNA clone C10-14 isolated in Examples 1 and 2. This blood plasma sample was subjected to a gene amplification method (PCR method) using well preserved primers of group 1 and those of group 2. PCR method was carried out using Gene Amp™ (DNA Amplification Reagent Kit, Perkin Elmer Cetus) under conditions of: DNA denaturation, 95° C. for 1.5 minutes; annealing, 55° C. for 2 minutes; and DNA synthesis, 70° C. for 3 minutes. Blood plasma samples in which gene amplification was found only with the use of the group 2 primers under these conditions were pooled for further use. An RNA fraction was prepared from one liter of this fresh blood plasma sample in the same manner as in Example 1, and a cDNA library (referred to as "cDNA library A" hereinafter) was constructed using λgt10 and λgt11 phages. The cDNA library A contained $10^6$ to $10^7$ PFU of recombinant phages in average.

On the other hand, a cDNA library B was constructed using λgt10 phage from five liters of fresh blood plasma samples which have been collected as starting material from several patients of non-A non-B hepatitis and have not been subjected to the ELISA/PCR method, in the same manner as described above. The cDNA library B also contained $10^6$ to $10^7$ PFU of recombinant phages in average.

Cloning of non-A non-B hepatitis-specific cDNA from cDNA library A was carried out by immunoscreening in the same manner as in Example 2, and a positive plaque (clone C11-C21) was obtained. The clone C11-C21 showed no positive reaction with HBc and HBs antibodies.

In order to improve efficiency of the screening, the thus obtained clone C11-C21 was re-cloned into pUC119, digested with restriction enzymes, and then made into a $^{32}$P-labeled probe by random primer labeling method in the same manner as in Example 2. Using the probe obtained, the cDNA library B was screened by hybridization assay. After a series of the screening efforts, 4 clones were isolated and named C10-E12, C10-E13, C10-E24 and C10-E15.

EXAMPLE 4

Sequencing of non-A non-B hepatitis-Specific cDNA

*E. coli* cells were infected with the λgt11 or λgt10 phage of each of the 18 clones obtained in Examples 2 and 3 to recover respective phage in a large quantity. DNA was extracted from the phage by the conventional alkali method, digested with a restriction enzyme EcoRI, BamHI or KpnI, and the resulting DNA fragments were purified by agarose gel electrophoresis. Separately from this, sequencing vectors mp18 and mp19 of M13 phage (Messing, J.; *Methods in Enzymology,* 101, 20–78) or pUC118 and pUC119 (Vieira, J. and Messing, J.; *Methods in Enzymology,* 153, 3–11) were digested with a restriction enzyme EcoRI, BamHI or KpnI to obtain linear vector fragments. The cDNA fragment and the vector DNA were ligated together using T4 ligase in a buffer solution, and the resulting reaction product was incorporated into *E. coli* HB1011 or JM109 strain by transformation or transfection. Resulting *E. coli* cells were cultured and DNA was recovered by alkali method. Nucleotide sequence of the DNA obtained was determined according to the dideoxy chain termination method of Sanger et al.

The nucleotide sequences of clones C10-11, C10-13, C10-14, C10-15, C10-16, C10-17, C10-18, C10-19, C10-21, C10-22, C10-23, C10-35, C10-C21, C10-E12, C10-E13, C10-E24 and C10-E15 and the amino acid sequences deduced from these nucleotide sequences are shown in a sequence table as SEQ ID NOs. 1 to 18 and also in FIGS. 1 to 18.

On the basis of the comparison of homologies among these sequences and the nucleotide and deduced amino acid sequences disclosed by Houghton et al.(WO89/04669, PCT/JP90/500880) and Miyamura et al(*Nuc. Aci. Res.,* 17, 10367–10372(1989)), clones C11-7, C10-17, C10-18, C10-19, C10-21, C10-22 and C10-23 obtained in Example 2 were classified as group 1 clone as defined hereabove while clones C10-11, C10-13, C10-14, C10-15 and C10-35 were classified as group 2 clones. Everyone of these 13 clones encoded non-structural protein of the non-A non-B type hepatitis virus. Moreover, clone C10-C21 in Example 3 was classified as group 2 from the comparison of homology with the sequences described by Houghton et al (WO90/11089) and Okamoto et al(*Japan J. Exp.Med.,* 60, 3, pp.167–177 (1990)), but classification of the clones C10-E12, C10-E13, C10-E24 and C10-E15 in Example 3 is not still clear. However, it was found that these 5 clones encode the structural protein of non-A non-B hepatitis virus from the comparison of homology with the reported genome of Flavivirus (*Protein, Nucleic Acid and Enzyme* (Japan), 35 (12), 2117–2127 (1990)).

EXAMPLE 5

Expression and Purification of Polypeptide Encoded by non-A non-B Type Hepatitis Virus cDNA (i) Construction of Expression Plasmid Trp·TrpE·C11-7:

One of the clones isolated, C11-7, was expressed as a fused polypeptide with TrpE in *E. coli* under the control of Trp promoter(see FIG. 19).

Firstly, 1 μg of a plasmid pUC·C11-7 DNA which has been obtained by incorporating the C11-7 clone into pUC119 was digested by incubating it at 37° C. for 1 hour in 20 μl of a restriction enzyme reaction solution [150 mM NaCl, 6 mM Tris-HCl (pH 7.9), 6 mM $MgCl_2$, 15 units of BamHI enzyme and 15 units of ScaI enzyme]. Thereafter, a BamHI-ScaI fragment of about 700 bp was obtained by subjecting the resulting reaction solution to 0.8% agarose gel electrophoresis, and the fragment was purified by glass powder method (Gene Clean™, Bio-101).

One μg of Trp·TrpE DNA which is an expression vector was digested by incubating it at 37° C. for 1 hour in 20 μl of a reaction solution [150 mM NaCl, 6 mM Tris-HCl (pH 7.5), 6 mM $MgCl_2$, 15 units of BamHI enzyme and 15 units of ScaI enzyme]. After adding 39 μl of water, the resulting reaction solution was heat-treated at 70° C. for 5 minutes, mixed with 1 μl (250 U/μl) of a bacterial alkaline phosphatase (BAP) and then incubated at 37° C. for 1 hour. The reaction solution was subsequently extracted with phenol, the aqueou layer was subjected to ethanol precipitation followed by drying of the precipitate. One μg of the BamHI-ScaI-treated vector DNA obtained and the above C11-7 DNA fragment was added to 5 μl of 10×ligase buffer [660 mM Tris-HCl (pH 7.5), 66 mM $MgCl_2$, 100 mM dithiothreitol and 1 mM ATP] and 1 μl of T4 DNA ligase (350 U/μl), and water was then added to the mixture to 50 μl of the final volume. Thereafter, the thus prepared mixture was incubated overnight at 16° C. to complete ligation.

*E. coli* HB101 strain was transformed with 10 μl of the resulting reaction solution. Competent *E. coli* strain for use in the transformation was prepared by calcium chloride technique [Mandel, M. and Higa, A.; *J. Moi. Biol.*, 53, 159–162 (1970)]. The transformed *E. coli* strain cells were spread on an LB-plate (1% trypton, 0.5% yeast extracts, 0.5% NaCl and 1.5% agar) containing 25 μg/ml of ampicillin and incubated overnight at 37° C. One loopful of each colony grown on the plate was transferred into a liquid LB medium containing 25 μg/ml of ampicillin and cultured overnight at 37° C. Cells in 1.5 ml of the cultured medium were collected by centrifugation, and Miniprep of plasmid DNA was carried out by alkali method (Maniatis et al; *Molecular Cloning: A Laboratory Manual*, 1982). One μg of the plasmid DNA obtained was digested at 37° C. for 1 hour in 20 μl of a reaction solution [150 mM NaCl, 6 mM Tris-HCl (pH 7.5), 6 mM $MgCl_2$, 15 units of BamHI and 15 units of ScaI]. Thereafter, the digested solution was subjected to agarose gel electrophoresis to obtain an expression plasmid Trp·TrpE·C11-7 which can produce the 700 bp BamHI-ScaI fragment. This plasmid was transformed into *E. coli* HB101 strain and deposited on Jul. 6, 1990 with Fermentation Research Institute, 1-3 Higashi 1-chome, Tsukuba-shi, Ibaraki-ken, 305, Japan, under the Accession Number FERM P-11590 (named *E. coli* HB101/Trp·TrpE·C11-7). This deposition was subsequently converted on Jun. 13, 1991 to an international deposition under Budapest Treaty at the same international depository authority, under the new Accession Number FERM BP-3443.

(ii) Expression and Purification of Polypeptide Encoded by Clone C11-7:

*E. coli* HB101 strain transformed with the expression plasmid Trp·TrpE·C11-7 was inoculated into 3 ml of a liquid 2YT medium (1.6% trypton, 1% yeast extracts and 0.5% NaCl) containing 50 μg/ml of ampicillin and cultured at 37° C. for 9 hours. One ml portion of the cultured broth was inoculated into 100 ml of a liquid M9-CA medium (0.6% $Na_2HPO_4$, 0.5% $KH_2PO_4$, 0.5% NaCl, 0.1% $NH_4Cl$, 0.1 mM $CaCl_2$, 2 mM $MgSO_4$, 0.5% casamino acid and 0.2% glucose) containing 50 μg/ml of ampicillin and cultured at 37° C. for 21 hours. A 18-ml portion of the resulting culture broth was then inoculated into 1.2 l of the M9-CA medium and cultured at 37° C. When turbidity at $OD_{600}$ of the culture broth reached 0.3, indole acrylate was added to a final concentration of 40 mg/l, and the culturing was continued for additional 16 hours. Cells collected from the final culture broth by centrifugation were suspended in 20 ml of buffer A [50 mM Tris-HCl (pH 8.0), 1 mM EDTA and 30 mM NaCl] and the cell suspension was again subjected to centrifugation to obtain 2.6 g of expressed cells. The thus obtained cells were suspended in 10 ml of the buffer A, disintegrated by ultrasonic treatment, and then subjected to centrifugation to obtain an insoluble fraction containing a fused polypeptide of TrpE with a polypeptide which is encoded by the non-A non-B type hepatitis virus cDNA. The fused polypeptide in the insoluble fraction was solubilized and extracted using 10 ml of the buffer A containing 9M urea. Thereafter, the solubilized extract was subjected to an S-Shepharose ion exchange column chromatography with an NaCl gradient of from 0M to 0.5M to purify the fused polypeptide.

(iii) Construction of Expression Plasmid Trp·TrpE·C11-C21:

The clone C11-C21 was expressed as a fused polypeptide with TrpE in *E. coli* under the control of a promoter (see FIG. 20).

Firstly, 1 ng of plasmid pUC·C11-C21DNA which has been obtained by incorporating C11-C21 clone into pUC119 was subjected to PCR method using two primers (5'-TTACGAATTCATGGGCACGAATCCT-3' (SEQ ID NO:23) and 5'-TTAATCGATGACCTTACCCACATTGCG-3' (SEQ ID NO:24)). PCR method was carried out using Gene Amp™ kit (DNA Amplification Reagent Kit, Perkin Elmer Cetus) under reaction conditions of: DNA denaturation, 95° C. for 1.5 minutes; annealing, 50° C. for 2 minutes; and DNA synthesis, 70° C. for 3 minutes. DNA fragments thus obtained were separated by 0.8% agarose gel electrophoresis and purified by glass powder technique. Separately from this, pUC118 was digested with a restriction enzyme SmaI and then ligated with the DNA fragment obtained by PCR method in a buffer solution containing T4 ligase to obtain a plasmid pUC118·C11-C21·Sma. One μg of the plasmid DNA obtained was digested at 37° C. for 1 hour in a restriction enzyme reaction solution [150 mM NaCl, 6 mM Tris-HCl (pH 7.9), 6 mM $MgCl_2$, 15 units of EcoRI enzyme and 15 units of BamHI enzyme]. Thereafter, the resulting reaction mixture was subjected to 0.8% agarose gel electrophoresis to isolate an EcoRI-BamHI fragment of about 380 bp which was then purified by glass powder technique (Gene Clean™, Bio-101).

Next, ligation and transformation were carried out substantially in the same manner as in the aforementioned procedure (i) except that restriction digestion of the expression vector Trp·TrpE DNA was carried out using EcoRI and BamHI instead of BamHI and ScaI. Thereafter, an expression plasmid Trp·TrpE·C11-C21 which can produce the EcoRI-BamHI fragment of about 380 bp was selected by agarose gel electrophoresis purification. This plasmid was transformed into *E. coli* HB101 strain and deposited on Dec. 11, 1990 with Fermentation Research Institute, Agency of Industrial Science and Technology, the same address, under the Accession Number FERM P-11893 (named *E. coli* HB101/Trp·TrpE·C11-C21). The deposition was also subsequently converted on Jun. 17, 1991 to an international deposition under Budapest Treaty at the same international depository authority, under the Accession Number FERM BP-3451.

(iv) Expression and Purification of Polypeptide Encoded by Clone C11-C21:

Expression and purification of a fused polypeptide were carried out substantially in the same manner as in the aforementioned procedure (ii), except that the expression plasmid Trp·TrpE·C11-C21 obtained by the above procedure (iii) was used instead of Trp·TrpE·C11-7.

EXAMPLE 6

Measurement of Anti-non-A non-B Type Hepatitis Virus Antibody in Serum from non-A non-B Hepatitis Patient (i) Measurement by Western Blotting:

The expressed product obtained and purified in Example 5 was subjected in turn to SDS-polyacrylamide gel electrophoresis [Laemmli; *Nature*, 277, 680 (1970)] and to blotting on a nitrocellulose filter (Bio-Rad, Trans-blot) in usual way. The filter was blocked with a 3% gelatin solution and then reacted with each serum samples from normal persons or non-A non-B hepatitis patients. After washing, the resulting filter was reacted with a peroxidase-labeled human IgG (goat antibody). Thereafter, the filter was washed again and soaked in a solution containing diaminobenzidine as reaction substrate to confirm color development.

The results are shown in FIGS. 21 and 22. In FIG. 21, the expressed polypeptide TrpE·C11-7 (group 1) obtained in Example 5-(ii) was used as antigen, and in FIG. 22, the expressed polypeptide TrpE·C11-C21 (group 2) in Example 5-(iv) was used. In each case, no reaction was observed with a normal serum sample, but a strong reaction with a patient's serum sample was found with a specific band.

(ii) Measurement by Enzyme-Linked Immunosorbent Assay (ELISA):

ELISA can be used as a means to make diagnosis of a large number of serum samples as compared to the case of western blotting method. ELISA was carried out as follows:

A purified antigen sample was diluted with PBS(−) to a concentration of 5 μg/ml and fixed to a micro-plate at 4° C. or room temperature. After washing several times with a washing solution, a diluted serum sample to be detected was added to the resulting plate and incubated for 1 hour at 37° C. or room temperature. After washing, peroxidase-labeled anti-human IgG (goat antibody) was added and incubated at 37° C. or room temperature to complete the reaction. After washing several times, 50 μl of a diaminobenzidine solution was added and incubated at 37° C. to develop color. Thereafter, the coloring reaction was stopped with 2M $H_2SO_4$ and the color was measured by a colorimeter.

Positive ratios in the case of the use of the expressed polypeptide antigens, TrpE·C11-7 (group 1) and TrpE·C11-C21 (group 2), of the present invention were compared with the case of the use of a commercially available kit of Chiron Corp. (Ortho HCV Ab ELISA Test). As shown in Table 1, the use of the Chiron's kit resulted in 69.7% of the positive ratio, while positive ratios in the case of the use of the TrpE·C11-7 and TrpE·C11-C21 were 78.8% and 84.8%, respectively Moreover, the positive ratio increased to 98.9% (30 of 31 cases) when these two expressed polypeptides of the present invention were used in combination (see FIG. 23).

EXAMPLE 7

Detection of non-A non-B Type Hepatitis Virus Group 2 Gene in Blood Plasma from non-A non-B Hepatitis Patient by RT-PCR RT-PCR was carried out as follows:

To 100 μl of a blood plasma sample collected from a non-A non-B hepatitis patient was added 300 μl of a 6M GTC solution (6M guanidine thiocyanate, 25 mM sodium citrate, 0.5% sarcosyl and 0.2M 2-mercaptoethanol), and the mixture was stirred. To this were further added 40 μl of 2M sodium acetate (pH 5.2), 400 μl of phenol and 80 μl of chloroform/isoamyl alcohol (49:1), and then thoroughly stirred. Aqueous solution layer separated from the mixture-was mixed with isopropyl alcohol and then subjected to centrifugation. Synthesis of cDNA was carried out using the pellet as a source of RNA. For the cDNA synthesis, an RNase inhibitor and a reverse transcriptase were added to a reaction solution containing 10 mM Tris-HCl, 0.01% gelatin, 1 mM each dNTP, 4 mM $MgCl_2$, 1 mM DTT and 100 pmole each primer, and the mixture was incubated at 37° C. for 2 hours to complete the reaction. Then, PCR was carried out using the cDNA obtained. In order to increase sensitivity and specificity for the detection of bands, a two step PCR method was employed, that is, first PCR using two primers (lst step PCR) and subsequent PCR using two primers which exist inside the first PCR product (2nd step PCR). For the PCR reaction, each amplification cycle was carried out using 100 μl of a reaction solution containing cDNA, 10 mM Tris-HCl, 0.01% gelatin, 2 mM each dNTP, 1.5 mM $MgCl_2$ and 50 pmol each primer, under reaction conditions of: denaturation, 94° C. for 1.5 minutes; annealing, 50° C. for 2 minutes; and chain elongation, 70° C. for 2 minutes. The amplification was repeated 35 cycles. Effects of several primers were evaluated. As the results, it was found that the group 2-specific DNA fragments are capable of being detected by the use of the following 4 primers:

1st step PCR kk21: 5'-GGATACACCGGTGACTTTGA-3' (SEQ ID NO:19)

kk22: 5'-TGCATGCACGTGGCGATGTA-3' (SEQ ID NO:20)

2nd step PCR kk26: 5'-GATGCCCACTTCCTCTCCCA-3' (SEQ ID NO:21)

kk27: 5'-GTCAGGGTAACCTCGTTGGT-3' (SEQ ID NO:22)

By applying these 4 primers to the PCR method, a DNA fragment of 206 bp can be detected. As a control, primers were synthesized from the base sequence of J1 and detection of group 1 DNA fragments was attempted. Results of the PCR from blood plasma samples of non-A non-B hepatitis patient are shown in Table 2.

It was known that DNA fragments from the non-A non-B hepatitis virus can be detected by both the PCRs using group 1 primers (i.e., group 1 PCR) and group 2 primers (i.e., group 2 PCR), and therefor two samples, Nos. 3 and 5, which are considered to include both groups 1- and 2-relating viruses were sequenecd for their vital genes. As shown in Table 3, when nucleotide sequences of DNA fragments obtained by group 2 PCR were compared with C10-13 which is a group 2 clone, homologies of 85% and 88% were observed, indicating effective detection of group 2 genes. When these two nucleotide sequences were compared with the aforementioned group 1 clone J1 (Miyamura et al, supra), only 64.8% and 68% homologies were observed. Results of the homology evaluation indicate that the primers used in the group 2 PCR can selectively detect group 2 viral genes.

TABLE 1

| Sample No. | TrpE.C11-7 (group 1) | TrpE.C11-C21 (group 2) | Kit of Chiron Corp. (group 1) |
|---|---|---|---|
| 1 | +++ | +++ | +++ |
| 2 | +++ | +++ | ++ |
| 3 | + | +++ | +++ |
| 4 | +++ | + | +++ |
| 5 | − | +++ | +++ |
| 6 | +++ | + | ++ |
| 7 | +++ | +++ | +++ |
| 8 | +++ | +++ | +++ |
| 9 | +++ | ++ | +++ |
| 10 | ± | ± | − |
| 11 | +++ | − | ++ |
| 12 | +++ | +++ | − |
| 13 | +++ | − | + |
| 14 | +++ | +++ | +++ |
| 15 | +++ | +++ | +++ |
| 16 | +++ | + | +++ |
| 17 | − | − | − |
| 18 | + | + | − |
| 19 | + | +++ | − |
| 20 | ++ | ++ | +++ |
| 21 | +++ | +++ | ++ |
| 22 | − | ++ | − |
| 23 | − | − | − |

TABLE 1-continued

| Sample No. | TrpE.C11-7 (group 1) | TrpE.C11-C21 (group 2) | Kit of Chiron Corp. (group 1) |
|---|---|---|---|
| 24 | + | + | + |
| 25 | +++ | +++ | +++ |
| 26 | − | ++ | − |
| 27 | +++ | +++ | ++ |
| 28 | + | + | +++ |
| 29 | +++ | +++ | +++ |
| 30 | +++ | ++ | +++ |
| 31 | − | ++ | +++ |
| 32 | − | ++ | − |
| 33 | + | − | − |
| NK | − | − | − |
| NP | − | − | − |

Note: NK and NP are negative controls.

TABLE 2

| Sample No. | Group 1 PCR | Group 2 PCR |
|---|---|---|
| 1 | + | − |
| 2 | + | ± |
| 3 | + | + |
| 4 | + | − |
| 5 | + | + |
| 6 | + | − |
| 7 | + | − |
| 8 | + | − |
| 9 | + | − |
| 10 | + | − |
| 11 | + | + |
| 13 | − | + |
| 42 | − | + |
| 169 | + | + |

TABLE 2-continued

| Sample No. | Group 1 PCR | Group 2 PCR |
|---|---|---|
| 260 | − | + |
| 244 | − | − |
| 248 | − | + |
| NC | − | − |

TABLE 3

| Sample No. | Nucleotide homology with clone C10-13 |
|---|---|
| 3 | 85% |
| 5 | 88% |

As seen from the foregoing examples, the present invention has the following advantages:

The cDNA sequences according to the present invention are specific to non-A non-B hepatitis, and polypeptides which are produced by incorporating these genes into a protein expression system in microbial host cells such as *E. coli* can react immunologically with sera samples from a number of non-A non-B hepatitis patients, whereby a kit for diagnosing non-A non-B hepatitis is capable of preparing with markedly high sensitivity and judging accuracy. Also, it is possible to make diagnosis of this disease using said sequences as a probe directly or other probes with higher specificity synthesized on the basis of the sequences. In addition, not only diagnosis of the disease but also isolation of non-A non-B hepatitis-specific genes can be accomplished by employing a gene amplification method (PCR method).

What is claimed is:

1. An isolated DNA fragment coding for a non-A non-B hepatitis-specific antigen polyopeptide, said DNA fragment having a nucleotide sequence selected from the group consisting of nucleotides shown in SEQ ID NOS. 1 and 14.

2. An expression vector containing the DNA fragment according to claim 1 in a cloning site downstream from a promoter in the vector.

3. A host cell transformed with an expression plasmid containing the DNA fragment according to claim 1 in a cloning site downstream from a promoter in the plasmid, wherein the host cell is a microorganism selected from the group consisting of *Escherichia coli, Bacillus subtilis* and yeasts.

4. A process for producing a recombinant non-A non-B hepatitis-specific antigen polypeptide, which comprises the steps of:

constructing a replicable expression vector having inserted therein a DNA fragment according to claim 1;

obtaining a transformant by introducing said expression vector into a host cell;

producing said recombinant polypeptide by culturing said transformant under such conditions that said DNA fragment is expressed; and recovering the recombinant polypeptide.

5. The expression vector according to claim 2 which is a plasmid.

6. The expression vector according to claim 5 wherein the plasmid is selected from the group consisting of plasmid Trp.TrpE.C11-C21 and plasmid Trp.TrpE.C11-7.

7. The host cell according to claim 3 which is *Escherichia coli.*

8. A single strand DNA sequence that is a PCR primer for amplification of non-A and non-B hepatitis virus genes, said single strand DNA sequence having a nucleotide sequence selected from the group consisting of nucleotide sequences shown in SEQ. ID NOS: 19, 20, 21 and 22.

* * * * *

UNITED STATES PATENT AND TRADEMARK OFFICE

CERTIFICATE OF CORRECTION

PATENT NO. : 5,641,654

DATED : June 24, 1997

INVENTOR(S) : Maki, et al.

It is certified that error appears in the above-identified patent and that said Letters Patent are hereby corrected as shown below:

On the Cover Page, Inventors should be listed as below:
Noboru Maki, Iruma-gun;
Kenjiro Yamaguchi, Iruma-shi;
Ayumi Tanaka, Matsudo-shi;
Michinori Kohara, Higashi-Katsushika-gun; all of Japan

Signed and Sealed this

Twenty-first Day of October 1997

Attest:

BRUCE LEHMAN

*Attesting Officer*

*Commissioner of Patents and Trademarks*

SEQUENCE LISTING ( 1 ) GENERAL INFORMATION:

( i i i ) NUMBER OF SEQUENCES:24

( 2 ) INFORMATION FOR SEQ ID NO:1:

( i ) SEQUENCE CHARACTERISTICS:
( A ) LENGTH:763 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:1:

```
CG CAG TCA TTC CAA GTG GCC CAT CTA CAC GCT CCC ACT GGC AGC GGC     47
   Gln Ser Phe Gln Val Ala His Leu His Ala Pro Thr Gly Ser Gly
     1               5                  10                  15

AAG AGT ACT AAA GTG CCG GCT GCA TAT GCC AGC CAA GGG TAC AAG GTG    95
Lys Ser Thr Lys Val Pro Ala Ala Tyr Ala Ser Gln Gly Tyr Lys Val
                 20                  25                  30

CTC GTC CTC AAC CCG TCC GTT GCC GCC ACC TTA GGT TTT GGA GCG TAT   143
Leu Val Leu Asn Pro Ser Val Ala Ala Thr Leu Gly Phe Gly Ala Tyr
             35                  40                  45

ATG TCT AAG GCA CAT GGC ACC GAC CCC AAC ATC AGA ACT GGG GTA AGG   191
Met Ser Lys Ala His Gly Thr Asp Pro Asn Ile Arg Thr Gly Val Arg
         50                  55                  60
```

-continued

```
ACT ATC ACC ACA GGC GCC CCC ATC ACG TAC TCC ACC TAC GGC AAG TTC    239
Thr Ile Thr Thr Gly Ala Pro Ile Thr Tyr Ser Thr Tyr Gly Lys Phe
     65                      70                      75

CTT GCC GAC GGT GGT TGT TCT GGG GGC GCT TAT GAC ATC ATA ATG TGT    287
Leu Ala Asp Gly Gly Cys Ser Gly Gly Ala Tyr Asp Ile Ile Met Cys
 80                      85                      90                  95

GAT GAG TGC CAC TCA ACT GAC GCG ACT TCC ATC TTG GGC ATC GGC ACG    335
Asp Glu Cys His Ser Thr Asp Ala Thr Ser Ile Leu Gly Ile Gly Thr
                100                     105                     110

GTC CTG GAC CAA GCG GAG ACG GCT GGA GCA CGG CTC GTC GTG CTC GCC    383
Val Leu Asp Gln Ala Glu Thr Ala Gly Ala Arg Leu Val Val Leu Ala
            115                     120                     125

ACC GCT ACG CCT CCG GGA TCG GTC ACC GTG CCA CAC CCG AAT ATT GAG    431
Thr Ala Thr Pro Pro Gly Ser Val Thr Val Pro His Pro Asn Ile Glu
        130                     135                     140

GAG GTG GCC CTG TCT AAC ACT GGA GAG ATC CCC TTC TAT GGC AAA GGC    479
Glu Val Ala Leu Ser Asn Thr Gly Glu Ile Pro Phe Tyr Gly Lys Gly
    145                     150                     155

ATC CCC ATT GAA GTC ATC AAG GGG GGA AGG CAT CTC ATT TTC TGC CAT    527
Ile Pro Ile Glu Val Ile Lys Gly Gly Arg His Leu Ile Phe Cys His
160                     165                     170                     175

TCC AAG AAG AAG TGC GAC GAG CTC GCC GCG AAG TTG TCA GGC CTC GGG    575
Ser Lys Lys Lys Cys Asp Glu Leu Ala Ala Lys Leu Ser Gly Leu Gly
                180                     185                     190

ATT AAT GCT GTG GCA TAC TAC CGG GGT CTT GAT GTG TCC GTC ATA CCG    623
Ile Asn Ala Val Ala Tyr Tyr Arg Gly Leu Asp Val Ser Val Ile Pro
            195                     200                     205

ACC AGC GGA GAC GTC GTT GTC GTG GCA ACA GAC GCT CTA ATG ACG GGC    671
Thr Ser Gly Asp Val Val Val Val Ala Thr Asp Ala Leu Met Thr Gly
        210                     215                     220

TAT ACC GGC GAT TTT GAC TCA GTG ATC GAC TGT AAC ACA TGC GTC ACC    719
Tyr Thr Gly Asp Phe Asp Ser Val Ile Asp Cys Asn Thr Cys Val Thr
    225                     230                     235

CAG ACA GTC GAC TTC AGC TTG GAC CCC ACC TTC ACC ATT GAG AC         763
Gln Thr Val Asp Phe Ser Leu Asp Pro Thr Phe Thr Ile Glu
240                     245                     250
```

( 2 ) INFORMATION FOR SEQ ID NO:2:

( i ) SEQUENCE CHARACTERISTICS:
( A ) LENGTH:615 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:2:

```
C ACG CCC GGT TTG CCC GTG TGT CAA GAC CAC CTG GAG TTC TGG GAA GCG    49

  Thr Pro Gly Leu Pro Val Cys Gln Asp His Leu Glu Phe Trp Glu Ala
   1               5                  10                  15

GTC TTC ACA GGT CTC ACG CAC ATT GAT GCC CAC TTC CTC TCC CAG ACA    97
Val Phe Thr Gly Leu Thr His Ile Asp Ala His Phe Leu Ser Gln Thr
            20                  25                  30

AAG CAA GGA GGA GAC AAC TTC GCG TAT CTA ACG GCC TAC CAG GCC ACA    145
Lys Gln Gly Gly Asp Asn Phe Ala Tyr Leu Thr Ala Tyr Gln Ala Thr
        35                  40                  45

GTG TGC GCT AGG GCA AAG GCC CCT CCT CCC TCG TGG GAT GTG ATG TGG    193
Val Cys Ala Arg Ala Lys Ala Pro Pro Pro Ser Trp Asp Val Met Trp
    50                  55                  60
```

-continued

```
AAA TGT CTA GCT AGG CTG AAG CCT ACA CTA ATT GGT CCT ACC CCC CTC     241
Lys Cys Leu Ala Arg Leu Lys Pro Thr Leu Ile Gly Pro Thr Pro Leu
 65                  70                  75                  80

CTG TAC CGC TTG GGT GCC GTG ACC AAC GAG GTT ACC CTG ACG CAC CCC     289
Leu Tyr Arg Leu Gly Ala Val Thr Asn Glu Val Thr Leu Thr His Pro
                 85                  90                  95

GTG ACG AAA TAC ATC GCC ACG TGC ATG CAA GCT GAC CTC GAG ATC ATG     337
Val Thr Lys Tyr Ile Ala Thr Cys Met Gln Ala Asp Leu Glu Ile Met
            100                 105                 110

ACG AGC ACA TGG GTC CTA GCA GGG GGG GTG CTA GCC GCC GTG GCA GCT     385
Thr Ser Thr Trp Val Leu Ala Gly Gly Val Leu Ala Ala Val Ala Ala
        115                 120                 125

TAC TGC CTG GCA ACC GGC TGT GTT TCC ATC ATC GGC CGC CTA CAC CTG     433
Tyr Cys Leu Ala Thr Gly Cys Val Ser Ile Ile Gly Arg Leu His Leu
    130                 135                 140

AAT GAT CAA GTG GTT GTG ACT CCT GAC AAA GAA ATC TTA TAT GAG GCC     481
Asn Asp Gln Val Val Val Thr Pro Asp Lys Glu Ile Leu Tyr Glu Ala
145                 150                 155                 160

TTT GAT GAG ATG GAA GAA TGC GCC TCC AAA GCC GCC CTC ATT GAG GAA     529
Phe Asp Glu Met Glu Glu Cys Ala Ser Lys Ala Ala Leu Ile Glu Glu
                165                 170                 175

GGG CAG CGG ATG GCG GAG ATG CTC AAG TCT AAG ATA CAA GGC CTC CTA     577
Gly Gln Arg Met Ala Glu Met Leu Lys Ser Lys Ile Gln Gly Leu Leu
            180                 185                 190

CAA CAG GCC ACA AGA CAG GCC CAA GAC ATA CAG CCA GC                  615
Gln Gln Ala Thr Arg Gln Ala Gln Asp Ile Gln Pro
        195                 200
```

( 2 ) INFORMATION FOR SEQ ID NO:3:

( i ) SEQUENCE CHARACTERISTICS:
( A ) LENGTH:771 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:3:

```
GT GAG CGA GCC TCA GGA ATG TTT GAC AGT GTA GTG CTC TGT GAG TGC       47

   Glu Arg Ala Ser Gly Met Phe Asp Ser Val Val Leu Cys Glu Cys
     1               5                  10                  15

TAT GAC GCA GGG GCT GCA TGG TAC GAG CTT ACA CCA GCG GAG ACC ACC      95
Tyr Asp Ala Gly Ala Ala Trp Tyr Glu Leu Thr Pro Ala Glu Thr Thr
                 20                  25                  30

GTC AGG CTC AGA GCG TAT TTC AAC ACA CCT GGC TTG CCT GTG TGT CAA     143
Val Arg Leu Arg Ala Tyr Phe Asn Thr Pro Gly Leu Pro Val Cys Gln
            35                  40                  45

GAC CAT CTT GAG TTC TGG GAG GCA GTT TTC ACC GGC CTC ACA CAC ATA     191
Asp His Leu Glu Phe Trp Glu Ala Val Phe Thr Gly Leu Thr His Ile
        50                  55                  60

GAT GCC CAC TTC CTT TCC CAG ACA AAG CAA GCA GGG GAC AAT TTC GCA     239
Asp Ala His Phe Leu Ser Gln Thr Lys Gln Ala Gly Asp Asn Phe Ala
    65                  70                  75

TAC TTG ACA GCC TAC CAG GCT ACA GTG TGC GCC AGA GCC AAA GCC CCT     287
Tyr Leu Thr Ala Tyr Gln Ala Thr Val Cys Ala Arg Ala Lys Ala Pro
 80                  85                  90                  95

CCC CCG TCC TGG GAC GTC ATG TGG AAG TGC CTG ACT CGG CTC AAG CCC     335
Pro Pro Ser Trp Asp Val Met Trp Lys Cys Leu Thr Arg Leu Lys Pro
                100                 105                 110
```

-continued

```
ACG CTT GTG GCC CCT ACA CCC CTT CTG TAC CGT TTA GGC TCT GTT ACT    383
Thr Leu Val Ala Pro Thr Pro Leu Leu Tyr Arg Leu Gly Ser Val Thr
            115                 120                 125

AAC GAG GTC ACC CTC ACA CAT CCT GTG ACG AAA TAC ATC GCC ACT TGC    431
Asn Glu Val Thr Leu Thr His Pro Val Thr Lys Tyr Ile Ala Thr Cys
        130                 135                 140

ATG CAA GCT GAC CTT GAG GTC ATG ACC AGC ACG TGG GTC CTA GCT GGG    479
Met Gln Ala Asp Leu Glu Val Met Thr Ser Thr Trp Val Leu Ala Gly
    145                 150                 155

GGG GTC TTG GCA GCC GTC GCC GCG TAT TGC CTG GCG ACT GGG TGT GTC    527
Gly Val Leu Ala Ala Val Ala Ala Tyr Cys Leu Ala Thr Gly Cys Val
160                 165                 170                 175

TCC ATC ATC GGC CGC TTG CAC ATC AAT CAG CGA GCC GTC GTT GCA CCA    575
Ser Ile Ile Gly Arg Leu His Ile Asn Gln Arg Ala Val Val Ala Pro
                180                 185                 190

GAC AAG GAG GTC CTT TAT GAG GCT TTT GAT GAG ATG GAG GAG TGT GCC    623
Asp Lys Glu Val Leu Tyr Glu Ala Phe Asp Glu Met Glu Glu Cys Ala
            195                 200                 205

TCT AAA GCG GCT CTC ATT GAA GAG GGG CAG CGG ATA GCC GAG ATG CTG    671
Ser Lys Ala Ala Leu Ile Glu Glu Gly Gln Arg Ile Ala Glu Met Leu
        210                 215                 220

AAG TCC AAG ATC CAA GGC TTA TTG CAG CAA GCC TCT AAA CAG GCC CAG    719
Lys Ser Lys Ile Gln Gly Leu Leu Gln Gln Ala Ser Lys Gln Ala Gln
    225                 230                 235

GAC ATA CAA CCC GCT GTG CAG CCT CAT GGC CCA AGG TGG AGC AAT TCT    767
Asp Ile Gln Pro Ala Val Gln Pro His Gly Pro Arg Trp Ser Asn Ser
240                 245                 250                 255

GGG C                                                              771
Gly
```

( 2 ) INFORMATION FOR SEQ ID NO:4:

( i ) SEQUENCE CHARACTERISTICS:
( A ) LENGTH:630 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:4:

```
C TGG TAT GAA CTT ACG CCT GCT GAG ACT ACG GTG AGA CTC CGG GCC TAT    49

  Trp Tyr Glu Leu Thr Pro Ala Glu Thr Thr Val Arg Leu Arg Ala Tyr
  1               5                   10                  15

TTC AAC ACG CCC GGC CTG CCT GTG TGT CAA GAC CAC CTG GAA TTC TGG    97
Phe Asn Thr Pro Gly Leu Pro Val Cys Gln Asp His Leu Glu Phe Trp
            20                  25                  30

GAG GCG GTC TTC ACA GGT CTC ACA CAC ATC GAT GCC CAC TTC CTC TCC    145
Glu Ala Val Phe Thr Gly Leu Thr His Ile Asp Ala His Phe Leu Ser
        35                  40                  45

CAG ACG AAG CAA GGA GGA GAT AAC TTT GCA TAT TTA ACA GCC TAC CAG    193
Gln Thr Lys Gln Gly Gly Asp Asn Phe Ala Tyr Leu Thr Ala Tyr Gln
    50                  55                  60

GCC ACA GTC TGC GCT AGG GCA AAG GCT CCC CCT CCT TCG TGG GAC GTG    241
Ala Thr Val Cys Ala Arg Ala Lys Ala Pro Pro Pro Ser Trp Asp Val
65                  70                  75                  80

ATG TGG AAG TGT TTG ATT AGG CTC AAA CCT ACA CTG ACT GGT CCT ACC    289
Met Trp Lys Cys Leu Ile Arg Leu Lys Pro Thr Leu Thr Gly Pro Thr
                85                  90                  95
```

-continued

```
CCC CTC CTG TAC CGC TTG GGT GCC GTG ACC AAC GAG GTT ACC CTG ACT     337
Pro Leu Leu Tyr Arg Leu Gly Ala Val Thr Asn Glu Val Thr Leu Thr
            100                 105                 110

CAC CCC ATG ACG AAA TAT ATC GCC ACT TGT ATG CAA GCT GAT CTT GAG     385
His Pro Met Thr Lys Tyr Ile Ala Thr Cys Met Gln Ala Asp Leu Glu
        115                 120                 125

ATC ATG ACA AGC ACA TGG GTC TTG GCG GGG GGG GTG CTA GCC GCT GTG     433
Ile Met Thr Ser Thr Trp Val Leu Ala Gly Gly Val Leu Ala Ala Val
    130                 135                 140

GCA GCT TAC TGC CTA GCG ACC GGC TGC ATT TCC ATC ATT GGC CGC CTT     481
Ala Ala Tyr Cys Leu Ala Thr Gly Cys Ile Ser Ile Ile Gly Arg Leu
145                 150                 155                 160

CAC CTG AAT GAT CGG GTG GTC GTG ACC CCT GAT AAG GAA ATT TTA TAT     529
His Leu Asn Asp Arg Val Val Val Thr Pro Asp Lys Glu Ile Leu Tyr
                165                 170                 175

GAG GCC TTT GAT GAG ATG GAA GAG TGC GCC TCC AAA GCC GCC CTC ATT     577
Glu Ala Phe Asp Glu Met Glu Glu Cys Ala Ser Lys Ala Ala Leu Ile
            180                 185                 190

GAG GAA GGG CAG CGG ATG GCG GAG ATG CTG AAG TCT AAA ATA CAA GGC     625
Glu Glu Gly Gln Arg Met Ala Glu Met Leu Lys Ser Lys Ile Gln Gly
        195                 200                 205

CTC TT                                                              630
Leu
```

( 2 ) INFORMATION FOR SEQ ID NO:5:

( i ) SEQUENCE CHARACTERISTICS:
( A ) LENGTH:1426 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:5:

```
GGG ATC AAC CCT AAC ATC AGG ACC GGA GTA CGG ACC GTG ACC ACC GGG      48
Gly Ile Asn Pro Asn Ile Arg Thr Gly Val Arg Thr Val Thr Thr Gly
  1               5                  10                  15

GAC TCC ATC ACC TAC TCC ACT TAT GGC AAG TTT ATC GCA GAT GGA GGT      96
Asp Ser Ile Thr Tyr Ser Thr Tyr Gly Lys Phe Ile Ala Asp Gly Gly
            20                  25                  30

TGC GCA CAT GGT GCC TAT GAC GTC ATC ATA TGC GAC GAA TGC CAT TCA     144
Cys Ala His Gly Ala Tyr Asp Val Ile Ile Cys Asp Glu Cys His Ser
        35                  40                  45

GTG GAC GCT ACT ACC ATC CTT GGC ATT GGA ACA GTC CTT GAC CAG GCT     192
Val Asp Ala Thr Thr Ile Leu Gly Ile Gly Thr Val Leu Asp Gln Ala
    50                  55                  60

GAG ACC GCA GGT GCC AGG CTA GTG GTT TTA GCC ACA GCC ACG CCA CCC     240
Glu Thr Ala Gly Ala Arg Leu Val Val Leu Ala Thr Ala Thr Pro Pro
 65                  70                  75                  80

GGT ACG GTA ACA ACT CCC CAC GCT AAC ATA GAG GAG GTG GCC CTT GGT     288
Gly Thr Val Thr Thr Pro His Ala Asn Ile Glu Glu Val Ala Leu Gly
                 85                  90                  95

CAC GAA GGC GAG ATT CCT TTT TAT GGC AAG GCT ATT CCC CTA GCT TTC     336
His Glu Gly Glu Ile Pro Phe Tyr Gly Lys Ala Ile Pro Leu Ala Phe
            100                 105                 110

ATC AAG GGG GGC AGA CAC CTA ATT TTT TGC CAT TCA AAG AAG AAG TGC     384
Ile Lys Gly Gly Arg His Leu Ile Phe Cys His Ser Lys Lys Lys Cys
        115                 120                 125

GAC GAG CTC GCA GCA GCC CTT CGG GGC ATG GGT ATC AAT GCC GTT GCC     432
Asp Glu Leu Ala Ala Ala Leu Arg Gly Met Gly Ile Asn Ala Val Ala
    130                 135                 140
```

-continued

```
TAC TAC AGG GGT CTC GAC GTC TCC GTT ATA CCA ACT CAA GGA GAC GTG    480
Tyr Tyr Arg Gly Leu Asp Val Ser Val Ile Pro Thr Gln Gly Asp Val
145                 150                 155                 160

GTG GTT GTC GCC ACC GAT GCC CTA ATG ACT GGA TAC ACC GGT GAC TTT    528
Val Val Val Ala Thr Asp Ala Leu Met Thr Gly Tyr Thr Gly Asp Phe
                165                 170                 175

GAC TCT GTC ATC GAC TGC AAC GTT GCA GTC ACT CAG ATT GTT GAC TTT    576
Asp Ser Val Ile Asp Cys Asn Val Ala Val Thr Gln Ile Val Asp Phe
            180                 185                 190

AGC CTA GAC CCA ACT TTT ACC ATC ACC ACT CAA ACC GTC CCT CAG GAG    624
Ser Leu Asp Pro Thr Phe Thr Ile Thr Thr Gln Thr Val Pro Gln Glu
        195                 200                 205

GCT GTC TCC CGT AGT CAA CGT AGA GGG AGA ACT GGG AGG GGG CGA CTG    672
Ala Val Ser Arg Ser Gln Arg Arg Gly Arg Thr Gly Arg Gly Arg Leu
    210                 215                 220

GGC ACT TAC AGG TAT GTC TCG TCA GGC GAG AGG CCG TCT GGG ATG TTC    720
Gly Thr Tyr Arg Tyr Val Ser Ser Gly Glu Arg Pro Ser Gly Met Phe
225                 230                 235                 240

GAC AGC GTA GTA CTC TGC GAG TGC TAT GAT GCC GGG GCA GCC TGG TAC    768
Asp Ser Val Val Leu Cys Glu Cys Tyr Asp Ala Gly Ala Ala Trp Tyr
                245                 250                 255

GAG CTT ACA CCT GCT GAG ACC ACA GTG AGA CTC CGG GCT TAT TTC AAC    816
Glu Leu Thr Pro Ala Glu Thr Thr Val Arg Leu Arg Ala Tyr Phe Asn
            260                 265                 270

ACG CCC GGT TTG CCC GTG TGT CAA GAC CAC CTG GAG TTC TGG GAA GCG    864
Thr Pro Gly Leu Pro Val Cys Gln Asp His Leu Glu Phe Trp Glu Ala
        275                 280                 285

GTC TTC ACA GGT CTC ACG CAC ATT GAT GCC CAC TTC CTC TCC CAG ACA    912
Val Phe Thr Gly Leu Thr His Ile Asp Ala His Phe Leu Ser Gln Thr
    290                 295                 300

AAG CAA GGA GGA GAC AAC TTC GCG TAT CTA ACG GCC TAC CAG GCC ACA    960
Lys Gln Gly Gly Asp Asn Phe Ala Tyr Leu Thr Ala Tyr Gln Ala Thr
305                 310                 315                 320

GTG TGC GCT AGG GCA AAG GCC CCT CCT CCC TCG TGG GAT GTG ATG TGG   1008
Val Cys Ala Arg Ala Lys Ala Pro Pro Pro Ser Trp Asp Val Met Trp
                325                 330                 335

AAA TGT CTA GCT AGG CTG AAG CCT ACA CTA ATT GGT CCT ACC CCC CTC   1056
Lys Cys Leu Ala Arg Leu Lys Pro Thr Leu Ile Gly Pro Thr Pro Leu
            340                 345                 350

CTG TAC CGC TTG GGT GCC GTG ACC AAC GAG GTT ACC CTG ACG CAC CCC   1104
Leu Tyr Arg Leu Gly Ala Val Thr Asn Glu Val Thr Leu Thr His Pro
        355                 360                 365

GTG ACG AAA TAC ATC GCC ACG TGC ATG CAA GTG AAC CTC GAG ATC ATG   1152
Val Thr Lys Tyr Ile Ala Thr Cys Met Gln Val Asn Leu Glu Ile Met
    370                 375                 380

ACG AGC ACA TGG GTC CTA GCA GGG GGG GTG CTA GCC GCC GTG GCA GCT   1200
Thr Ser Thr Trp Val Leu Ala Gly Gly Val Leu Ala Ala Val Ala Ala
385                 390                 395                 400

TAC TGC CTG GCA ACC GGC TGT GTT TCC ATC ATC GGC CGC CTA CAC CTG   1248
Tyr Cys Leu Ala Thr Gly Cys Val Ser Ile Ile Gly Arg Leu His Leu
                405                 410                 415

AAT GAT CAA GTG GTT GTG ACT CCT GAC AAA GAA ATC TTA TAT GAG GCC   1296
Asn Asp Gln Val Val Val Thr Pro Asp Lys Glu Ile Leu Tyr Glu Ala
            420                 425                 430

TTT GAT GAG ATG GAA GAA TGC GCC TCC AAA GCC GCC CTC ATT GAG GAA   1344
Phe Asp Glu Met Glu Glu Cys Ala Ser Lys Ala Ala Leu Ile Glu Glu
        435                 440                 445

GGG CAG CGG ATG GCG GAG ATG CTC AAG TCT AAG ATA CAA GGC CTC CTA   1392
Gly Gln Arg Met Ala Glu Met Leu Lys Ser Lys Ile Gln Gly Leu Leu
    450                 455                 460
```

-continued

```
CAA CAG GCC ACA AGA CAG GCC CAA GAC ATA CAG C                                  1426
Gln Gln Ala Thr Arg Gln Ala Gln Asp Ile Gln
465                 470                 475
```

( 2 ) INFORMATION FOR SEQ ID NO:6:

( i ) SEQUENCE CHARACTERISTICS:
( A ) LENGTH:855 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:6:

```
CG CAG ACA TTC CAA GTG GCC CAT CTG CAC GCT CCC ACT GGT AGC GGC                  47

   Gln Thr Phe Gln Val Ala His Leu His Ala Pro Thr Gly Ser Gly
    1               5                  10                  15

AAG AGC ACT AAG GTG CCG GCT GCA TAT GCG GCC CAA GGG TAC AAG GTA                 95
Lys Ser Thr Lys Val Pro Ala Ala Tyr Ala Ala Gln Gly Tyr Lys Val
                20                  25                  30

CTC GTC CTG AAC CCG TCC GTT GCC GCC ACT TTA GCC TTT GGG GCG TAC                143
Leu Val Leu Asn Pro Ser Val Ala Ala Thr Leu Ala Phe Gly Ala Tyr
            35                  40                  45

ATG TCT AAG GCA CAT GGT GTC GAC CCT AAC ATC AGA ACT GGG GTG AGG                191
Met Ser Lys Ala His Gly Val Asp Pro Asn Ile Arg Thr Gly Val Arg
        50                  55                  60

ACC ATC ACC ACG GGC GCT CCC ATC ACG TAC TCC ACC TAT GGT AAG TTC                239
Thr Ile Thr Thr Gly Ala Pro Ile Thr Tyr Ser Thr Tyr Gly Lys Phe
    65                  70                  75

CTT GCC GAC GGT GGT TGC TCT GGG GGC GCC TAT GAC ATC ATA ATA TGT                287
Leu Ala Asp Gly Gly Cys Ser Gly Gly Ala Tyr Asp Ile Ile Ile Cys
80                  85                  90                  95

GAT GAG TGC CAC TCA ACT GAC TCG ACA TCC ATC TTG GGC ATC GGC ACA                335
Asp Glu Cys His Ser Thr Asp Ser Thr Ser Ile Leu Gly Ile Gly Thr
                100                 105                 110

GTC CTG GAC CAA GCG GAG ACG GCT GGA GCG CGG CTC GTC GTG CTC GCT                383
Val Leu Asp Gln Ala Glu Thr Ala Gly Ala Arg Leu Val Val Leu Ala
            115                 120                 125

ACC GCT ACG CCT CCG GGA TCG GTC ACC GTG CCA CAT CCC AAT ATC GAG                431
Thr Ala Thr Pro Pro Gly Ser Val Thr Val Pro His Pro Asn Ile Glu
        130                 135                 140

GAG GTG GCC CTG TCC ACC ACT GGA GAG ATT CCC TTC TAC GGC AAA GCT                479
Glu Val Ala Leu Ser Thr Thr Gly Glu Ile Pro Phe Tyr Gly Lys Ala
    145                 150                 155

ATC CCC ATC GAG ACA ATC AAG GGG GGG AGG CAT CTC ATC TTC TGC CGT                527
Ile Pro Ile Glu Thr Ile Lys Gly Gly Arg His Leu Ile Phe Cys Arg
160                 165                 170

175

TCC AAG AAG AAG TGT GAC GAG CTC GCT GGA AAG CTG TCA GCC CTC GGA                575
Ser Lys Lys Lys Cys Asp Glu Leu Ala Gly Lys Leu Ser Ala Leu Gly
                180                 185                 190

ATC AAC GCT GTA GCG TAC TAC CGG GGT CTT GAT GTA TCC GTC ATA CCG                623
Ile Asn Ala Val Ala Tyr Tyr Arg Gly Leu Asp Val Ser Val Ile Pro
            195                 200                 205

ACC AGC GGA GAC GTC GTT GTC GTG GCA ACA GAC GCT CTA ATG ACG GGC                671
Thr Ser Gly Asp Val Val Val Val Ala Thr Asp Ala Leu Met Thr Gly
        210                 215                 220

TAC ACC GGT GAC TTT GAT TCA GTG ATC GAC TGC AAT ACA TGT GTC ACC                719
Tyr Thr Gly Asp Phe Asp Ser Val Ile Asp Cys Asn Thr Cys Val Thr
    225                 230                 235
```

```
CAG ACA GTC GAC TTC AGC TTG GAC CCT ACC TTC ACC ATT GAG ACG ACG    767
Gln Thr Val Asp Phe Ser Leu Asp Pro Thr Phe Thr Ile Glu Thr Thr
240                 245                 250                 255

ACC GTG CCT CAA GAC GCG GTG TCA CGC TCG CAG CGG CGA GGC AGA ACT    815
Thr Val Pro Gln Asp Ala Val Ser Arg Ser Gln Arg Arg Gly Arg Thr
                260                 265                 270

GGT AGG GGT AGA GGG GGC ATA TAC AGG TTT GTG ACT CCA G              855
Gly Arg Gly Arg Gly Gly Ile Tyr Arg Phe Val Thr Pro
            275                 280
```

( 2 ) INFORMATION FOR SEQ ID NO:7:

( i ) SEQUENCE CHARACTERISTICS:
( A ) LENGTH:315 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:7:

```
GAC GAG CTC GCC GCA AAG CTG TCA GGC CTC GGA GTC AAT GCT GTG GCA     48
Asp Glu Leu Ala Ala Lys Leu Ser Gly Leu Gly Val Asn Ala Val Ala
 1               5                  10                  15

TAC TAC CGG GGT CTC GAT GTG TCT GTC ATA CCG ACG AGC GGG GAC GTC     96
Tyr Tyr Arg Gly Leu Asp Val Ser Val Ile Pro Thr Ser Gly Asp Val
            20                  25                  30

GTT GTT GTG GCA ACA GAC GCT CTA ATG ACG GGC TAT ACC GGC GAC TTT    144
Val Val Val Ala Thr Asp Ala Leu Met Thr Gly Tyr Thr Gly Asp Phe
        35                  40                  45

GAC TCG GTG ATC GAC TGC AAT ACA TGT GTC ACC CAA ACA GTC GAT TTC    192
Asp Ser Val Ile Asp Cys Asn Thr Cys Val Thr Gln Thr Val Asp Phe
    50                  55                  60

AGC TTG GAC CCT ACT TTC ACC ATT GAG ACG ACG ACC GTG CCC CAA GAC    240
Ser Leu Asp Pro Thr Phe Thr Ile Glu Thr Thr Thr Val Pro Gln Asp
 65                 70                  75                  80

GCG GTG TCG CGC TCG CAG CGG CGA GGC AGG ACT GGT AGG GGC AGG GTG    288
Ala Val Ser Arg Ser Gln Arg Arg Gly Arg Thr Gly Arg Gly Arg Val
                85                  90                  95

GGC ATA TAC AGG TTT GTG ACT CCC GAG                                315
Gly Ile Tyr Arg Phe Val Thr Pro Glu
            100                 105
```

( 2 ) INFORMATION FOR SEQ ID NO:8:

( i ) SEQUENCE CHARACTERISTICS:
( A ) LENGTH:911 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:8:

```
GT GAT GAG CTC GCC GCA AAG CTC TCA AGC CTC GGA CTC AAC GCT GTA     47

   Asp Glu Leu Ala Ala Lys Leu Ser Ser Leu Gly Leu Asn Ala Val
    1               5                  10                  15

GCA TAT TAC CGG GGT CTT GAT GTG TCC GTC ATA CCG ACT AGT GGA GAC     95
Ala Tyr Tyr Arg Gly Leu Asp Val Ser Val Ile Pro Thr Ser Gly Asp
                20                  25                  30

GTC GTT GTC GTG GCA ACA GAC GCT CTA ATG ACG GGC TAT ACC GGC GAC    143
Val Val Val Val Ala Thr Asp Ala Leu Met Thr Gly Tyr Thr Gly Asp
            35                  40                  45
```

-continued

```
TTT GAC TCA GTG ATC GAC TGT AAC ACA TGT GTC ACC CAG ACA GTT GAT     191
Phe Asp Ser Val Ile Asp Cys Asn Thr Cys Val Thr Gln Thr Val Asp
         50                  55                  60

TTC AGC TTG GAT CCA ACC TTC ACC ATT GAG ACG ACG ACC GTG CCT CAA     239
Phe Ser Leu Asp Pro Thr Phe Thr Ile Glu Thr Thr Thr Val Pro Gln
     65                  70                  75

GAC GCG GTG TCG CGC TCG CAG CGG CGA GGT AGG ACT GGC AGG GGC AGG     287
Asp Ala Val Ser Arg Ser Gln Arg Arg Gly Arg Thr Gly Arg Gly Arg
 80                  85                  90                  95

GGC GGC ATC TAT AGG TTT GTG ACT CCA GGA GAA CGG CCC TCG GGC ATG     335
Gly Gly Ile Tyr Arg Phe Val Thr Pro Gly Glu Arg Pro Ser Gly Met
                100                 105                 110

TTC GAT TCC TCG GTC CTG TGT GAG TGT TAT GAC GCG GGC TGT GCT TGG     383
Phe Asp Ser Ser Val Leu Cys Glu Cys Tyr Asp Ala Gly Cys Ala Trp
            115                 120                 125

TAT GAG CTC ACG CCC GCC GAG ACC ACG GTT AGG TTG CGG GCT TAC CTA     431
Tyr Glu Leu Thr Pro Ala Glu Thr Thr Val Arg Leu Arg Ala Tyr Leu
        130                 135                 140

AAT ACA CCA GGG TTG CCC GTC TGC CAG GAC CAT CTG GAG TTC TGG GAG     479
Asn Thr Pro Gly Leu Pro Val Cys Gln Asp His Leu Glu Phe Trp Glu
    145                 150                 155

GGC GTC TTC ACA GGC CTC ACC CAC ATA GAT GCC CAT TTC TTG TCT CAG     527
Gly Val Phe Thr Gly Leu Thr His Ile Asp Ala His Phe Leu Ser Gln
160                 165                 170                 175

ACT AAG CAG GCA GGA CAC AAC TTT CCC TAC CTG GTG GCA TAC CAA GCT     575
Thr Lys Gln Ala Gly His Asn Phe Pro Tyr Leu Val Ala Tyr Gln Ala
                180                 185                 190

ACA GTG TGC GCC AGG GCT CAG GCT CCA CCT CCA TCG TGG GAC CAA ATG     623
Thr Val Cys Ala Arg Ala Gln Ala Pro Pro Pro Ser Trp Asp Gln Met
            195                 200                 205

TGG AAG TGT CTC ATA CGG CTG AAA CCT ACG CTG CAC GGG CCA ACA CCC     671
Trp Lys Cys Leu Ile Arg Leu Lys Pro Thr Leu His Gly Pro Thr Pro
        210                 215                 220

CTG CTG TAT AGG CTA GGA GCC GTG GAA AAT GAG GTC ACC CTC ACA CAC     719
Leu Leu Tyr Arg Leu Gly Ala Val Glu Asn Glu Val Thr Leu Thr His
    225                 230                 235

CCC ATA ACC AAA TTC ATC ATG GCA TGC ATG TCG GCT GAT CTG GAG GTC     767
Pro Ile Thr Lys Phe Ile Met Ala Cys Met Ser Ala Asp Leu Glu Val
240                 245                 250                 255

GTC ACC AGC ACC TGG GTG CTG GTG GGC GGA GTC CTT GCA GCT CTG GCC     815
Val Thr Ser Thr Trp Val Leu Val Gly Gly Val Leu Ala Ala Leu Ala
                260                 265                 270

GCA TAT CGC CTG ACA ACA GGC AGC GTG GTC ATC GTG GGT AGG ATC ATC     863
Ala Tyr Arg Leu Thr Thr Gly Ser Val Val Ile Val Gly Arg Ile Ile
            275                 280                 285

TTG TCT GGG AGG CCG GCT GTC ATT CCC GAC AGG GAA GTC CTT TAC CGG     911
Leu Ser Gly Arg Pro Ala Val Ile Pro Asp Arg Glu Val Leu Tyr Arg
        290                 295                 300
```

( 2 ) INFORMATION FOR SEQ ID NO:9:

( i ) SEQUENCE CHARACTERISTICS:
( A ) LENGTH:489 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:9:

```
CG ACA ACC GTG CCC CAA GAC GCG GTG TCG CGC TCA CAA CGG CGG GGT     47
   Thr Thr Val Pro Gln Asp Ala Val Ser Arg Ser Gln Arg Arg Gly
     1               5                  10                  15

AGG ACA GGT AGG GGC AGG AGA GGC ATC TAC AGA TTT GTG ACT CCG GGA    95
Arg Thr Gly Arg Gly Arg Arg Gly Ile Tyr Arg Phe Val Thr Pro Gly
                20                  25                  30

GAA CGG CCC TCG GGC ATG TTC GAT TCT TCG GTC CTG TGT GAG TGC TAT   143
Glu Arg Pro Ser Gly Met Phe Asp Ser Ser Val Leu Cys Glu Cys Tyr
            35                  40                  45

GAC GCG GGC TGC GCT TGG ATC GAG CTC ACG CCC GCC GAG ACC TCA GTT   191
Asp Ala Gly Cys Ala Trp Ile Glu Leu Thr Pro Ala Glu Thr Ser Val
        50                  55                  60

AGG TTG CGG GCT TAC CTA AAT ACA CCA GGG TTG CCC GTC TGC CAG GAC   239
Arg Leu Arg Ala Tyr Leu Asn Thr Pro Gly Leu Pro Val Cys Gln Asp
    65                  70                  75

CAC CTG GAA TTC TGG GAG AGC GTC TTC ACA GGC CTC ACC CAT ATA GAT   287
His Leu Glu Phe Trp Glu Ser Val Phe Thr Gly Leu Thr His Ile Asp
 80                  85                  90                  95

GCC CAC TTC TTG TCC CAG ACC AAG CAG GCA GGA GAC AAC TTC CCC TAC   335
Ala His Phe Leu Ser Gln Thr Lys Gln Ala Gly Asp Asn Phe Pro Tyr
                100                 105                 110

CTG GTA GCA TAC CAA GCT ACA GTG TGC GCC AGG GCC CAG GCT CCA CCA   383
Leu Val Ala Tyr Gln Ala Thr Val Cys Ala Arg Ala Gln Ala Pro Pro
            115                 120                 125

CCA TCG TGG GAT CAA ATG TGG AAG TGT CTC ATA CGG CTG AAA CCT ACG   431
Pro Ser Trp Asp Gln Met Trp Lys Cys Leu Ile Arg Leu Lys Pro Thr
        130                 135                 140

CTA CAC GGG CCA ACA CCC CTG TTG TAT AGG CTG GGA GCC GTC CAA AAT   479
Leu His Gly Pro Thr Pro Leu Leu Tyr Arg Leu Gly Ala Val Gln Asn
    145                 150                 155

GAG GTC ACC C                                                     489
Glu Val Thr
160
```

( 2 ) INFORMATION FOR SEQ ID NO:10:

( i ) SEQUENCE CHARACTERISTICS:
( A ) LENGTH:1076 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:10:

```
GT GGT CTC CTG GGT GCC ATC GTG GTC AGC CTA ACG GGC CGC GAC AAG     47

   Gly Leu Leu Gly Ala Ile Val Val Ser Leu Thr Gly Arg Asp Lys
     1               5                  10                  15

AAC CAG GTC GAG GGG GAG GTT CAG GTG GTC TCC ACC GCA ACG CAA TCT    95
Asn Gln Val Glu Gly Glu Val Gln Val Val Ser Thr Ala Thr Gln Ser
                20                  25                  30

TTC CTG GCG ACC TGC GTC AAT GGC GTG TGT TGG ACC GTC TAC CAT GGC   143
Phe Leu Ala Thr Cys Val Asn Gly Val Cys Trp Thr Val Tyr His Gly
            35                  40                  45

GCC GGC TCG AAA ACC CTG GCC GGC CCG AAG GGT CCA GTC ACC CAA ATG   191
Ala Gly Ser Lys Thr Leu Ala Gly Pro Lys Gly Pro Val Thr Gln Met
        50                  55                  60

TAC ACT AAT GTG GAC CAG GAC CTC GTC GGC TGG CCG GCG CCC TCC GGG   239
Tyr Thr Asn Val Asp Gln Asp Leu Val Gly Trp Pro Ala Pro Ser Gly
    65                  70                  75
```

-continued

```
GCG CGG TCC TTG ACA CCA TGC ACC TGC GGC AGC TCG GAC CTT TAC TTG    287
Ala Arg Ser Leu Thr Pro Cys Thr Cys Gly Ser Ser Asp Leu Tyr Leu
 80                 85                  90                  95

GTC ACG AGG CAT GCT GAT GTC ATT CCG GTG CGC CGG CGG GGC GAT AGC    335
Val Thr Arg His Ala Asp Val Ile Pro Val Arg Arg Arg Gly Asp Ser
            100                 105                 110

AGG GGG AGC CTG CTT TCC CCC AGG CCC CTC TCC TAC TTG AAG GGC TCC    383
Arg Gly Ser Leu Leu Ser Pro Arg Pro Leu Ser Tyr Leu Lys Gly Ser
            115                 120                 125

TCA GGT GGT CCA CTG CTT TGC CCC TCG GGG CAC ATT GTG GGC ATC TTC    431
Ser Gly Gly Pro Leu Leu Cys Pro Ser Gly His Ile Val Gly Ile Phe
        130                 135                 140

CGG GCT GCC GTG TGC ACC CGG GGG GTT GCG AAG GCG GTG GAC TTT GTA    479
Arg Ala Ala Val Cys Thr Arg Gly Val Ala Lys Ala Val Asp Phe Val
    145                 150                 155

CCT GTC GAG TCT ATG GAA ACT ACT ATG CGG TCT CCG GTC TTC ACG GAT    527
Pro Val Glu Ser Met Glu Thr Thr Met Arg Ser Pro Val Phe Thr Asp
160                 165                 170                 175

AAT TCA TCC CCC CCG GCC GTA CCG CAG ACA TTC CAA GTG GCC CAT CTG    575
Asn Ser Ser Pro Pro Ala Val Pro Gln Thr Phe Gln Val Ala His Leu
                180                 185                 190

CAT GCC CCC ACT GGC AGC GGC AAG AGC ACT AAG GTG CCG GCT GCA TAC    623
His Ala Pro Thr Gly Ser Gly Lys Ser Thr Lys Val Pro Ala Ala Tyr
            195                 200                 205

GCA GCC CAG GGA TAC AAG GTA CTC GTC CTG AAC CCG TCC GTT GCC GCC    671
Ala Ala Gln Gly Tyr Lys Val Leu Val Leu Asn Pro Ser Val Ala Ala
        210                 215                 220

ACC TTA GGT TTT GGA GCA TAT ATG TCC AAG GCA CAT GGT GTC GAC CCT    719
Thr Leu Gly Phe Gly Ala Tyr Met Ser Lys Ala His Gly Val Asp Pro
    225                 230                 235

AAC ATC AGG ACT GGG GTA AGG ACC ATC ACT ACG GGC GCC CCC ATT ACA    767
Asn Ile Arg Thr Gly Val Arg Thr Ile Thr Thr Gly Ala Pro Ile Thr
240                 245                 250                 255

TAC TCC ACC TAT GGC AAG TTT CTT GCC GAC GGT GGT TGC TCC GGG GGC    815
Tyr Ser Thr Tyr Gly Lys Phe Leu Ala Asp Gly Gly Cys Ser Gly Gly
                260                 265                 270

GCC TAT GAC ATC ATA ATA TGT GAT GAG TGC CAC TCA ACT GAC TCG ACT    863
Ala Tyr Asp Ile Ile Ile Cys Asp Glu Cys His Ser Thr Asp Ser Thr
            275                 280                 285

TCC ATT TTG GGC ATT GGC ACG GTC CTG GAC CAA GCG GAG ACG GCT GGA    911
Ser Ile Leu Gly Ile Gly Thr Val Leu Asp Gln Ala Glu Thr Ala Gly
        290                 295                 300

GCG CGG CTC GTC GTG CTC GCC ACC GCT ACG CCT CCA GGA TCG GTC ACT    959
Ala Arg Leu Val Val Leu Ala Thr Ala Thr Pro Pro Gly Ser Val Thr
    305                 310                 315

GTG CCT CAT CCC AAC ATC GAG GAG GTG GCC TTG TCC AGC ACT GGA GAG   1007
Val Pro His Pro Asn Ile Glu Glu Val Ala Leu Ser Ser Thr Gly Glu
320                 325                 330                 335

ATT CCC TTC TAT GGC AAA GCC ATC CCC ATT GAG ACC ATC AAG GGG GGA   1055
Ile Pro Phe Tyr Gly Lys Ala Ile Pro Ile Glu Thr Ile Lys Gly Gly
                340                 345                 350

AGG CAT CTC ATT TTC TGC CAC                                       1076
Arg His Leu Ile Phe Cys His
            355
```

( 2 ) INFORMATION FOR SEQ ID NO:11:

( i ) SEQUENCE CHARACTERISTICS:

( A ) LENGTH:284 base pairs ( B ) TYPE:nucleic acid ( C ) STRANDEDNESS:double (D) TOPOLOGY:linear (ii) MOLECULE TYPE:cDNA to genomic RNA (xi) SEQUENCE DESCRIPTION: SEQ ID NO:11:

```
GTC GAC CCC AAT ATT AGA ACT GGG GTA AGG ACC ATC ACC ACG GGC GCT     48
Val Asp Pro Asn Ile Arg Thr Gly Val Arg Thr Ile Thr Thr Gly Ala
  1               5                  10                  15

CCC ATT ACG TAT TCT ACC TAT GGC AAA TTC CTT GCC GAC GGT GGT TGC     96
Pro Ile Thr Tyr Ser Thr Tyr Gly Lys Phe Leu Ala Asp Gly Gly Cys
             20                  25                  30

TCT GGG GGC GCC TAT GAC ATC ATA ATC TGT GAT GAG TGC CAC TCA ACT    144
Ser Gly Gly Ala Tyr Asp Ile Ile Ile Cys Asp Glu Cys His Ser Thr
         35                  40                  45

GAC TCG ACT TCC ATC TTG GGT ATC GGC ACA GCC CTG GAC CAA GCG GAG    192
Asp Ser Thr Ser Ile Leu Gly Ile Gly Thr Ala Leu Asp Gln Ala Glu
     50                  55                  60

ACG GCT GGA GCA CGG CTT GTC GTG CTC GCC ACC GCT ACG CCT CCA GGG    240
Thr Ala Gly Ala Arg Leu Val Val Leu Ala Thr Ala Thr Pro Pro Gly
 65                  70                  75                  80

TCG GTC ACC GTG CCG CAT CCC AAC ATC GAG GAG GTA GCC TTG CC         284
Ser Val Thr Val Pro His Pro Asn Ile Glu Glu Val Ala Leu
                 85                  90
```

(2) INFORMATION FOR SEQ ID NO:12:

(i) SEQUENCE CHARACTERISTICS:
(A) LENGTH:641 base pairs
(B) TYPE:nucleic acid
(C) STRANDEDNESS:double
(D) TOPOLOGY:linear (ii) MOLECULE TYPE:cDNA to genomic RNA (xi) SEQUENCE DESCRIPTION: SEQ ID NO:12:

```
G GAC AAC TCA TCT CCC CCG GCG GTA CCG CAG ACA TTC CAG GTG GCC CAT    49

  Asp Asn Ser Ser Pro Pro Ala Val Pro Gln Thr Phe Gln Val Ala His
    1               5                  10                  15

CTA CAC GCT CCC ACT GGC AGC GGC AAG AGC ACT AAG GTG CCG GCT GCA     97
Leu His Ala Pro Thr Gly Ser Gly Lys Ser Thr Lys Val Pro Ala Ala
             20                  25                  30

TAT GCA GCC CAA GGG TAC AAA GTA CTC GTC CTG AAC CCG TCC GTT GCC    145
Tyr Ala Ala Gln Gly Tyr Lys Val Leu Val Leu Asn Pro Ser Val Ala
         35                  40                  45

GCC ACC TTA AGT TTC GGG GCG TAT ATG TCC AAG GCA CAT GGT GTT GAC    193
Ala Thr Leu Ser Phe Gly Ala Tyr Met Ser Lys Ala His Gly Val Asp
     50                  55                  60

CCT AAT ATC AGA ACT GGG ACA AGG ACC ATC ACC ACG GGC GCT CCC ATC    241
Pro Asn Ile Arg Thr Gly Thr Arg Thr Ile Thr Thr Gly Ala Pro Ile
 65                  70                  75                  80

ACG TAC TCC ACC TAT GGC AAG TTC CTT GCA GAC GGT GGT TGC TCC GGA    289
Thr Tyr Ser Thr Tyr Gly Lys Phe Leu Ala Asp Gly Gly Cys Ser Gly
                 85                  90                  95

GGC GCC TAT GAC ATC ATA ATA TGC GAT GAG TGC CAC TCA ACA GAC TCG    337
Gly Ala Tyr Asp Ile Ile Ile Cys Asp Glu Cys His Ser Thr Asp Ser
            100                 105                 110

ACT TCC ATC TTA GGC ATT GGT ACG GTC CTG GAC CAA GCG GAG ACG GCT    385
Thr Ser Ile Leu Gly Ile Gly Thr Val Leu Asp Gln Ala Glu Thr Ala
        115                 120                 125

GGA GCG CGA CTC GTC GTG CTC GCC ACC GCT ACG CCT CCA GGA TCG GTC    433
Gly Ala Arg Leu Val Val Leu Ala Thr Ala Thr Pro Pro Gly Ser Val
    130                 135                 140
```

-continued

```
ACT GTG CCA CAT CCC AAC ATC GAG GAG GTG GCC CTG TCC AAC ACT GGA      481
Thr Val Pro His Pro Asn Ile Glu Glu Val Ala Leu Ser Asn Thr Gly
145                 150                 155                 160

GAG ATT CCC TTC TAT GGC AAA GCC ATC CCC ATT GAG GCC ATC AAG GGG      529
Glu Ile Pro Phe Tyr Gly Lys Ala Ile Pro Ile Glu Ala Ile Lys Gly
                165                 170                 175

GGG AGG CAT CTC ATT TTC TGC CAT TCT AAG AAG AAG TGT GAT GAG CTC      577
Gly Arg His Leu Ile Phe Cys His Ser Lys Lys Lys Cys Asp Glu Leu
            180                 185                 190

GCC ACG AAG CTG TCG GCC CTC GGA CTC AAT GCT GTA GCG TAC TAC CGG      625
Ala Thr Lys Leu Ser Ala Leu Gly Leu Asn Ala Val Ala Tyr Tyr Arg
        195                 200                 205

GGT CTT GAT GTG TCC G                                                641
Gly Leu Asp Val Ser
    210
```

( 2 ) INFORMATION FOR SEQ ID NO:13:

( i ) SEQUENCE CHARACTERISTICS:
( A ) LENGTH:432 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:13:

```
CA GGC GAG AGG CCG ACA GGG ATG TTT GAC AGC GTA GTG CTC TGT GAG        47
   Gly Glu Arg Pro Thr Gly Met Phe Asp Ser Val Val Leu Cys Glu
    1               5                  10                  15

TGC TAT GAT GCC GGG GCC GCC TGG TAC GAG CTT ACG CCT GCT GAG ACT       95
Cys Tyr Asp Ala Gly Ala Ala Trp Tyr Glu Leu Thr Pro Ala Glu Thr
                20                  25                  30

ACG GTG AGA CTC CGG GCT TAT TTC AAC ACG CCC GGT TTG CCT GTA TGT      143
Thr Val Arg Leu Arg Ala Tyr Phe Asn Thr Pro Gly Leu Pro Val Cys
            35                  40                  45

CAA GAC CAC CTA GAG TTC TGG GAA GCG GTC TTC ACA GGT CTC ACA CAC      191
Gln Asp His Leu Glu Phe Trp Glu Ala Val Phe Thr Gly Leu Thr His
        50                  55                  60

ATT GAT GCC CAC TTC CTC TCC CAG ACG AAG CAA GGA GGA GAC AAC TTT      239
Ile Asp Ala His Phe Leu Ser Gln Thr Lys Gln Gly Gly Asp Asn Phe
    65                  70                  75

GCG TAT CTA ACG GCC TAC CAG GCC ACA GTA TGC GCC AGG GCA AAG GCC      287
Ala Tyr Leu Thr Ala Tyr Gln Ala Thr Val Cys Ala Arg Ala Lys Ala
80                  85                  90                  95

CCC CCT CCT TCG TGG GAC GTG ATG TGG AAG TGT CTA ATC AGG CTC AAA      335
Pro Pro Pro Ser Trp Asp Val Met Trp Lys Cys Leu Ile Arg Leu Lys
                100                 105                 110

CCT ACA TTG ACT GGT CCT ACC CCC CTC CTG TAC CGC TTG GGT GCC GTG      383
Pro Thr Leu Thr Gly Pro Thr Pro Leu Leu Tyr Arg Leu Gly Ala Val
            115                 120                 125

ACT AAC GAG GTT ACC CTG ACG CAC CCC GTG ACG AAA TAT ATC GCC ACG T    432
Thr Asn Glu Val Thr Leu Thr His Pro Val Thr Lys Tyr Ile Ala Thr
        130                 135                 140
```

( 2 ) INFORMATION FOR SEQ ID NO:14:

( i ) SEQUENCE CHARACTERISTICS:
( A ) LENGTH:369 base pairs
( B ) TYPE:nucleic acid
( C ) STRANDEDNESS:double
( D ) TOPOLOGY:linear ( i i ) MOLECULE TYPE:cDNA to genomic RNA (xi) SEQUENCE DESCRIPTION: SEQ ID NO:14:

```
ATG GGC ACG AAT CCT AAA CCT CAA AGA AAA ACC AAA AGA AAC ACT AAC     48
Met Gly Thr Asn Pro Lys Pro Gln Arg Lys Thr Lys Arg Asn Thr Asn
 1               5                  10                  15

CGT CGC CCA CAA GAC GTT AAG TTT CCG GGC GGC GGC CAG ATC GTT GGC     96
Arg Arg Pro Gln Asp Val Lys Phe Pro Gly Gly Gly Gln Ile Val Gly
            20                  25                  30

GGA GTA TAC TTG TTG CCG CGC AGG GGC CCC AGA TTG GGT GTG CGC GCG    144
Gly Val Tyr Leu Leu Pro Arg Arg Gly Pro Arg Leu Gly Val Arg Ala
        35                  40                  45

ACA AGG AAG ACT TCG AAG CGG TCC CAG CCA CGT GGG GGG CGC CGG CCC    192
Thr Arg Lys Thr Ser Lys Arg Ser Gln Pro Arg Gly Gly Arg Arg Pro
    50                  55                  60

ATC CCT AAA GAT CGG CGC TCC ACT GGC AAG TCC TGG GGG AAA CCA GGA    240
Ile Pro Lys Asp Arg Arg Ser Thr Gly Lys Ser Trp Gly Lys Pro Gly
65                  70                  75                  80

TAC CCC TGG CCC CTA TAT GGG AAT GAG GGA CTC GGC TGG GCA GGG TGG    288
Tyr Pro Trp Pro Leu Tyr Gly Asn Glu Gly Leu Gly Trp Ala Gly Trp
                85                  90                  95

CTT CTG TCC CCC CGA GGT TCC CGT CCC TCT TGG GGC CCC ACT GAC CCC    336
Leu Leu Ser Pro Arg Gly Ser Arg Pro Ser Trp Gly Pro Thr Asp Pro
            100                 105                 110

CGG CAT AGG TCG CGC AAT GTG GGT AAG GTC ATC                        369
Arg His Arg Ser Arg Asn Val Gly Lys Val Ile
        115                 120
```

(2) INFORMATION FOR SEQ ID NO:15:

(i) SEQUENCE CHARACTERISTICS:
(A) LENGTH:932 base pairs
(B) TYPE:nucleic acid
(C) STRANDEDNESS:double
(D) TOPOLOGY:linear (ii) MOLECULE TYPE:cDNA to genomic RNA (xi) SEQUENCE DESCRIPTION: SEQ ID NO:15:

```
CG CGC AAC TTG GGT AAG GTC ATC GAT ACC CTC ACA TGC GGC TTC GCC      47

   Arg Asn Leu Gly Lys Val Ile Asp Thr Leu Thr Cys Gly Phe Ala
    1               5                  10                  15

GAC CTC ATG GGG TAC ATT CCG CTT GTC GGC GCC CCC CTA GGG GGT GCT     95
Asp Leu Met Gly Tyr Ile Pro Leu Val Gly Ala Pro Leu Gly Gly Ala
                20                  25                  30

GCC AGG GCC CTG GCA CAT GGT GTC CGG GTT CTG GAG GAC GGC GTG AAC    143
Ala Arg Ala Leu Ala His Gly Val Arg Val Leu Glu Asp Gly Val Asn
            35                  40                  45

TAT GCA ACA GGG AAT TTG CCC GGT TGC TCT TTC TCT ATC TTC CTC TTG    191
Tyr Ala Thr Gly Asn Leu Pro Gly Cys Ser Phe Ser Ile Phe Leu Leu
        50                  55                  60

GCT TTG CTG TCC TGT TTG ACC ATC CCA GCT TCC GCT TAT GAG GTG CGC    239
Ala Leu Leu Ser Cys Leu Thr Ile Pro Ala Ser Ala Tyr Glu Val Arg
    65                  70                  75

AAC GTA TCC GGG ATA TAC CAT GTC ACG AAC GAC TGC TCC AAC TCA AGT    287
Asn Val Ser Gly Ile Tyr His Val Thr Asn Asp Cys Ser Asn Ser Ser
80                  85                  90                  95

ATT GTG TAT GAG GCA GCG GAC ATG ATC ATG CAT ACC CCC GGG TGC GTG    335
Ile Val Tyr Glu Ala Ala Asp Met Ile Met His Thr Pro Gly Cys Val
                100                 105                 110

CCC TGC GTT CGG GAG AAC AAC TCC TCC CGT TGC TGG GCA GCG CTC ACT    383
Pro Cys Val Arg Glu Asn Asn Ser Ser Arg Cys Trp Ala Ala Leu Thr
            115                 120                 125
```

-continued

```
CCC ACG TTA GCG GCC AGG AAC ACC AGC GTC CCC ACT ACG ACA ATA CGA      431
Pro Thr Leu Ala Ala Arg Asn Thr Ser Val Pro Thr Thr Thr Ile Arg
        130                 135                     140

CGG CAT GTC GAT TTG CTC GTT GGG GCG GCT GCT TTC TGC TCC GCT ATG      479
Arg His Val Asp Leu Leu Val Gly Ala Ala Ala Phe Cys Ser Ala Met
    145                 150                     155

TAC GTG GGG GAT CTC TGT GGA TCT GTC TTC CTC GTT TCC CAG CTG TTC      527
Tyr Val Gly Asp Leu Cys Gly Ser Val Phe Leu Val Ser Gln Leu Phe
160                 165                 170                     175

ACT TTC TCA CCT CGT CGG CAT GAG ACA GTA CAG GAC TGC AAC TGC TCA      575
Thr Phe Ser Pro Arg Arg His Glu Thr Val Gln Asp Cys Asn Cys Ser
                180                     185                 190

ATC TAT CCC GGC CAC TTG ACA GGT CAT CGC ATG GCT TGG GAT ATG ATG      623
Ile Tyr Pro Gly His Leu Thr Gly His Arg Met Ala Trp Asp Met Met
            195                     200                 205

ATG AAC TGG TCA CCT ACA ACA GCC CTA GTG GTG TCG CAT CTA CTC CGG      671
Met Asn Trp Ser Pro Thr Thr Ala Leu Val Val Ser His Leu Leu Arg
        210                 215                     220

ATC CCA CAA GCT GTC ATG GAC ATG GTG GCG GGG GCT CAC TGG GGA GTC      719
Ile Pro Gln Ala Val Met Asp Met Val Ala Gly Ala His Trp Gly Val
    225                 230                     235

CTA GCG GGC CTC GCC TAC TAT TCC ATG GTG GGG AAC TGG GCT AAG GTT      767
Leu Ala Gly Leu Ala Tyr Tyr Ser Met Val Gly Asn Trp Ala Lys Val
240                 245                     250                 255

TTG ATT GTG ATG CTA CTC TTC GCC GGC GTT GAC GGG ACC ACC TAT GTG      815
Leu Ile Val Met Leu Leu Phe Ala Gly Val Asp Gly Thr Thr Tyr Val
                260                     265                 270

ACA GGG GGG ACG ACA GGC CGC ACC ACC AGC TCG TTC GCA TCC CTC TTT      863
Thr Gly Gly Thr Thr Gly Arg Thr Thr Ser Ser Phe Ala Ser Leu Phe
            275                     280                 285

ACA CTT GGG TCG CAT CAG AAG GTC CAG CTT ATA AAT ACC AAT GGC AGC      911
Thr Leu Gly Ser His Gln Lys Val Gln Leu Ile Asn Thr Asn Gly Ser
        290                 295                     300

TGG CAC ATC AAC AGG ACC GCC                                          932
Trp His Ile Asn Arg Thr Ala
    305                 310
```

( 2 ) INFORMATION FOR SEQ ID NO:16:

( i ) SEQUENCE CHARACTERISTICS:
( A ) LENGTH:559 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:16:

```
CGC CGG TAT GAG ACG GCG CAA GAC TGC AAT TGC TCA CTC TAT CCC GGT       48
Arg Arg Tyr Glu Thr Ala Gln Asp Cys Asn Cys Ser Leu Tyr Pro Gly
1               5                   10                  15

CAC GTA TCT GGT CAC CGC ATG GCT TGG GAT ATG ATG ATG AAC TGG TCA       96
His Val Ser Gly His Arg Met Ala Trp Asp Met Met Met Asn Trp Ser
            20                  25                  30

CCT ACA ACG GCC CTA GTG GTA TCG CAG CTA CTC CGG ATC CCA CAA GCC      144
Pro Thr Thr Ala Leu Val Val Ser Gln Leu Leu Arg Ile Pro Gln Ala
        35                  40                  45

GTC GTG GAC ATG GTG GCG GGG GCC CAC TGG GGA GTC CTA GCG GGC CTT      192
Val Val Asp Met Val Ala Gly Ala His Trp Gly Val Leu Ala Gly Leu
    50                  55                  60
```

-continued

GCC TAC TAT TCC ATG GTG GCG AAC TGG GCT AAG GTC TTG GTT GTG ATG 240
Ala Tyr Tyr Ser Met Val Ala Asn Trp Ala Lys Val Leu Val Val
Met 65 70 75 80

CTA CTC TTT GCC GGC GTT GAC GAC GGG AAG ACC ACC GTG ACG GGG GGG 288
Leu Leu Phe Ala Gly Val Asp Asp Gly Lys Thr Thr Val Thr Gly Gly
85 90 95

AGC GCA GCC TTC CAG TCC AGG AAG TTA GTG TCC TTC TTC TCA CCA GGG 336
Ser Ala Ala Phe Gln Ser Arg Lys Leu Val Ser Phe Phe Ser Pro Gly
100 105 110

CCG AAA CAA AAT ATC CAG CTT GAT AAC ACC AAC GGC AGC TGG CAC ATC 384
Pro Lys Gln Asn Ile Gln Leu Asp Asn Thr Asn Gly Ser Trp His Ile
115 120 125

AAC AGG ACT GCC CTG AAT TGC AAT GAC TCC CTC CAA ACT GGG TTC ATC 432
Asn Arg Thr Ala Leu Asn Cys Asn Asp Ser Leu Gln Thr Gly Phe Ile
130 135 140

GCT GCG CTG TTC TAC GCG CAC AAG TTC AAT TCG TCC GGA TGC CTA GAG 480
Ala Ala Leu Phe Tyr Ala His Lys Phe Asn Ser Ser Gly Cys Leu Glu
145 150 155 160

CGC ATG GCC AGC TGC CGC CCC ATT GAC AAG TTC GCG CAG GGG TGG GGT 528
Arg Met Ala Ser Cys Arg Pro Ile Asp Lys Phe Ala Gln Gly Trp Gly
165 170 175

CCC ATC ACT CAC GAT ACG CCT AAG ATC CCG G 559
Pro Ile Thr His Asp Thr Pro Lys Ile Pro
180 185

( 2 ) INFORMATION FOR SEQ ID NO:17:

( i ) SEQUENCE CHARACTERISTICS:
( A ) LENGTH:276 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:17:

GA CAC CGT ATG GCA TGG GAC ATG ATG ATG AAC TGG TCG CCC ACG GCT 47

His Arg Met Ala Trp Asp Met Met Met Asn Trp Ser Pro Thr Ala
1 5 10 15

ACC ATG ATT CTG GCG TAT GTG ATG CGC ATC CCC GAG GTC GTC ATG GAC 95
Thr Met Ile Leu Ala Tyr Val Met Arg Ile Pro Glu Val Val Met Asp
20 25 30

ATC ATT GGC GGG GCT CAC TGG GGC GTC ATG TTC GGC TTG GGC TAT TTT 143
Ile Ile Gly Gly Ala His Trp Gly Val Met Phe Gly Leu Gly Tyr Phe
35 40 45

TCT ATG CAG GGG GCT TGG GCA AAA GTC GTT GTC ATC CTT CTG CTG GCC 191
Ser Met Gln Gly Ala Trp Ala Lys Val Val Val Ile Leu Leu Leu Ala
50 55 60

GCT GGG GTG GAT GCG ACT ACC CTC AGC GTT GGG GGC TCT GCC GCG CAC 239
Ala Gly Val Asp Ala Thr Thr Leu Ser Val Gly Gly Ser Ala Ala His
65 70 75

ACC ACC GGC GGC CTT GTC GGC TTG TTC AAG CCT GGC G 276
Thr Thr Gly Gly Leu Val Gly Leu Phe Lys Pro Gly
80 85 90

( 2 ) INFORMATION FOR SEQ ID NO:18:

( i ) SEQUENCE CHARACTERISTICS:
( A ) LENGTH:742 base pairs
( B ) TYPE:nucleic acid
( C ) STRANDEDNESS:double ( D ) TOPOLOGY:linear ( i i ) MOLECULE TYPE:cDNA to genomic RNA ( x i ) SEQUENCE DESCRIPTION: SEQ ID NO:18:

```
CG CTT GTC GGC GCC CCC CTA GGG GGT GCT GCC AGG GCC CTG GCA CAT      47
   Leu Val Gly Ala Pro Leu Gly Gly Ala Ala Arg Ala Leu Ala His
    1               5                  10                  15

GGT GTC CGG GTT CTG GAG GAC GGC GTG AAC TAT GCA ACA GGG AAT TTG      95
Gly Val Arg Val Leu Glu Asp Gly Val Asn Tyr Ala Thr Gly Asn Leu
                 20                  25                  30

CCC GGT TGC TCT TTC TCT ATC TTC CTC TTG GCT TTG CTG TCC TGT TTG     143
Pro Gly Cys Ser Phe Ser Ile Phe Leu Leu Ala Leu Leu Ser Cys Leu
             35                  40                  45

ACC ATC CCA GCT TCC GCT TAT GAG GTG CGC AAC GTA TCC GGG ATA TAC     191
Thr Ile Pro Ala Ser Ala Tyr Glu Val Arg Asn Val Ser Gly Ile Tyr
         50                  55                  60

CAT GTC ACG AAC GAC TGC TCC AAC TCA AGT ATT GTG TAT GAG GCA GCG     239
His Val Thr Asn Asp Cys Ser Asn Ser Ser Ile Val Tyr Glu Ala Ala
     65                  70                  75

GAC ATG ATC ATG CAT ACC CCC GGG TGC GTG CCC TGC GTT CGG GAG AAC     287
Asp Met Ile Met His Thr Pro Gly Cys Val Pro Cys Val Arg Glu Asn
 80                  85                  90                  95

AAC TCC TCC CGT TGC TGG GCA GCG CTC ACT CCC ACG TTA GCG GCC AGG     335
Asn Ser Ser Arg Cys Trp Ala Ala Leu Thr Pro Thr Leu Ala Ala Arg
                100                 105                 110

AAC ACC AGC GTC CCC ACT ACG ACA ATA CGA CGG CAT GTC GAT TTG CTC     383
Asn Thr Ser Val Pro Thr Thr Thr Ile Arg Arg His Val Asp Leu
Leu

            115                 120                 125

GTT GGG GCG GCT GCT TTC TGC TCC GCT ATG TAC GTG GGG GAT CTC TGT     431
Val Gly Ala Ala Ala Phe Cys Ser Ala Met Tyr Val Gly Asp Leu Cys
        130                 135                 140

GGA TCT GTC TTC CTC GTT TCC CAG CTG TTC ACT TTC TCA CCT CGT CGG     479
Gly Ser Val Phe Leu Val Ser Gln Leu Phe Thr Phe Ser Pro Arg Arg
    145                 150                 155

CAT GAG ACA GTA CAG GAC TGC AAC TGC TCA ATC TAT CCC GGC CAC TTG     527
His Glu Thr Val Gln Asp Cys Asn Cys Ser Ile Tyr Pro Gly His Leu
160                 165                 170                 175

ACA GGT CAT CGC ATG GCT TGG GAT ATG ATG ATG AAC TGG TCA CCT ACA     575
Thr Gly His Arg Met Ala Trp Asp Met Met Met Asn Trp Ser Pro Thr
                180                 185                 190

ACA GCC CTA GTG GTG TCG CAT CTA CTC CGG ATC CCA CAA GCT GTC ATG     623
Thr Ala Leu Val Val Ser His Leu Leu Arg Ile Pro Gln Ala Val Met
            195                 200                 205

GAC ATG GTG GCG GGG GCC CAC TGG GGA GTC CTA GCG GGC CTT GCC TAC     671
Asp Met Val Ala Gly Ala His Trp Gly Val Leu Ala Gly Leu Ala Tyr
        210                 215                 220

TAT TCC ATG GTG GGG AAC TGG GCT AAG GTT TTG ATT GTG ATG CTA CTC     719
Tyr Ser Met Val Gly Asn Trp Ala Lys Val Leu Ile Val Met Leu Leu
    225                 230                 235

TTC GCC GGC GTT GAC GGG ACC AC                                      742
Phe Ala Gly Val Asp Gly Thr
240                 245
```

( 2 ) INFORMATION FOR SEQ ID NO:19:

( i ) SEQUENCE CHARACTERISTICS:
( A ) LENGTH:20 base pairs
( B ) TYPE:nucleic acid
( C ) STRANDEDNESS:single -continued ( D ) TOPOLOGY:linear ( x i ) SEQUENCE DESCRIPTION: SEQ ID NO:19:

GGATACACCG GTGACTTTGA 20

( 2 ) INFORMATION FOR SEQ ID NO:20:

( i ) SEQUENCE CHARACTERISTICS:
( A ) LENGTH:20 base pairs
( B ) TYPE:nucleic acid
( C ) STRANDEDNESS:single
( D ) TOPOLOGY:linear ( x i ) SEQUENCE DESCRIPTION: SEQ ID NO:20:

TGCATGCACG TGGCGATGTA 20

( 2 ) INFORMATION FOR SEQ ID NO:21:

( i ) SEQUENCE CHARACTERISTICS:
( A ) LENGTH:20 base pairs
( B ) TYPE:nucleic acid
( C ) STRANDEDNESS:single
( D ) TOPOLOGY:linear ( x i ) SEQUENCE DESCRIPTION: SEQ ID NO:21:

GATGCCCACT TCCTCTCCCA 20

( 2 ) INFORMATION FOR SEQ ID NO:22:

( i ) SEQUENCE CHARACTERISTICS:
( A ) LENGTH:20 base pairs
( B ) TYPE:nucleic acid
( C ) STRANDEDNESS:single
( D ) TOPOLOGY:linear ( x i ) SEQUENCE DESCRIPTION: SEQ ID NO:22:

GTCAGGGTAA CCTCGTTGGT 20

( 2 ) INFORMATION FOR SEQ ID NO:23:

( i ) SEQUENCE CHARACTERISTICS:
( A ) LENGTH:25 base pairs
( B ) TYPE:nucleic acid
( C ) STRANDEDNESS:single
( D ) TOPOLOGY:linear ( x i ) SEQUENCE DESCRIPTION: SEQ ID NO:23:

TTACGAATTC ATGGGCACGA ATCCT 25

( 2 ) INFORMATION FOR SEQ ID NO:24:

( i ) SEQUENCE CHARACTERISTICS:
( A ) LENGTH:27 base pairs
( B ) TYPE:nucleic acid
( C ) STRANDEDNESS:single
( D ) TOPOLOGY:linear ( x i ) SEQUENCE DESCRIPTION: SEQ ID NO:24:

TTAATCGATG ACCTTACCCA CATTGCG 27